(12) United States Patent
Anderson et al.

(10) Patent No.: US 6,709,814 B1
(45) Date of Patent: *Mar. 23, 2004

(54) PEPTIDES CAUSING FORMATION OF COMPACT STRUCTURES

(75) Inventors: David Anderson, San Bruno, CA (US); Tarikere Gururaja, Sunnyvale, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/285,912

(22) Filed: Apr. 2, 1999

Related U.S. Application Data

(60) Provisional application No. 60/080,444, filed on Apr. 2, 1998.

(51) Int. Cl.[7] ............................ C12N 15/63; C12N 15/12
(52) U.S. Cl. ............................ 435/6; 435/7.1; 435/23.4; 435/320.1
(58) Field of Search ............................ 435/6, 7.1, 23.4, 435/320.1

(56) References Cited

U.S. PATENT DOCUMENTS

| | | | |
|---|---|---|---|
| 5,491,074 A | | 2/1996 | Aldwin et al. ............. 435/69.7 |
| 6,025,485 A | * | 2/2000 | Kamb et al. .............. 536/25.32 |
| 6,180,343 B1 | * | 1/2001 | Anderson et al. .............. 435/6 |

FOREIGN PATENT DOCUMENTS

| | | |
|---|---|---|
| WO | 94/28173 A1 | 12/1992 |
| WO | 94/239332 A1 | 12/1994 |

OTHER PUBLICATIONS

Bodenmüller et al., "The neuropeptide head activator loses its biological activity by dimerization," *EMBO Journal*, 5(8):1825–1829 (Aug. 1986).
Cowley et al., "Structure of neuropeptide Y dimer in solution," *Eur J. Biochem.*, 205:1099–1106 (1992).
Vanhoof et al., "Proline motifs in peptides and their biological processing," *FASEB J.*, 9(9):736–744 (Jun. 1995).
Cunningham et al., "Minimized proteins," *Current Opinion in Structural Biology*, 7(4):457–462 (Aug. 1997).
Shai et al., "Antisense Peptide Recognition of Sense Peptides: Sequence Simplication and Evaluation of Forces Underlying the Interaction," *Biochemistry*, 28(22):8804–8811 (1989).
Naranda et al., "A peptide derived from an extracellular domain selectively inhibits receptor internalization: Target sequences on insulin and insulin–like growth factor 1 receptors," *Proc. Natl. Acad. Sci. USA*, 94:11692–11697 (Oct. 1997).
Szewczuk et al., "Conformationally Restricted Thrombin Inhibitors Resistant to Proteolytic Digestion," *Biochemistry*, 31(38):9132–9140 (1992).
Rizo et al., "Constrained Peptides: Models of Bioactive Peptides and Protein Substructures," *Annu. Rev. Biochem.*, 61:387–418 (1992).
Stradley et al., "Cyclic Pentapeptides as Models for Reverse Turns: Determination of the Equilibrium Distribution between Type I and Type II Conformations as Pro–Asn and Pro–Ala β–Turns," *Biopolymers*, 29:263–287 (1990).
O'Neil et al., "Identification of Novel Peptide Antagonists for GPIIb/IIIa from a Conformationally Constrained Phage Peptide Library," *Proteins: Structure, Function, and Genetics*, 14(4):509–515 (Dec. 1992).
Giebel et al., "Screening of Cyclic Peptide Phage Libraries Identifies Ligands That Bind Streptavidin with High Affinities," *Biochemistry*, 34(47):15430–15435 (1995).
Spatola et al., "Rediscovering an Endothelin Antagonist (BQ–123): A Self–Deconvoluting Cyclic Pentapeptide Library," *J. Med. Chem.*, 39(19):3842–3846 (1996).
Koivunen et al., "Selection of Peptides Binding to the $\alpha_5\beta_1$ Integrin from Phage Display Library," *J. Biological Chemistry*, 268(27):20205–20210 (1993).
Koivunen et al., "Isolation of a Highly Specific Ligand for the $\alpha_5\beta_1$ Integrin from a Phage Display Library," *J. Cell Biology*, 124(3):373–380 (Feb. 1994).
McBride et al., "Selection of Chymotrypsin Inhibitors from a Conformationally–constrained Combinatorial Peptide Library," *J. Mol. Biol.*, 259:819–827 (Jun. 1996).
Wang et al., "A Novel Matrix Attachment Region DNA Binding Motif Identified Using a Random Phage Peptide Library," *J. Biological Chemistry*, 270(40):23239–23242 (Oct. 1995).
Poujade et al., "Properties of Substance P Aggregates Application to the Synthesis and Purification of Substance P," *Biochemical and Biophysical Research Communications*, 114(3):1109–1116 (Aug. 1983).

(List continued on next page.)

*Primary Examiner*—Bennett Celsa
(74) *Attorney, Agent, or Firm*—James S. Keddie; Carol L. Francis; James J. Diehl

(57) ABSTRACT

The present invention is directed to compositions and methods including peptides which have a high affinity for each other and, when linked to a protein, are used to help fold the protein into a compact structure. By virtue of its stability and constraints, this scaffold can prolong the activity of any embedded protein sequences in the presence of cellular and other proteases. The compact structure can have other functional sequences embedded, and is preferable to linear and less constrained peptides for library screening, for creating structurally-biased peptide libraries and for targeting to specific intracellular and extracellular compartments. Compositions of the present invention can be displayed on the surface of viruses, archaebacteria, prokaryotic and eukaryotic cells for library screening, drug screening and display. Methods of the present invention are useful for screening in vivo for intracellular effector proteins modulating signaling pathways and to identify interacting proteins in vitro. Thus, the present invention is useful as a scaffold for gene therapy, for the isolation of new therapeutic drug leads and for potential use as a therapeutic in physiological fluids.

14 Claims, 21 Drawing Sheets

OTHER PUBLICATIONS

Mastropaolo et al., "Crystal Structure of Methionine–Enkephalin," *Biochemical and Biophysical Research Communications*, 134(2):698–703 (Jan. 1986).

Minakata et al., "Characterization of Amphiphilic Secondary Structures in Neuropeptide Y through the Design, Synthesis, and Study of Model Peptides," *J. Biological Chemistry*, 264(14):7907–7913 (May 1989).

Bachmair et al., "In Vivo Half–Life of a Protein Is a Function of Its Amino–Terminal Residue," *Science*, 234(4773):179–186 (Oct. 1986).

Gonda et al., "Universality and Structure of the N–end Rule", *J. Biological Chemistry*, 264(28):16700–16712 (Oct. 1989).

Varshafsky, A., "The N–end pathway of protein degradation," *Genes to Cell*, 2(1):13–28 (Jan. 1997).

Blalock et al., "Hydropathic Anti–Complementary of Amino Acids Based on the Genetic Code," *Biochem. Biophys. Res. Comm.*, 121(1):203–207 (May 1984).

Shai et al., "Anti–Sense peptide recognition of sense peptides: Direct quantitive charcterization wht the ribonuclease S–peptide using analytical high–performance affinity chromatography," *Biochem.*, 26:669–675 (1987).

Ghadiri et al., "A convergent approach to protein design. Metal Ion–assisted spontaneous self–assembly of a polypeptide into a triple–helix bundle protein," *J. Am. Chem. Soc.*, 114:825–831 (1992).

Eichler et al., "Novel alpha–glucosidase inhibitors identified using multiple cyclic peptide combinatorial libraries," *Mol. Divers.*, 1:233–240(1996).

Souroujon et al., "Peptide modulators of protein–protein interactions in intracellular signaling," *Nat. Biotechnol.*, 16(10):919–924 (1998).

Saffrich et al., "H–Nuclear magnetic resonance studies of the neuropeptide head activator," *Biochimica et Biophysica Acta*, 997(1/2):144–153 (Jul. 1989).

Bodenmuller et al., "Synthesis of new head–activator analogues and their application for improved radioimmunoassays," *Int. J. Peptide Res.*, 29(1):140–144 (Jan. 1987).

Rozzelle, Jr., et al., "Self–association of a synthetic peptide from the N terminus of the hepatitis delta virus protein into an immunoreative α–helical multimer," *Proc. Natl. Acad. Sci. USA*, 92(2):382–386 (Jan. 1995).

Juvvadi et al., "Structure–activity studies of normal and retro pidg cecropin–melttin hybrides," *Journal of Peptide Reserach*, 53(3):244–251 (Mar. 1999).

Merrifield et al., "Retro and retroenantio analogs of ceropin-melittin hybrids," *Proc. Natl. Acad. Sci. USA*, 92(8):3449–3453 (Apr. 1995).

Lacroix et al., "Reading protein sequences backwards," *Folding & Design*, 3(2):79–85 (1998).

Olszewski et al., "Does a backwardly read protein sequence have a unique native state?," *Protein Engineering*, 9(1):5–14 (Jan. 1996).

Guichard et al., "Antigenic mimicry of natural L–peptides with retro–inverso–peptidomimetics," *Proc. Natl. Acad. Sci. USA*, 91(21)9765–9769 (Oct. 1994).

Nakagawa et al., "Retro Analogs Related to Oxytocin," *Int. J. Peptide Protein Res.*, 8(5):465–479 (1976).

Bonora et al., "Retro–all–D and retro isomers of a formylmethionyl peptide chemoattractant: an insight into the mode of binding at the receptor on rabbit neutrophillis," *Biochimica et Biophysica Acta*, 884(3):545–549 (Dec. 1986).

Kessler et al., "Peptide conformation," *Int. J. Peptide Protein Res.*, 31(5):481–498 (May 1987).

Gomez et al., "Conformational pertubations in retro–analogs of the tBuCO–Ala–Gly–NHipr dipeptide," *Int. J. Peptide Protein Res.*, 34(6):480–486 (Dec. 1989).

Janes et al., "The Binding of the retro–Analogue of Glutathione Disulfide to Glutathione Reductase," *The Journal of Biological Chemistry*, 266(18):10443–10445 (Jun. 1990).

Guo et al., "Antiproliferative and antitumor activities of D–reverse peptides derived from the second type–1 repeat of thrombospondin–1," *J. Peptide Res.*, 50(3):210–221 (Sep. 1997).

Verdoliva et al., "Antigenicity of topochemically related peptides," *Biochimica et Biophysica Acta.*, 1253(1):57–62 (Nov. 1995).

Shinde and Inouye, "Intramolecular chaperones and protein folding," *TIBS Trends in Biochemical Sciences* 18(11):442–446 (1993).

* cited by examiner

PAGE 1 OF 2

PAGE 2 OF 2

PAGE 1 OF 2

PAGE 2 OF 2

PAGE 1 OF 4

PAGE 2 OF 4

PAGE 3 OF 4

CGTIVTMEYRIDRTRSFC + 1 mM DTT + elastase

| reaction, file | MS peak RT | MH+ obs/expected, | sequence | | |
|---|---|---|---|---|---|
| peptide 102397-0 25.16 | 36.20 min. | 2150.2/2151.01 c [CGTIVTMEYRIDRTRSFC] | mono | | parent main |
| +elastase 176 min. 102397-3 25.16 | 37.20 | 2150.2/2151.01 | mono | | parent main |
| | 38.86 | 2162.2/ | mono | | med |
| | 40.05 | 4297.8/ | mono | [CGTIVTMEYRIDRTRSFC]₂ oxidized dimer | small |
| | 36.81 | 2048.2/2048.01 | mono | CGTIVTMEYRIDRTRSF | med |
| | 35.6 | 1670.0/ | mono | | med |
| | 34.8 | 1705.3/ 2178.4/ | mono mono | | v. small small |
| | 34.23 | 1011.5/1012.51 1028.3/ | ?? mono | mono TIVTMEYR | v. small med |
| | 33.56 | 1658.0/1658.0 1016.3/1016.44 2167.3/ | mono mono avg. | CGTIVTMEYRIDRT CGTIVTMEY parent-O | med big |
| | 31.0 | 736.2/ | mono | | small |
| | 30.23 | 1673.8/1673.84 1576.9/1576.74 724.2/724.34 | mono mono mono | VTMEYRIDRTRSF MEYRIDRTRSFC CGTIVTM | med |
| | 28.15 | 1444.9/1445.7 1342.6/1342.69 1083.6/1083.53 1152.6/1153.54 1184.6/1184.57 | mono mono mono mono mono | EYRIDRTRSFC EYRIDRTRSF MEYRIDRT RIDRTRSFC TMEYRIDRT | med |
| | 25.7 | | | | small |
| | 23.78 23.05 | 1266.2/ 1050.6/1050.58 593.2/593.72 | avg mono avg | RIDRTRSF CGTIVT | big med |
| | 22.47 | 952.4/952.49 1200.6/ | mono mono | EYRIDRT | v. small med small |
| | 16.81 | 511.2/ | mono | | small |

Other peaks:
EYRIDRTRSFC
RIDRTRSF
EYRIDRTRSF
VTMEYRIDRTRSF
CGTIVTMEYRIDRTRSF
CGTIVTMEYRIDRT
CGTIVTM
CGTIVT
EYRIDRT
MEYRIDRT
TMEYRIDRT 100 nM elastase
10 μM peptide
pH 7.88, 25 C

FIG. 5A

PAGE 1 OF 4

PAGE 2 OF 4

PAGE 3 OF 4

| reaction, file | MS peak RT | MH+ obs/expected, sequence | |
|---|---|---|---|
| peptide 1007797A 5.192 | 35.3 min. | 2149.8/2150.51 avg C[CGTIVTMEYRIDRTRSFC] | |
| +elastase 16 min. 101097-1 25.1 | 34.75 | 2149.9/2150.51 avg C[CGTIVTMEYRIDRTRSFC] | |
| | 33.01 | 2168.3/2168.5 avg C[CGTIVTMEYRIDRTRSFC]H₂O | |
| +elastase 128 min +DTT 101097-4, 25.1 | 37.2 | 2152.1/2152.5 CGTIVTMEYRIDRTRSFC | med |
| | 33.2 | 1016.3/1017.2 avg CGTIVTMEY | big |
| | 24.9 | 1153.5/1154.3 avg RIDRTRSFC | big |
| | 31.3 | 1678.65/1677.95 avg TMEYRIDRTRSFC | small |
| | 29.07 | 1445.6/1445.65 avg EYRIDRTRSFC | small |
| | 24.04 | 492.0/492.25 mono CGTIV | v. small |

Other peaks:
TMEYRIDRTRSFC
EYRIDRTRSFC
CGTIV 100 nM elastase
10 μM peptide
pH 7.88, 25 C
C18 rpc: 1 mm x 25 cm
150 μl/m
100: H₂O 4 min.
-> 40% MeCN 40 min.

FIG. 5B
PAGE 4 OF 4

PAGE 1 OF 4

PAGE 2 OF 4

PAGE 3 OF 4

| reaction, file | MS peak RT | MH+ obs/expected | | sequence | |
|---|---|---|---|---|---|
| peptide EFLIV18E 25.6 | 35.43 | 3775.2/3775.10 | mono | EFLIVKS-VGTIVTMEYRIDRTRSFV-EFLIVKS | |
| +elastase 16 min. | 36.5 | 3622.0/ | | | |
| | 36.07 | 3775.0/3775.1 | mono | EFLIVKS-VGTIVTMEYRIDRTRSFV-EFLIVKS | small |
| | | | | | big |
| | 30.5 | 953.3/953.53 | mono | SFVEFLIV | |
| | 29.22 | 1828.6/1828.98 | mono | EFLIVKSVGTIVTMEY | small |
| | 24.88 | 1167.4/1167.68 | mono | SFVEFLIVKS | v. small |
| | 23.83 | 1965.1/1965.14 | mono | RIDRTRSFVEFLIVKS | v. small |
| +elastase 166 min. 25.6 EFLIV18D | 36.29 | 3775.2/3775.10 | mono | EFLIVKS-VGTIVTMEYRIDRTRSFV-EFLIVKS | |
| | 33.75 | 3660.8/ | | | |
| | 33.75 | 3235.6/3235.72 | mono | EFLIVKSVGTIVTMEYRIDRTRSFVEF | v.v. small |
| | 30.76 | 953.3/953.53 | mono | SFVEFLIV | small |
| | 29.38 | 1828.6/1828.98 | mono | EFLIVKSVGTIVTMEY | small |
| | 29.38 | 866.2/866.5 | mono | FVEFLIV | v. small |
| | 29.38 | 2470.3/2470.34 | mono | EFLIVKSVGTIVTMEYRIDRT | v. small |
| | 23.95 | 1965.1/1965.14 | mono | RIDRTRSFVEFLIVKS | v. small |
| | 22.28 | 741.1/741.38 | mono | SFVEFL | v.v. small |
| | 16.00 | 620.1/620.37 | mono | EFLIV or VEFLI | v.v. small |
| | 13.01 | 620.1/620.37 | mono | VEFLIV or EFLIV | v.v. small |
| | 13.01 | 476.2/476.27 | mono | SVGTI | small |
| | 10.20 | 628.1/628.30 | mono | SFVEF | small |
| | 4.57 | 935.4/935.52 | mono | KSVGTIVTM | v. small |
| | 4.57 | 807.2/807.43 | mono | SVGTIVTM | v. small |

Other very small peaks:
EFLIVKSVGTIVTMEYRIDRTRSFVEF
EFLIVKSVGTIVTMEYRIDRT
EFLIVKSVGTIVTMEY
RIDRTRSFVEFLIVKS
SFVEFLIV
FVEFLIV
SFVEF 100 nM elastase
10 μM peptide
pH 7.88, 25 C

FIG. 5C
PAGE 4 OF 4

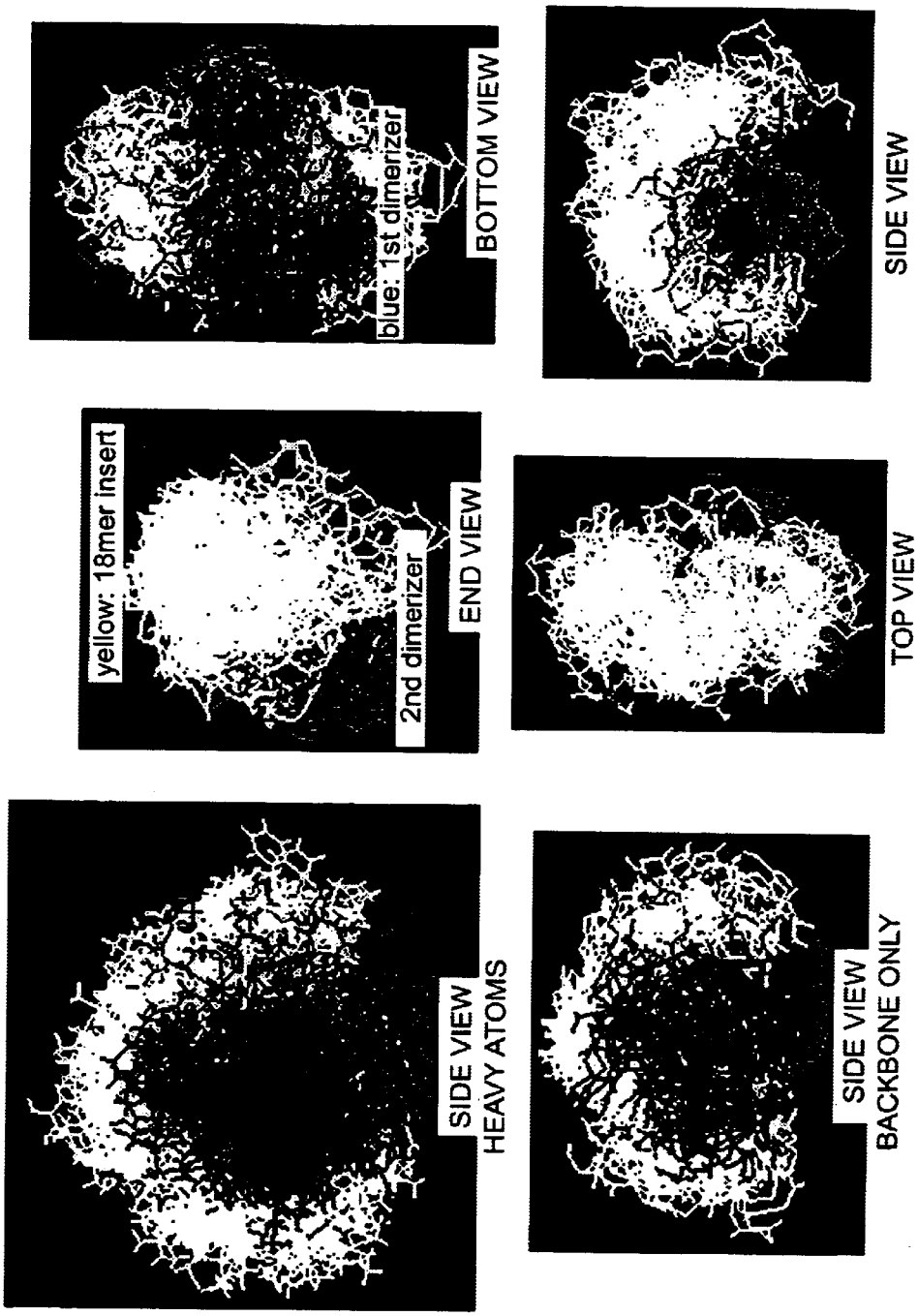

SEQUENCE LISTING

```
<160> NUMBER OF SEQ ID NOS: 150

<210> SEQ ID NO 1
<211> LENGTH: 11
<212> TYPE: PRT
<213> ORGANISM: coelenterate Hydra

<400> SEQUENCE: 1

Glu Pro Pro Gly Gly Ser Lys Val Ile Leu Phe
 1               5                  10

<210> SEQ ID NO 2
<211> LENGTH: 6
<212> TYPE: PRT
<213> ORGANISM: coelenterate Hydra

<400> SEQUENCE: 2

Ser Lys Val Ile Leu Phe
 1               5

<210> SEQ ID NO 3
<211> LENGTH: 4
<212> TYPE: PRT
<213> ORGANISM: coelenterate Hydra

<400> SEQUENCE: 3

Val Ile Leu Phe
 1

<210> SEQ ID NO 4
<211> LENGTH: 7
<212> TYPE: PRT
<213> ORGANISM: coelenterate Hydra

<400> SEQUENCE: 4

Glu Pro Pro Gly Gly Ser Lys
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 5

Phe Leu Ile Val Lys
 1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence
<223> OTHER INFORMATION: Description of Artificial Sequence: Synthetic

<400> SEQUENCE: 6

Glu Phe Leu Ile Val Lys Ser
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 7

Lys Phe Val Leu Ile Lys Ser
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 8

Val Ser Ile Lys Phe Glu Leu
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 9

Leu Ile Val Lys Ser
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 10

Glu Phe Leu Ile Val Lys
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 11

Lys Phe Leu Ile Val Lys
  1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 12

Phe Glu Ser Ile Lys Val Leu
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 13

Leu Lys Ser Ile Val Glu Phe
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 14

Ser Lys Val Ile Leu Phe Glu
 1               5

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 15

Cys Gly Thr Ile Val Thr Met Glu Tyr Arg Ile Asp Arg Thr Arg Ser
 1               5                  10                  15

Phe Cys

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 16

Glu Phe Leu Ile Val Lys Ser Val Gly Thr Ile Val Thr Met Glu Tyr
 1               5                  10                  15

Arg Ile Asp Arg Thr Arg Ser Phe Val Glu Phe Leu Ile Val Lys Ser
                20                  25                  30

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
<221> NAME/KEY: SITE

```
<222> LOCATION: (1)..(4)
<223> OTHER INFORMATION: X can be A, V, I, L, W, F, M, and Y.
<221> NAME/KEY: SITE
<222> LOCATION: (5)
<223> OTHER INFORMATION: X can be K, R, D, or E.

<400> SEQUENCE: 17

Xaa Xaa Xaa Xaa Xaa
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 18

Phe Leu Ile Val Lys
 1               5

<210> SEQ ID NO 19
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: X can be D, E, K, or R.
<223> OTHER INFORMATION: Description of Artificial Sequence: Synthetic

<400> SEQUENCE: 19

Xaa Phe Leu Ile Val Lys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 20

Phe Leu Ile Val Lys Ser
 1               5

<210> SEQ ID NO 21
<211> LENGTH: 7
<212> TYPE: PRT
<213> ORGANISM: Artificial Sequence
<220> FEATURE:
<221> NAME/KEY: SITE
<222> LOCATION: (1)
<223> OTHER INFORMATION: x can be Z, E, D, or R.
<223> OTHER INFORMATION: Description of Artificial Sequence: Synthetic

<400> SEQUENCE: 21

Xaa Phe Leu Ile Val Lys Ser
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 22
```

```
Lys Phe Leu Ile Val Lys Ser
  1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:  Synthetic

<400> SEQUENCE: 23

Glu Glu Phe Leu Ile Val Lys Lys Ser
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 24

Val Ser Ile Lys Phe Glu Leu
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 25

Ala Phe Leu Ile Val Lys Ser
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 26

Glu Ala Leu Ile Val Lys Ser
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 27

Glu Phe Ala Ile Val Lys Ser
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 28

Glu Phe Leu Ala Val Lys Ser
```

```
                1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 29

Glu Phe Leu Ile Ala Lys Ser
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 30

Glu Phe Leu Ile Val Ala Ser
  1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 31

Glu Phe Leu Ile Val Lys Ala
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 32

Glu Phe Leu Lys Val Lys Ser
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 33

Ser Lys Val Ile Leu Phe Glu
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 34

Glu Phe Leu Ile Val Glu Ser
  1               5
```

```
<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 35

Val Ser Ile Lys Phe Glu Leu
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 36

Phe Glu Ser Ile Lys Val Leu
  1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 37

Leu Lys Ser Ile Val Glu Phe
  1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic

<400> SEQUENCE: 38

Pro Pro Gly Gly
  1

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 39

Gly Ser Gly Gly Ser
  1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic

<400> SEQUENCE: 40

Gly Gly Gly Ser
  1
```

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (8)..(10)
<223> OTHER INFORMATION: x can be any amino acid and can be of variable
      length.

<400> SEQUENCE: 41

Glu Phe Leu Ile Val Lys Ser Xaa Xaa Xaa Glu Phe Leu Ile Val Lys
  1               5                  10                  15

Ser

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (7)..(9)
<223> OTHER INFORMATION: x can be any amino acid and of variable length.

<400> SEQUENCE: 42

Lys Val Leu Ile Lys Ser Xaa Xaa Xaa Glu Phe Leu Ile Val Glu Ser
  1               5                  10                  15

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (8)..(10)
<223> OTHER INFORMATION: x can be any amino acid and can be of variable
      length.

<400> SEQUENCE: 43

Val Ser Ile Lys Phe Glu Leu Xaa Xaa Xaa Val Ser Ile Lys Phe Glu
  1               5                  10                  15

Leu

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (6)..(8)
<223> OTHER INFORMATION: x can be any amino acid and can be of variable
      length.

<400> SEQUENCE: 44

Leu Ile Val Lys Ser Xaa Xaa Xaa Leu Ile Val Lys Ser
  1               5                  10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
<221> NAME/KEY: SITE

```
<222> LOCATION: (7)..(9)
<223> OTHER INFORMATION: x can be any amino acid and can be of variable
      length.

<400> SEQUENCE: 45

Glu Phe Leu Ile Val Lys Xaa Xaa Xaa Glu Phe Leu Ile Val Lys
 1               5                  10                  15

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (8)..(10)
<223> OTHER INFORMATION: x can be any amino acid and can be of variable
      length.

<400> SEQUENCE: 46

Phe Glu Ser Ile Lys Val Leu Xaa Xaa Xaa Phe Glu Ser Ile Lys Val
 1               5                  10                  15

Leu

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (8)..(10)
<223> OTHER INFORMATION: x can be any amino acid and can be of variable
      length.

<400> SEQUENCE: 47

Leu Lys Ser Ile Val Glu Phe Xaa Xaa Xaa Leu Lys Ser Ile Val Glu
 1               5                  10                  15

Phe

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic

<400> SEQUENCE: 48

Glu Phe Leu Ile Lys Ser Val Gly Thr Ile Val Thr Met Glu Tyr Arg
 1               5                  10                  15

Ile Asp Arg Thr Arg Ser Phe Val Glu Phe Leu Ile Phe Lys Ser
            20                  25                  30

<210> SEQ ID NO 49
<211> LENGTH: 18
<212> TYPE: PRT
<213> ORGANISM: Barley

<400> SEQUENCE: 49

Val Gly Thr Ile Val Thr Met Glu Tyr Arg Ile Asp Arg Thr Arg Ser
 1               5                  10                  15

Phe Val

<210> SEQ ID NO 50
<211> LENGTH: 31
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 50

Glu Phe Leu Ile Lys Ser Val Gly Thr Ile Val Thr Met Glu Tyr Arg
 1               5                  10                  15

Ile Asp Arg Thr Arg Ser Phe Val Ser Lys Val Ile Leu Phe Glu
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 51

Ser Lys Val Ile Leu Phe Glu Val Gly Thr Ile Val Thr Met Glu Tyr
 1               5                  10                  15

Arg Ile Asp Arg Thr Arg Ser Phe Val Glu Phe Leu Ile Val Lys Ser
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 52

Ser Lys Val Ile Leu Phe Glu Val Gly Thr Ile Val Thr Met Glu Tyr
 1               5                  10                  15

Arg Ile Asp Arg Thr Arg Ser Phe Val Ser Lys Val Ile Leu Phe Glu
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 53

Lys Phe Leu Ile Val Lys Ser Val Gly Thr Ile Val Thr Met Glu Tyr
 1               5                  10                  15

Arg Ile Asp Arg Thr Arg Ser Phe Val Lys Phe Leu Ile Val Lys Ser
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic

<400> SEQUENCE: 54

Lys Phe Leu Ile Val Lys Ser Val Gly Thr Ile Val Met Glu Tyr Arg
 1               5                  10                  15

Ile Asp Arg Thr Arg Ser Phe Val Glu Phe Leu Ile Val Glu Ser
            20                  25                  30

<210> SEQ ID NO 55
```

<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 55

Glu Phe Leu Ile Val Glu Ser Val Gly Thr Ile Val Thr Met Glu Tyr
 1               5                  10                  15

Arg Ile Asp Arg Thr Arg Ser Phe Val Glu Phe Leu Ile Val Glu Ser
            20                  25                  30

<210> SEQ ID NO 56
<211> LENGTH: 33
<212> TYPE: PRT
<213> ORGANISM: Artificial Sequence
<220> FEATURE:
<223> OTHER INFORMATION: Description of Artificial Sequence: Synthetic

<400> SEQUENCE: 56

Glu Lys Leu Ile Lys Val Lys Ser Val Gly Thr Ile Val Thr Met Glu
 1               5                  10                  15

Tyr Arg Ile Asp Arg Thr Arg Ser Phe Val Glu Lys Leu Lys Val Lys
            20                  25                  30

Ser

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 57

Glu Ser Leu Ser Val Lys Ser Val Gly Thr Ile Val Thr Met Glu Tyr
 1               5                  10                  15

Arg Ile Asp Arg Thr Arg Ser Phe Val Glu Ser Leu Ser Val Lys Ser
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 58

Glu Phe Leu Lys Val Lys Ser Val Gly Thr Ile Val Thr Met Glu Tyr
 1               5                  10                  15

Arg Ile Asp Arg Thr Arg Ser Phe Val Glu Phe Leu Lys Val Lys Ser
            20                  25                  30

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic

<400> SEQUENCE: 59

Glu Glu Phe Leu Ile Val Lys Lys Ser Val Gly Thr Ile Val Thr Met
 1               5                  10                  15

Glu Tyr Arg Ile Asp Arg Thr Arg Ser Phe Val Glu Glu Phe Leu Ile
            20                  25                  30

Val Lys Lys Ser
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic

<400> SEQUENCE: 60

Met Gly Glu Phe Leu Ile Val Lys Ser Val Gly Thr Ile Val Thr Met
 1               5                  10                  15

Glu Tyr Arg Ile Asp Arg Thr Arg Ser Phe Val Glu Phe Leu Ile Val
            20                  25                  30

Lys Ser Gly Pro Pro
        35

<210> SEQ ID NO 61
<211> LENGTH: 42
<212> TYPE: PRT
<213> ORGANISM: Artificial Sequence
<220> FEATURE:
<223> OTHER INFORMATION: Description of Artificial Sequence: Synthetic

<400> SEQUENCE: 61

Lys Lys Lys Lys Lys Lys Gly Gly Gly Gly Glu Phe Leu Ile Val Lys
 1               5                  10                  15

Ser Val Gly Thr Ile Val Thr Met Glu Tyr Arg Ile Asp Arg Thr Arg
            20                  25                  30

Ser Phe Val Glu Phe Leu Ile Val Lys Ser
        35                  40

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 62

Lys Lys Lys Lys Lys Lys Gly Gly Gly Gly
 1               5                  10

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence: Synthetic

<400> SEQUENCE: 63

Lys Lys Lys Gly Ser Gly Ser Glu Phe Leu Ile Val Lys Ser Val Gly
 1               5                  10                  15

Thr Ile Val Thr Met Glu Tyr Arg Ile Asp Arg Thr Arg Ser Phe Val
            20                  25                  30

Glu Phe Leu Ile Val Lys Ser
        35

<210> SEQ ID NO 64
<211> LENGTH: 7
<212> TYPE: PRT
<213> ORGANISM: Artificial Sequence

```
<220> FEATURE:
<223> OTHER INFORMATION: Description of Artificial Sequence: Synthetic

<400> SEQUENCE: 64

Lys Lys Lys Gly Ser Gly Ser
  1               5

<210> SEQ ID NO 65
<211> LENGTH: 23
<212> TYPE: PRT
<213> ORGANISM: Artificial Sequence
<220> FEATURE:
<223> OTHER INFORMATION: Description of Artificial Sequence: Synthetic

<400> SEQUENCE: 65

Glu Phe Leu Ile Val Lys Ser Ser Thr Lys Ser Ile Pro Pro Gln Ser
  1               5                  10                  15

Glu Phe Leu Ile Val Lys Ser
            20

<210> SEQ ID NO 66
<211> LENGTH: 35
<212> TYPE: PRT
<213> ORGANISM: Artificial Sequence
<220> FEATURE:
<223> OTHER INFORMATION: Description of Artificial Sequence: Synthetic

<400> SEQUENCE: 66

Met Gly Glu Phe Leu Ile Val Lys Ser Gly Gly Gly Asp Tyr Lys
  1               5                  10                  15

Asp Asp Asp Asp Lys Gly Gly Gly Gly Glu Phe Leu Ile Val Lys Ser
            20                  25                  30

Gly Pro Pro
        35

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 67

Asp Tyr Lys Asp Asp Asp Asp Lys
  1               5

<210> SEQ ID NO 68
<211> LENGTH: 38
<212> TYPE: PRT
<213> ORGANISM: Artificial Sequence
<220> FEATURE:
<223> OTHER INFORMATION: Description of Artificial Sequence: Synthetic

<400> SEQUENCE: 68

Met Gly Glu Phe Leu Ile Val Lys Ser Gly Gly Gly Gly Tyr Pro Tyr
  1               5                  10                  15

Asp Val Pro Asp Tyr Ala Ser Leu Gly Gly Gly Gly Glu Phe Leu Ile
            20                  25                  30

Val Lys Ser Gly Pro Pro
        35

<210> SEQ ID NO 69
<211> LENGTH: 11
<212> TYPE: PRT
```

-continued

```
<213> ORGANISM: Influenza virus

<400> SEQUENCE: 69

Tyr Pro Tyr Asp Val Pro Asp Tyr Ala Ser Leu
  1               5                   10

<210> SEQ ID NO 70
<211> LENGTH: 7
<212> TYPE: PRT
<213> ORGANISM: monkey virus

<400> SEQUENCE: 70

Pro Lys Lys Lys Arg Lys Val
  1               5

<210> SEQ ID NO 71
<211> LENGTH: 6
<212> TYPE: PRT
<213> ORGANISM: Homo sapiens

<400> SEQUENCE: 71

Ala Arg Arg Arg Arg Pro
  1               5

<210> SEQ ID NO 72
<211> LENGTH: 10
<212> TYPE: PRT
<213> ORGANISM: Homo sapiens

<400> SEQUENCE: 72

Glu Glu Val Gln Arg Lys Arg Gln Lys Leu
  1               5                   10

<210> SEQ ID NO 73
<211> LENGTH: 9
<212> TYPE: PRT
<213> ORGANISM: Homo sapiens

<400> SEQUENCE: 73

Glu Glu Lys Arg Lys Arg Thr Tyr Glu
  1               5

<210> SEQ ID NO 74
<211> LENGTH: 20
<212> TYPE: PRT
<213> ORGANISM: Xenopus laevis

<400> SEQUENCE: 74

Ala Val Lys Arg Pro Ala Ala Thr Lys Lys Ala Gly Gln Ala Lys Lys
  1               5                   10                  15

Lys Lys Leu Asp
             20

<210> SEQ ID NO 75
<211> LENGTH: 31
<212> TYPE: PRT
<213> ORGANISM: Homo sapiens

<400> SEQUENCE: 75

Met Ala Ser Pro Leu Thr Arg Phe Leu Ser Leu Asn Leu Leu Leu Leu
  1               5                   10                  15

Gly Glu Ser Ile Leu Gly Ser Gly Glu Ala Lys Pro Gln Ala Pro
             20                  25                  30
```

<210> SEQ ID NO 76
<211> LENGTH: 21
<212> TYPE: PRT
<213> ORGANISM: Homo sapiens

<400> SEQUENCE: 76

Met Ser Ser Phe Gly Tyr Arg Thr Leu Thr Val Ala Leu Phe Thr Leu
 1               5                  10                  15

Ile Cys Cys Pro Gly
            20

<210> SEQ ID NO 77
<211> LENGTH: 51
<212> TYPE: PRT
<213> ORGANISM: Homo sapiens

<400> SEQUENCE: 77

Pro Gln Arg Pro Glu Asp Cys Arg Pro Arg Gly Ser Val Lys Gly Thr
 1               5                  10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
        35                  40                  45

His Ser Arg
    50

<210> SEQ ID NO 78
<211> LENGTH: 33
<212> TYPE: PRT
<213> ORGANISM: Homo sapiens

<400> SEQUENCE: 78

Met Val Ile Ile Val Thr Val Val Ser Val Leu Leu Ser Leu Phe Val
 1               5                  10                  15

Thr Ser Val Leu Leu Cys Phe Ile Phe Gly Gln His Leu Arg Gln Gln
            20                  25                  30

Arg

<210> SEQ ID NO 79
<211> LENGTH: 37
<212> TYPE: PRT
<213> ORGANISM: Homo sapiens

<400> SEQUENCE: 79

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 80
<211> LENGTH: 14
<212> TYPE: PRT
<213> ORGANISM: Chicken virus

<400> SEQUENCE: 80

Met Gly Ser Ser Lys Ser Lys Pro Lys Asp Pro Ser Gln Arg
 1               5                  10

```
<210> SEQ ID NO 81
<211> LENGTH: 26
<212> TYPE: PRT
<213> ORGANISM: Homo sapiens

<400> SEQUENCE: 81

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 82
<211> LENGTH: 20
<212> TYPE: PRT
<213> ORGANISM: Unknown
<220> FEATURE:
<223> OTHER INFORMATION: Description of Unknown Organism: from rhodopsin

<400> SEQUENCE: 82

Lys Gln Phe Arg Asn Cys Met Leu Thr Ser Leu Cys Cys Gly Lys Asn
1               5                   10                  15

Pro Leu Gly Asp
            20

<210> SEQ ID NO 83
<211> LENGTH: 19
<212> TYPE: PRT
<213> ORGANISM: Homo sapiens

<400> SEQUENCE: 83

Leu Asn Pro Pro Asp Glu Ser Gly Pro Gly Cys Met Ser Cys Lys Cys
1               5                   10                  15

Val Leu Ser

<210> SEQ ID NO 84
<211> LENGTH: 36
<212> TYPE: PRT
<213> ORGANISM: Unknown
<220> FEATURE:
<223> OTHER INFORMATION: Description of Unknown Organism: lysosomal
      membrane sequences from Lamp-1

<400> SEQUENCE: 84

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35

<210> SEQ ID NO 85
<211> LENGTH: 35
<212> TYPE: PRT
<213> ORGANISM: Unknown
<220> FEATURE:
<223> OTHER INFORMATION: Description of Unknown Organism: lysosomal
      membrane sequences from Lamp-2

<400> SEQUENCE: 85

Leu Val Pro Ile Ala Val Gly Ala Ala Leu Ala Gly Val Leu Ile Leu
1               5                   10                  15

Val Leu Leu Ala Tyr Phe Ile Gly Leu Lys His His His Ala Gly Tyr
            20                  25                  30
```

Glu Gln Phe
      35

<210> SEQ ID NO 86
<211> LENGTH: 27
<212> TYPE: PRT
<213> ORGANISM: yeast

<400> SEQUENCE: 86

Met Leu Arg Thr Ser Ser Leu Phe Thr Arg Arg Val Gln Pro Ser Leu
 1               5                  10                  15

Phe Ser Arg Asn Ile Leu Arg Leu Gln Ser Thr
             20                  25

<210> SEQ ID NO 87
<211> LENGTH: 25
<212> TYPE: PRT
<213> ORGANISM: yeast

<400> SEQUENCE: 87

Met Leu Ser Leu Arg Gln Ser Ile Arg Phe Phe Lys Pro Ala Thr Arg
 1               5                  10                  15

Thr Leu Cys Ser Ser Arg Tyr Leu Leu
             20                  25

<210> SEQ ID NO 88
<211> LENGTH: 64
<212> TYPE: PRT
<213> ORGANISM: yeast

<400> SEQUENCE: 88

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
             20                  25                  30

Thr Gln Lys Leu Val Thr Ala Gly Val Ala Ala Ala Gly Ile Thr Ala
         35                  40                  45

Ser Thr Leu Leu Tyr Ala Asp Ser Leu Thr Ala Glu Ala Met Thr Ala
     50                  55                  60

<210> SEQ ID NO 89
<211> LENGTH: 41
<212> TYPE: PRT
<213> ORGANISM: yeast

<400> SEQUENCE: 89

Met Lys Ser Phe Ile Thr Arg Asn Lys Thr Ala Ile Leu Ala Thr Val
 1               5                  10                  15

Ala Ala Thr Gly Thr Ala Ile Gly Ala Tyr Tyr Tyr Tyr Asn Gln Leu
             20                  25                  30

Gln Gln Gln Gln Gln Arg Gly Lys Lys
         35                  40

<210> SEQ ID NO 90
<211> LENGTH: 4
<212> TYPE: PRT
<213> ORGANISM: Unknown
<220> FEATURE:
<223> OTHER INFORMATION: Description of Unknown Organism: sequence
      derived from calreticulin

<400> SEQUENCE: 90

Lys Asp Glu Leu
 1

<210> SEQ ID NO 91
<211> LENGTH: 15
<212> TYPE: PRT
<213> ORGANISM: adenovirus

<400> SEQUENCE: 91

Leu Tyr Leu Ser Arg Arg Ser Phe Ile Asp Glu Lys Lys Met Pro
 1               5                  10                  15

<210> SEQ ID NO 92
<211> LENGTH: 19
<212> TYPE: PRT
<213> ORGANISM: Homo sapiens

<400> SEQUENCE: 92

Leu Asn Pro Pro Asp Glu Ser Gly Pro Gly Cys Met Ser Cys Lys Cys
 1               5                  10                  15

Val Leu Ser

<210> SEQ ID NO 93
<211> LENGTH: 15
<212> TYPE: PRT
<213> ORGANISM: Unknown
<220> FEATURE:
<223> OTHER INFORMATION: Description of Unknown Organism:
      geranylgeranylation sequences

<400> SEQUENCE: 93

Leu Thr Glu Pro Thr Gln Pro Thr Arg Asn Gln Cys Cys Ser Asn
 1               5                  10                  15

<210> SEQ ID NO 94
<211> LENGTH: 9
<212> TYPE: PRT
<213> ORGANISM: Unknown
<220> FEATURE:
<223> OTHER INFORMATION: Description of Unknown Organism: destruction
      sequence

<400> SEQUENCE: 94

Arg Thr Ala Leu Gly Asp Ile Gly Asn
 1               5

<210> SEQ ID NO 95
<211> LENGTH: 20
<212> TYPE: PRT
<213> ORGANISM: Homo sapiens

<400> SEQUENCE: 95

Met Tyr Arg Met Gln Leu Leu Ser Cys Ile Ala Leu Ser Leu Ala Leu
 1               5                  10                  15

Val Thr Asn Ser
            20

<210> SEQ ID NO 96
<211> LENGTH: 29
<212> TYPE: PRT
<213> ORGANISM: Homo sapiens

<400> SEQUENCE: 96

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr
            20                  25

<210> SEQ ID NO 97
<211> LENGTH: 27
<212> TYPE: PRT
<213> ORGANISM: Homo sapiens

<400> SEQUENCE: 97

Met Ala Leu Trp Met Arg Leu Leu Pro Leu Leu Ala Leu Leu Ala Leu
  1               5                  10                  15

Trp Gly Pro Asp Pro Ala Ala Ala Phe Val Asn
            20                  25

<210> SEQ ID NO 98
<211> LENGTH: 18
<212> TYPE: PRT
<213> ORGANISM: Influenza virus

<400> SEQUENCE: 98

Met Lys Ala Lys Leu Leu Val Leu Leu Tyr Ala Phe Val Ala Gly Asp
  1               5                  10                  15

Gln Ile

<210> SEQ ID NO 99
<211> LENGTH: 24
<212> TYPE: PRT
<213> ORGANISM: Homo sapiens

<400> SEQUENCE: 99

Met Gly Leu Thr Ser Gln Leu Leu Pro Pro Leu Phe Phe Leu Leu Ala
  1               5                  10                  15

Cys Ala Gly Asn Phe Val His Gly
            20

<210> SEQ ID NO 100
<211> LENGTH: 10
<212> TYPE: PRT
<213> ORGANISM: Artificial Sequence
<220> FEATURE:
<221> NAME/KEY: SITE
<222> LOCATION: (3)..(6)
<223> OTHER INFORMATION: x can be any amino acid
<223> OTHER INFORMATION: Description of Artificial Sequence: Synthetic

<400> SEQUENCE: 100

Met Gly Xaa Xaa Xaa Xaa Gly Gly Pro Pro
  1               5                  10

<210> SEQ ID NO 101
<211> LENGTH: 9
<212> TYPE: PRT
<213> ORGANISM: Artificial Sequence
<220> FEATURE:
<221> NAME/KEY: SITE
<222> LOCATION: (3)..(6)
<223> OTHER INFORMATION: x can be any amino acid
<223> OTHER INFORMATION: Description of Artificial Sequence: Synthetic

<400> SEQUENCE: 101

Met Gly Xaa Xaa Xaa Xaa Gly Pro Pro
  1               5

<210> SEQ ID NO 102

```
<211> LENGTH: 11
<212> TYPE: PRT
<213> ORGANISM: Artificial Sequence
<220> FEATURE:
<221> NAME/KEY: SITE
<222> LOCATION: (4)..(7)
<223> OTHER INFORMATION: x can be any amino acid
<223> OTHER INFORMATION: Description of Artificial Sequence: Synthetic

<400> SEQUENCE: 102

Met Gly Gly Xaa Xaa Xaa Xaa Gly Gly Pro Pro
 1               5                  10

<210> SEQ ID NO 103
<211> LENGTH: 10
<212> TYPE: PRT
<213> ORGANISM: Artificial Sequence
<220> FEATURE:
<221> NAME/KEY: SITE
<222> LOCATION: (4)..(7)
<223> OTHER INFORMATION: x can be any amino acid
<223> OTHER INFORMATION: Description of Artificial Sequence: Synthetic

<400> SEQUENCE: 103

Met Gly Gly Xaa Xaa Xaa Xaa Gly Pro Pro
 1               5                  10

<210> SEQ ID NO 104
<211> LENGTH: 27
<212> TYPE: PRT
<213> ORGANISM: Artificial Sequence
<220> FEATURE:
<221> NAME/KEY: SITE
<222> LOCATION: (18)..(20)
<223> OTHER INFORMATION: x can be any amino acid
<223> OTHER INFORMATION: Description of Artificial Sequence: Synthetic

<400> SEQUENCE: 104

Lys Lys Lys Lys Lys Lys Gly Gly Gly Gly Glu Phe Leu Ile Val Lys
 1               5                  10                  15

Ser Xaa Xaa Xaa Glu Phe Leu Ile Val Lys Ser
             20                  25

<210> SEQ ID NO 105
<211> LENGTH: 4
<212> TYPE: DNA
<213> ORGANISM: Unknown
<220> FEATURE:
<223> OTHER INFORMATION: Description of Unknown Organism: promoter
      sequence

<400> SEQUENCE: 105 caat                                                                    4

<210> SEQ ID NO 106
<211> LENGTH: 4
<212> TYPE: DNA
<213> ORGANISM: Unknown
<220> FEATURE:
<223> OTHER INFORMATION: Description of Unknown Organism: promoter
      sequence

<400> SEQUENCE: 106 tata                                                                    4

<210> SEQ ID NO 107
<211> LENGTH: 6
<212> TYPE: DNA
```

```
<213> ORGANISM: Unknown
<220> FEATURE:
<223> OTHER INFORMATION: Description of Unknown Organism: mRNA
      polyadenylation sequence

<400> SEQUENCE: 107 aataaa                                                                    6

<210> SEQ ID NO 108
<211> LENGTH: 7
<212> TYPE: DNA
<213> ORGANISM: Unknown
<220> FEATURE:
<221> NAME/KEY: misc_difference
<222> LOCATION: (1)..(3)
<223> OTHER INFORMATION: n can be any amino acid.
<223> OTHER INFORMATION: Description of Unknown Organism: Kozak
      consensus sequence.

<400> SEQUENCE: 108 nnnatgg                                                                   7

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic

<400> SEQUENCE: 109

Glu Phe Leu Ile Val Lys Ser Ser Thr Lys Ser Ile Pro Pro Gln Ser
 1               5                  10                  15

Glu Phe Leu Ile Val Lys Ser
            20

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 110

Glu Phe Leu Ile Val Lys Ser Val Gly Thr Ile Val Thr Met Glu Tyr
 1               5                  10                  15

Arg Ile Asp Arg Thr Arg Ser Phe Val Ser Lys Val Ile Leu Phe Glu
            20                  25                  30

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 111

Cys Gly Thr Ile Val Thr Met Glu Tyr
 1               5

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 112
```

```
Glu Phe Leu Ile Val Lys Ser Val Gly Thr Ile Val Thr Met Glu Tyr
 1               5                  10                  15
```

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 113

```
Arg Ile Asp Arg Thr Arg Ser Phe
 1               5
```

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 114

```
Arg Ile Asp Arg Thr Arg Ser Phe Val Glu Phe Leu Ile Val Lys Ser
 1               5                  10                  15
```

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 115

```
Arg Ile Asp Arg Thr Arg Ser Phe Cys
 1               5
```

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 116

```
Glu Phe Leu Ile Val
 1               5
```

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 117

```
Val Glu Phe Leu Ile
 1               5
```

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic

<400> SEQUENCE: 118

Cys Gly Thr Ile Val Thr Met Glu Tyr Arg Ile Asp Arg Thr Arg Ser
 1               5                  10                  15
Phe

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 119

Cys Gly Thr Ile Val Thr Met Glu Tyr Arg Ile Asp Arg Thr
 1               5                  10

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 120

Glu Tyr Arg Ile Asp Arg Thr
 1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 121

Arg Ser Phe Val Glu Phe
 1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 122

Cys Gly Thr Ile Val Thr Met
 1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 123

Lys Ser Val Gly Thr Ile Val Thr Met
 1               5

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 124

```
Glu Tyr Arg Ile Asp Arg Thr Arg Ser Phe Cys
  1               5                  10
```

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 125

```
Val Thr Met Glu Tyr Arg Ile Asp Arg Thr Arg Ser Phe
  1               5                  10
```

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 126

```
Met Glu Tyr Arg Ile Asp Arg Thr Arg Ser Phe Cys
  1               5                  10
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 127

```
Met Glu Tyr Arg Ile Asp Arg Thr
  1               5
```

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 128

```
Thr Ile Met Glu Tyr Arg Ile Asp Arg Thr
  1               5                  10
```

<210> SEQ ID NO 129
<211> LENGTH: 31
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (15)..(17)
<223> OTHER INFORMATION: x can be any amino acid and be of variable
      length.

<400> SEQUENCE: 129

```
Lys Lys Lys Gly Ser Gly Ser Glu Phe Leu Ile Val Lys Ser Xaa Xaa
  1               5                  10                  15

Xaa Glu Phe Leu Ile Val Lys Ser Gly Ser Gly Ser Lys Lys Lys
               20                  25                  30
```

<210> SEQ ID NO 130
<211> LENGTH: 37

<212> TYPE: PRT
<213> ORGANISM: Artificial Sequence
<220> FEATURE:
<223> OTHER INFORMATION: Description of Artificial Sequence: Synthetic

<400> SEQUENCE: 130

Met Gly Glu Phe Leu Ile Val Lys Ser Gly Gly Gly Tyr Pro Tyr
 1               5                  10                  15

Asp Val Pro Asp Tyr Ala Ser Leu Gly Gly Glu Phe Leu Ile Val
            20                  25                  30

Lys Ser Gly Pro Pro
        35

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 131

Ser Thr Lys Ser Ile Pro Pro Gln Ser
 1               5

<210> SEQ ID NO 132
<211> LENGTH: 9
<212> TYPE: PRT
<213> ORGANISM: Unknown
<220> FEATURE:
<223> OTHER INFORMATION: Description of Unknown Organism: protease
      inhibitor

<400> SEQUENCE: 132

Cys Thr Lys Ser Ile Pro Pro Gln Cys
 1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 133

Met Gly Glu Phe Leu Ile Val Lys Ser
 1               5

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 134

Glu Phe Leu Ile Val Lys Ser Gly Pro Pro
 1               5                  10

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 135

Gly Gly Gly Gly Asp Tyr Lys Asp Asp Asp Lys Gly Gly Gly Gly
1               5                   10                  15

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Synthetic

<400> SEQUENCE: 136

Gly Gly Gly Gly Tyr Pro Tyr Asp Val Pro Asp Tyr Ala Ser Leu Gly
1               5                   10                  15

Gly Gly

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
<221> NAME/KEY: SITE
<222> LOCATION: (1)
<223> OTHER INFORMATION: x can be E, D, K, or R.
<221> NAME/KEY: SITE
<222> LOCATION: (6)
<223> OTHER INFORMATION: x can be E, D, K, or R.

<400> SEQUENCE: 137

Xaa Phe Leu Ile Val Xaa
1               5

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 138

Glu Tyr Arg Ile Asp Arg Thr Arg Ser Phe
1               5                   10

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: synthetic

<400> SEQUENCE: 139

Cys Gly Thr Ile Val Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 140

Thr Ile Val Thr Met Glu Tyr Arg
1               5

<210> SEQ ID NO 141
<211> LENGTH: 13

```
<212> TYPE: PRT
<213> ORGANISM: Artificial Sequence
<220> FEATURE:
<223> OTHER INFORMATION: Description of Artificial Sequence: Synthetic

<400> SEQUENCE: 141

Thr Met Glu Tyr Arg Ile Asp Arg Thr Arg Ser Phe Cys
 1               5                  10

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 142

Cys Gly Thr Ile Val
 1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 143

Ser Val Gly Thr Ile
 1               5

<210> SEQ ID NO 144
<211> LENGTH: 27
<212> TYPE: PRT
<213> ORGANISM: Artificial Sequence
<220> FEATURE:
<223> OTHER INFORMATION: Description of Artificial Sequence: synthetic

<400> SEQUENCE: 144

Glu Phe Leu Ile Val Lys Ser Val Gly Thr Ile Val Thr Met Glu Tyr
 1               5                  10                  15

Arg Ile Asp Arg Thr Arg Ser Phe Val Glu Phe
             20                  25

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic

<400> SEQUENCE: 145

Glu Phe Leu Ile Val Lys Ser Val Gly Thr Ile Val Thr Met Glu Tyr
 1               5                  10                  15

Arg Ile Asp Arg Thr
             20

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 146

Ser Phe Val Glu Phe Leu Ile Val
```

-continued

```
<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 147

Phe Val Glu Phe Leu Ile Val
  1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 148

Ser Phe Val Glu Phe
  1               5

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 149

Ser Phe Val Glu Phe Leu Ile Val Lys Ser
  1               5                  10

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 150

Lys Phe Glu Arg Gln
  1               5
```

PEPTIDES CAUSING FORMATION OF COMPACT STRUCTURES

This application claims the benefit of provisional application ser. No. 60/080,444 filed Apr. 2, 1998.

FIELD OF THE INVENTION the compositions and methods of the invention relate to the use of dimerization peptides that self-associate and their use with other proteins to effect the formation of compact structures.

BACKGROUND OF THE INVENTION

Proteins interact with each other largely through conformationally constrained domains. Although linear peptides with freely rotating amino and carboxyl termini can have potent functions as is known in the art, the conversion of such peptide structures into pharmacologic agents is frequently difficult. Therefore the presentation of peptides in conformationally constrained structures can result in the generation of pharmaceuticals with high affinity to its target protein. Constrained peptides have many valuable features compared to their linear analogs. These include: (i) enhanced stability to proteolysis [Szewczuk et al., Biochemistry 31:9132–9140 (1992)) due to the lack of unconstrained N- or C-terminal amino acid residues accessible to amino- or carboxypeptidases and a non-extended structure which diminishes endopeptidase susceptibility; (ii) a restricted conformation space that can result in a higher binding affinity for cognate binding proteins due to a reduced entropic cost of binding [Hruby, Life Sci., 31:189–199 (1982); Rizo and Gierasch, Ann. Rev. Biochem. 61:387–418 (1992)]; (iii) the geometry to mimic reverse turns, loops or other secondary structures [Rose et al., Adv. Proptein Chem., 37:1–109 (1985); Stradley et al., Biopolymers 29:263–287 (1990); Rizo et al., in *Molecular Conformation and Biological Interactions* (P. Balaram and S. Ramaseshan, eds.), Indian Academy of Sciences Publications (Bangalore, India), p 469–496 (1991)]; and (iv) a conformationally restricted scaffold which allows easier pharmaophore and drug development.

Thus constrained peptides can form the basis for the isolation of new ligands and receptors and subsequently for the rational design of small molecules which may be useful as drugs. The desirability of this approach was shown using cyclic peptide libraries which have been used to discover and refine potent ligands of a variety of receptors [O'Neil et al., Proteins: Structure Function and Genetics 14:509–515 (1992); Giebel et al., Biochem. 34:15430–35 (1995); Spatola and Crozet, J. Med. Chem. 39:3842–46 (1996); Koivunen et al., J. Biol. Chem. 268:20205–10 (1993); Koivunen et al., J. Cell. Biol. 124:373–380 (1994)], enzymes [McBride et al., J. Mol. Biol. 259:819–27 (1996); Eichler et al., Mol. Divers. 1:233–240 (1996)], and other proteins [Wang et al., J. Biol. Chem. 270:2323942 (1995)].

Several constrained protein scaffolds, capable of presenting a protein of interest as a conformationally-restricted domain are described in the literature and include minibody structures (Bianchi et al., J. Mol. Biol. 236(2):649–59 (1994), loops on beta-sheet turns, coiled-coil stem structures (Myszka and Chaiken, Biochemistry 33:2363–2372 (1994), zinc-finger domains, cysteine-linked (disulfide) structures, transglutaminase linked structures, cyclic peptides, helical barrels or bundles, leucine zipper motifs (Martin et al., EMBO J. 13(22):5303–5309 (1994); O'Shea et al., Science 243:53842 (1993), etc.

In addition, self-aggregation has been described for regulatory peptides such as the neuropeptide head activator [as further outlined below; Bodenmuller et al., EMBO J. 5(8):1825–1829 (1986)], substance P [Poujade et al., Biochem. Biophys. Res. Commun. 114:1109–1116(1983)], metenkephalin [Mastropaolo et al., Biochem. Biophys. Res. Commun. 134:698–703 (1986)], and neuropeptide Y [Minakata et al., J. Biol. Chem. 264:7907–7913 (1989)].

Pertinent to the subject of this invention is a peptide derived from the neuropeptide head activator (HA) isolated from the freshwater coelenterate *Hydra* (Bodenmuller et al., supra). Bodenmuller et at. demonstrated that under physiological conditions the HA peptide (pEPPGGSKVILF) dimerizes to form a biologically inactive molecule.

Dimerization of the monomer form yields a stable structure, which does not dissociate into its monomeric components at concentrations as low as $10^{-13}$ M. Further analysis of HA fragments revealed that a fragment containing only the last six amino acid residues from the carboxy terminus of the HA peptide (pSKVILF) dimerized more efficiently that HA itself. However, a fragment containing only the last 4 amino acid residues (pVILF) and a fragment derived from the amino-terminal end of HA (pEPPGGSK) did not lead to dimer formation. Most importantly, their analysis showed that both the replacement of the carboxy-terminal phenylalanine and a modification thereof (e.g., introduction of an iodine in the para (4') position of the aromatic ring) abolished dimerization completely or decreased dimerization tendency drastically.

Aldwin et al. (U.S. Pat. No. 5,491,074), referring to SKVILF as 'association peptide', added additional amino acid residues at either its amino terminal sequence or to its carboxy-terminus and found that some of the resulting proteins could form dimeric peptides. However, Aldwin et al. did not demonstrate or anticipate the addition of more than one 'association peptide' to one polypetide of interest. Accordingly, it is an object of the invention to provide dimerization peptides for use in a variety of applications.

SUMMARY OF THE INVENTION

Peptides which have a moderate or high affinity for each other, when added as extensions to both the N- and C-terminus of a protein, can be used to help fold the protein into a compact structure. Compared to cognate linear proteins and disulfide-cyclized proteins, this new compact structure is more stable to cellular and other proteases, and is significantly more conformationally constrained than the linear peptides. The compact structure can have other functional sequences embedded within its sequence, and is preferable to linear and less constrained peptides for intracellular and extracellular library screens, and for targeting to specific intracellular locations. It can be used, with appropriate flanking residues on each end of the varied residues in a random peptide sequence, to create structurally-biased peptide libraries. By virtue of its stability and constraints, this scaffold can prolong the activity of any embedded peptide sequences in the presence of proteases.

Peptides having the property of self-aggregating herein are referred to as dimerization peptides (DP). The dimerization peptides of this invention comprise the sequence FLIVK (from amino-terminal to carboxy-terminal). Examples of dimerization sequences which enhance the folding of a protein of interest include, but are not limited to, FLIVK, EFLIVKS, KFVLIKS, VSIKFEL, LIVKS, EFLIVK, KFLIVK, FESIKVL, and LKSIVEF. These dimerization peptides (DP) can be used in several combinations to yield proteins of the general structure 'DP-protein' or 'DP-protein-DP' wherein 'DP' is a dimerization peptide, 'protein' comprises at least two amino acid residues. In addition other amino acid sequences including, but not limited to, linker sequences, tag sequences, targeting sequences and stabilization sequences are generally included.

Other sequences include those with a high content of hydrophobic amino acids and 1 or 2 charged residue side chains. Generally, a sequence at each terminus of the dimerization peptide composed of 5, 6, 7 and 8 amino acids with at least 34 highly hydrophobic residues (taken from F, I, L, M, V, W, and Y) will function in this fashion.

The compositions of this invention are displayed intracellularly or extracellulary and are useful to identify binding proteins and molecules and to modulate intracellular signaling pathways. In one aspect of the invention, a library of constrained proteins is evaluated in vivo for its bioactive potential. Thus, the invention accesses molecules or targets within living cells and provides for the isolation of the constrained protein which has a phenotypic effect on this living cell. This method comprises the steps of a) introducing a library encoding constrained proteins into a plurality of cells; and b) screening the plurality of cells for an altered phenotype, conferred upon the cell by a member of the library. The methods may also include the steps of c) isolating cell(s) exhibiting an altered phenotype and d) isolating the member of the library which caused an altered phenotype.

In another aspect, the compositions of the invention are useful to identify in vitro binding proteins and other small molecules capable of binding to the constrained protein. This method comprises the steps of a) providing a constrained protein of interest; b) binding the constrained protein of interest to a solid support; c) providing a molecular library comprising a plurality of individual members; and d) providing conditions allowing the individual members to bind to the constrained protein of interest. The method may also include the steps of e) isolating the bound library member.

In another aspect, the invention provides for the construction of molecular libraries comprising a plurality of constrained proteins. This library of constrained proteins is used in vitro binding assays to identify individual members capable of binding to a protein of interest. This method comprises the steps of a) providing a protein of interest; b) binding the protein of interest to a solid support; c) providing a molecular library comprising a plurality of constrained proteins; and d) providing conditions allowing the constrained proteins to bind to the protein of interest. The method may also include the steps of e) isolating the bound constrained protein.

The compositions of the invention are thus useful as a scaffold for gene therapy and for potential use as a therapeutic in physiological fluids.

In an additional aspect of the invention, the constrained peptides are linked to fusion partners or are targeted to specific subcellular compartments.

The present invention also provides molecular libraries encoding constrained proteins, comprising plasmids and retroviral components and host cells comprising these molecular libraries.

BRIEF DESCRIPTION OF THE FIGURES

FIG. 1A. Two dimerization peptides (DP) are fused to a linear protein (P), which results in a DP-protein structure (shown here as DP-protein-DP), which may fold into a compact structure due to the dimerization of DP. FIG. 1B. DP-protein structures comprising a linker (L). FIG. 1C. DP-protein structures comprising a tag sequence (Tag). $Tag_1$ and $Tag_2$ are two different tags fused to one DP-protein, indicating that many combinations of fusing tags to the DP-protein are possible. FIG. 1D. DP-protein with linkers in between DP and P and two different tags. FIG. 1E. DP-protein, wherein a dimerization peptide ($DP_1$) added to the N-terminus of P is different from a dimerization peptide ($DP_2$) added to the C-terminus of P. FIG. 1F. DP-protein comprising stability sequences such as MG at its N-terminus and GGPP at its C-terminus. FIG. 1G. DP-proteins, wherein multiple proteins $P_1$, $P_2$, and $P_3$ are fused to dimerization peptides.

FIG. 2A. Covalently associated double-loop structure. Due to the specific dimerization of $DP_{hyd}$:$DP_{hyd}$ and $DP_{Lys}$:$DP_{Glu}$, two constrained peptides are formed within one DP-protein and a double loop structure is expected. The two loop structures are covalently linked through a flexible glycine linker. FIG. 2B. Non-covalently associated double-loop structure. Two DP-proteins, one comprising $P_1$, the other comprising $P_2$ are made, each resulting in a compact structure due to the dimerization of $DP_{hyd}$:$DP_{hyd}$. When combined, due to the specific dimerization of and $DP_{Lys}$:$DP_{Glu}$, the two constrained structures associate yielding a double loop structure. The two dimerization peptides $DP_{hyd}$ and $DP_{Lys}$ or $DP_{hyd}$ and $DP_{Glu}$ are connected through a flexible glycine linker. FIG. 2C. Non-covalently associated double-loop structure, wherein unconstrained proteins $P_1$ and $P_2$ are forced into a compact structure due to the specific dimerization of $DP_{hyd}$:$DP_{hyd}$ and $DP_{Lys}$:$DP_{Glu}$. The dimerization peptides which associate are confined to different DP-proteins, however, associate with one another when the two DP-proteins are combined. FIGS. 2A–C. $DP_{hyd}$ is a dimerization peptide comprising mostly hydrophobic amino acids; $DP_{Lys}$ is a dimerization peptide comprising mostly lysines; $DP_{Glu}$ is a dimerization peptide comprising mostly glutamic acids; $L_P$ is a linker comprising prolines, $L_G$ is a linker comprising glycines; $P_1$ and $P_2$ are proteins, which may or may not be the same.

FIG. 3A. Dimerization of SKVILFE-amide and EFLIVKS-amide. FIG. 3B. Dimerization of EFLIVKS-amide when eluted from a C18 reversed phase column at pH ~2.5 in ca. 25% acetonitrile.

FIG. 5A. Elastase digestion products of the 18mer test protein sequence CGTIVTMEYRIDRTRSFC. FIG. 5B. Elastase digestion products of the 18mer test protein sequence CGTIVTMEYRIDRTRSFC with disulfide bonds between the two underlined cysteines. FIG. 5C. Elastase digestion products of EFLIVKS-VGTIVTMEYRIDRTRSFV-EFLIVKS. FIGS. 5A–C. Proteolytic fragments are monitored by reversed phase hpic coupled to mass spectrometry detection and identified.

FIG. 6. Overlay of the 45 lowest energy structures (only the peptide backbone is shown) of EFLIVKS-VGTIVTMEYRIDRTRSFV-EFLIVKS.

DETAILED DESCRIPTION OF THE INVENTION

Figure 1A:
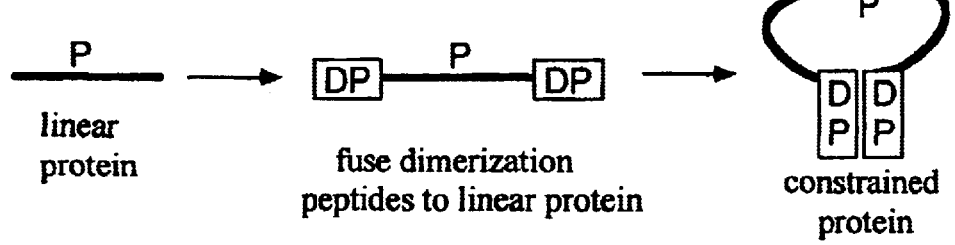
FIGS. 1A, 1B, 1C, 1D, 1E, 1F, and 1G depict schematic drawings of some embodiments of DP-protein structures.
Figure 1B:
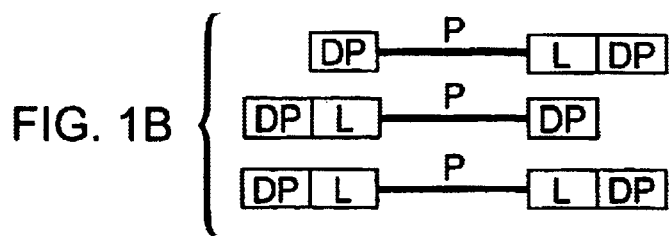
Figure 1C:
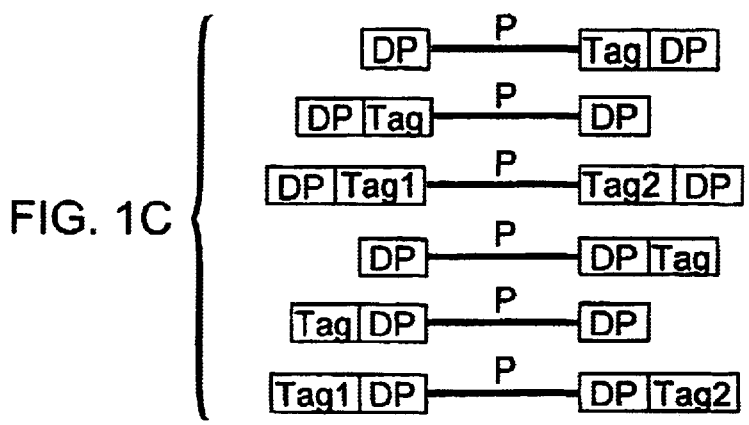
Figure 1D:
Figure 1E:
Figure 1F:
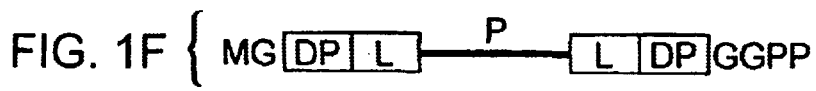
Figure 1G:
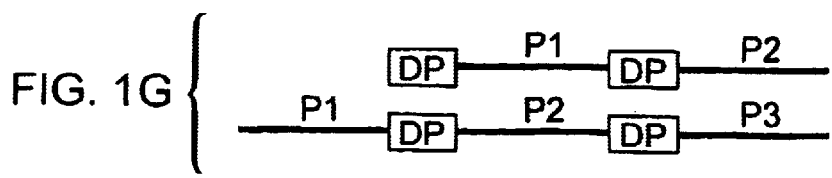

Cyclic or otherwise constrained peptides have many valuable features compared to their linear analogs, including enhanced stability to proteolysis and a restricted conformation space that can result in a higher binding affinity for cognate binding proteins due to a reduced entropic cost of binding. These constrained peptides can form the basis for the subsequent design of small molecules which may be useful as drug. Constrained peptides contained in minimized proteins may also be useful as an intermediate step in the design of agents blocking protein-protein interactions (Cunningham and Wells, Curr. Opin. Struct. Biol. 7:457462 (1997)], incorporated herein by reference, which may offer a novel method of regulating intracellular signaling pathways. When peptides are intracellularly expressed, they may modulate intracellular signaling pathways [Souroujon and Mochly-Rosen, Nat. Biotechnol. 16(10):919–24 (1998)]. If the peptides are expressed in live mammalian cells, they may be screened for defined changes in cellular phenotype, and the resulting bioactive peptides may provide a route for the affinity isolation of their binding targets.

Accordingly, the present invention provides dimerization peptides. By "dimerization peptide", "DP" or "association peptide" or grammatical equivalents herein is meant a peptide which either self-aggregates or dimerizes associates with a second peptide.

By "self-aggregates", or "dimerizes", "associates" herein is meant that a peptide has an affinity for another peptide and non-covalently attaches itself to this peptide. The interaction between two molecules (e.g. two peptides) that are capable of binding to one another is usually characterized in terms of the strength with which these molecules interact, i.e., the "affinity" that the molecules have for one another. The range of measured affinity constants, for example, for antibody-antigen binding extends from $10^5$ liter $mol^{-1}$ to above $10^{12}$ liter $mol^{-1}$ (Harlow and Lane, *Antibodies: A Laboratory Manual*, Cold Spring Harbor Laboratory Press, 1988). For comparison, the affinity of trypsin for its substrate is approximately $1.25 \times 10^4$ liter $mol^{-1}$ and the affinity of lambda repressor for DNA is $10^{10}$ liter $mol^{-1}$ (Harlow and Lane, supra). Dimerization peptides provided by this invention usually have affinities for one another in the range from about $10^5$ liter $mol^{-1}$ to about $10^{13}$ liter $mol^{-1}$, more usually from about $10^6$ liter $mol^{-1}$ to about $10^{13}$ liter $mol^{-1}$, from about $10^7$ liter $mol^{-1}$ to about $10^{13}$ liter $mol^{-1}$ being preferred, from about $10^8$ liter $mol^{-1}$ to about $10^{13}$ liter $mol^{-1}$ being more preferred, from about $10^9$ liter $mol^{-1}$ to about $10^{13}$ liter $mol^{-1}$ being mostly preferred, and from about $10^{10}$ liter $mol^{-1}$ to about $10^{13}$ liter $mol^{-1}$ being especially preferred. As is known to those in the art, measurement of affinity constants is affected by temperature, pH, and solvent.

By "peptide" herein is meant a compound which comprises at least two covalently attached amino acids and includes proteins, polypeptides, oligopeptides and peptides. The peptide may be made up of naturally occurring amino acids and peptide bonds, or synthetic peptidomimetic structures. Thus "amino acid", or "amino acid residue", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In general, peptides of the invention, including DPs and test peptides, comprise at least about 3 amino acids in length, usually from about 3 amino acids in length to about 100 amino acids, from about 3 amino acids in length to about 50 amino acids being preferred, from about 3 amino acids in length to about 10 amino acids being more preferred, from about 4 amino acids in length to about 10 amino acids being mostly preferred and from about 5 amino acids in length to about 9 amino acids being especially preferred; peptides of 5, 6, 7, 8, 9, and 10 amino acids are preferred. Similarly, when larger test proteins are used, these may comprise at least about 3 amino acids in length, usually from about 3 amino acids in length to about 1000 amino acids, from about 3 amino acids in length to about 600 amino acids being preferred, from about 3 amino acids in length to about 400 amino acids being more preferred, from about 3 amino acids in length to about 200 amino acids being mostly preferred and from about 3 amino acids in length to about 100 amino acids being especially preferred.

The dimerization peptides (DP) of the invention comprise the sequence $NH_2$—$X_1$—$X_2$—$X_3$—$X_4$—$X_5$—COOH and generally are no more than 9 amino acids long and wherein $X_1$, $X_2$, $X_3$, and $X_4$ are generally selected from the group consisting of amino acids A, V, I, L, W, F, M and Y and $X_5$ is generally selected from the group consisting of K, R, D and E.

In a preferred embodiment, the dimerization peptides (DP) comprise the sequence $NH_2$-FLIVK-COOH. As outlined above, other sequences include those with a high content of hydrophobic amino acids and 1 or 2 charged amino acid residues. Generally, a sequence composed of 5, 6, 7 and 8 amino acids with at least 34 highly hydrophobic residues (taken from A, F, I, L, M, V, W, and Y) will function in this fashion.

In a preferred embodiment the dimerization sequence is $NH_2$-XFLIVK-COOH, wherein X is either D, E, K, or R.

In another preferred embodiment the dimerization sequence is $NH_2$-FLIVKS-COOH.

In a preferred embodiment the dimerization sequence is $NH_2$-XFLIVKS-COOH, wherein X is either glutamic acid, aspartic acid, lysine or arginine.

In another embodiment, DP-proteins comprise sequences comprising $(Lys)_{4-8}$ or $(Arg)_{4-8}$ fused, as outlined in more detail below, to one terminus of a protein, and $(Asp)_{4-8}$ or $(Glu)_{4-8}$ fused to the other terminus of a protein. Such DP-proteins would be expected to form compact structures with the ends forming a 4–8 residue ion-paired extended array.

Particularly preferred embodiments include, but are not limited to, the sequences EFLIVKS, KFLIVKS, EEFLIVKKS, EEFLIVKKS-acid, VSIKFEL, SKVILFE, AFLIVKS, EALIVKS, EFAIVKS, EFLAVKS, EFLIAKS, EFLIVAS, EFLIVKA, EFLKVKS, SKVILFE, EFLIVES, EKLKVKS, ESLSVKS, EFLIVES, VSIKFEL, LIVKS, FESIKVL and LKSIVEF.

In a preferred embodiment, the DPs of the invention are covalently to a protein or peptide of interest, frequently referred to herein as "protein of interest", "peptide of interest", "test protein", or "test peptide", depending on its size.

By "protein of interest", "peptide of interest", "test protein" or "test pepide" or grammatical equivalents herein is meant a protein for which generally a function is sought or which has certain characteristics to be tested. Generally, test proteins are encoded by nucleic acids which are obtained from genomic DNA, cDNA or from random nucleic acids. These nucleic acids are expressed (as detailed below) to generate the test proteins. Smaller test proteins, usually test peptides, can also be synthesized on a peptide synthesizer. Synthesis on a peptide synthesizer allows the incorporation of synthetic analogs including, but not limited to, unnatural amino acids or peptidomimetic bonds to enhance potency and stability of the test protein or test peptide.

In a preferred embodiment, the test peptides are randomized. By "random" or "randomized" or grammatical equivalents herein is meant that each nucleic acid and peptide consists of essentially random nucleotides and random amino acids, respectively. Generally these random test peptides are expressed from a molecular library. In a preferred embodiment, the molecular library comprises at least two different randomized nucleic acid sequences, with a plurality of different randomized nucleic acid sequences being preferred. These nucleic acid sequences are chemically synthesized, and may incorporate any nucleotide at any position. The synthetic process can be designed to generate randomized nucleic acids, to allow the formation of all or most of the possible combinations over the length of the sequence, thus forming a library of randomized nucleic acids encoding randomized candidate proteinaceous molecules (e.g., randomized candidate DP-proteins). The randomized nucleic acid sequences such create a library of fragments, each encoding a different protein, which are ligated into suitable vectors and transformed into cells, as outlined herein.

In one embodiment, the library is fully randomized, with no sequence preferences or constants at any position.

In another preferred embodiment, the library is biased. That is, some positions within the sequence are either held constant, or are selecte from a limited number of possibilities. For example, in a preferred embodiment, triplets of nucleotides (NNN) are randomized to encode amino acid residues within a defined class, for example, hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The term "random peptide library", or "random protein library" is meant herein as to comprise recombinant vectors encoding random peptides (or random proteins), the random peptides (or random proteins) encoded by those recombinant vectors, recombinant vectors encoding fusion proteins, comprising random peptides (or random proteins), and the fusion proteins, comprising random peptides (random proteins), encoded by those recombinant vectors.

In a preferred embodiment, the sequence of the candidate DP-protein is used to generate derivatives of the originally isolated candidate DP-protein. For example, the sequence of the candidate DP-protein may be the basis of a second round of (biased) randomization, to generate derivative DP-proteins with increased or altered activities. Alternatively, the second round of randomization may change the affinity of the bioactive agent. Furthermore, it may be desirable to operably link the protein component of the identified DP-protein to different dimerization sequences than those used to isolate the original candidate DP-protein. This may result in a fusion protein that is more or less constrained and thus may have altered activities. It may also be desirable to "walk" around a potential binding site, in a manner similar to the mutagenesis of a binding pocket, by keeping one end of the ligand region constant and randomizing the other end to shift the binding of the peptide around.

In a preferred embodiment, the test protein comprises a wild-type or naturally occurring sequence. Alternatively, it may be a derivative protein thereof, that is, it may contain amino acid substitutions, insertions or deletions, or combinations thereof which are not found in the originally isolated DP-protein. These modifications are routinely performed by in vitro mutagenesis of the nucleic acid encoding the protein of interest. In vitro mutagenesis methods are well known to those in the art and are found in, for example, Sambrook et al., *Molecular Cloning: A Laboratory Manual* (New York: Cold Spring Harbor Laboratory Press, 1989) and Ausubel et al., *Short Protocols in Molecular Biology* (John Wiley & Sons, Inc., 1995).

The DPs of the invention are covalently joined to the test protein. By "covalently attached" or "covalently joined" or grammatical equivalents herein is meant that two moieties are attached by at least one bond, including sigma bonds, Pi bonds, and coordination bonds. As is more fully outlined below, the DPs of the invention are covalently joined to fusion partners and/or test peptides. Covalent attachment to a fusion partners and test peptides is accomplished by employing cysteine (disulfide) linkage, peptide bond linkage, a variety of bifunctional agents (cross-linking agents, such as maleimidobenzoic acid, methyidithioacetic acid, mercaptobenzoic acid, S-pyridyl dithiopropionate, etc.), or attachment via nonpeptide bonds. Examples of nonpeptide bonds include, but are not limited to, retroinverso bonds, N-methyl amine bonds, depspeptide bonds, hydroxyamino peptide isoteres, thioamide bonds, peptoids [Simon et al., Proc. Natl. Acad. Sci. USA 89:9367–71 (1992)], double bonds, reduced peptide bonds, ethylene bonds, keto peptide bond analogs, methylene sulfoxides, and methylene sulfides [Rizo and Gierasch, Annu. Rev. Biochem. 61:387418 (1992)].

In general, as detailed below, the DPs are joined to peptides or proteins using peptide bonds, for example by expressing nucleic acids that encode the DP and the respective peptide or protein of interest.

In a preferred embodiment, the DPs of the invention are joined to a test protein to form fusion proteins, in a wide variety of ways, as will be appreciated by those in the art. As is more fully described below, they can be joined to one or more internal positions, or preferably to either or both of the N- and C-terminal terminus. The attachment of DP to a fusion partner results in a structure referred to herein as DP-protein.

By "DP-protein" herein is meant a compound comprising at least one dimerization peptide covalently joined to at least one peptide. DP-proteins include candidate DP-proteins, as defined below. As will be appreciated by those in the art, when a single DP is used, the compositions and methods of the invention find use in the association of two test peptides. That is, a first DP ($DP_1$) can be joined to a first test protein ($protein_1$), and a second DP ($DP_2$) can be joined to a second test protein ($protein_2$). When two DPs are used, the compositions find use in the generation of constrained test peptides.

In a preferred embodiment, at least one DP is joined to the N-terminus of a test protein, with the attachment of two DPs being preferred. In this embodiment, when two or more DPs are joined to the test protein, the DPs may be identical in sequence or may have a different sequence. The DPs may or may not be separated by a linker sequence as further outlined below. In an embodiment, wherein the same DP or two different DPs with affinity for one another are, joined to the N-termini of two different test proteins, protein$_1$ and protein$_2$, generating, for example, DP-protein$_1$ and DP-protein$_2$, the two DPs associate with one another and protein$_1$ and protein$_2$ are brought into proximity. Due to the presence of the same DP sequence, in addition to protein$_1$:protein$_2$ heterodimers, protein$_1$:protein$_1$ homodimers and protein$_2$:protein$_2$ homodimers can be made.

In a preferred embodiment, at least one DP is joined to the C-terminus of a test protein, with the attachment of two DPs being preferred. As above, the DPs may be identical in sequence or may have a different sequence. The DPs may or may not be separated by a linker sequence as further outlined below. In an embodiment, wherein the same DP or two different DPs with affinity for one another are joined to the C-termini of two different test proteins, protein$_1$ and protein$_2$, generating, for example, protein$_1$-DP and protein$_2$-DP, the two DPs associate with one another and protein$_1$ and protein$_2$ are brought into proximity. Due to the presence of the same DP sequence, in addition to protein$_1$:protein$_2$ heterodimers, protein$_1$:protein$_1$ homodimers and protein$_2$:protein$_2$ homodimers are formed.

In a preferred embodiment, at least one DP is joined to an internal position of a test protein, with attachment of two DPs being preferred. As above, the DPs may be identical in sequence or may have a different sequence. The DPs may or may not be separated by a linker sequence as further outlined below. When two or more DPs are joined to an internal position, the DPs may be juxtaposed, that is inserted into the same internal position, for example, generating $_N$protein$_I$-DP$_1$-DP$_2$-$_I$protein$_C$ or the DPs may be separated and joined to different internal positions, for example, generating $_N$protein$_I$-DP$_1$-$_I$protein$_I$-DP$_2$-$_I$protein$_C$, wherein 'N' is the amino-terminal part of the test protein, 'C' is the carboxy-terminal part of the test protein, 'I' is an internal part of the protein, flanked by the dimerization peptides, DP$_1$ and DP$_2$. In an embodiment, wherein DP$_1$ and DP$_2$ are of identical sequence or have an affinity for one another, they associate and the part of the test protein enclosed by DP$_1$ and DP$_2$ (i.e., protein,) forms a loop structure.

In a preferred embodiment, the linkage of the DP to the test protein is direct; that is, there is a direct fusion of the DP sequence with the test protein sequence.

In a preferred embodiment, the linkage of the DP to the test protein is indirect; that is a linker or spacer is used. The term "linker", or "spacer", or "tethering sequence" or grammatical equivalents is meant herein to comprise a molecule or a group of molecules that connects two molecules. Often the inclusion of a linker serves to place the two molecules in a preferred configuration, for example, imposing a more constrained configuration on two molecules (such when linkers comprising prolines are used) or imposing a more relaxed configuration on two molecules (that is, minimal steric hindrance; such when linkers comprising serines and glycines are used).

In a preferred embodiment, a linker sequence is included at any position, i.e., in between DP and the protein of interest, in between two unrelated DPs, or in between two fusion partners. As outlined herein, the linker sequence can be proteinaceous or non-proteinaceous. Linker sequences between individual components of the compound may be desirable, for example, to allow the protein of interest to interact with potential targets unhindered, to constrain the protein of interest, or to allow functioning of a new property conferred upon the protein of interest (e.g., subcellular localization). For constraining a protein of interest, proline-containing linkers are particularly preferred. As is known in the art, prolines confer unique conformational constraints on a polypeptide chain. Useful proline linkers include proline-glycine polymers (including, but not limited to, (PG)$_n$, (PPGG)$_n$, (PP)$_n$, and combinations thereof, wherein n is an integer of at least one). Preferred linkers allowing some flexibility of the polypeptide include glycine-serine polymers (including, but not limited to, (GS)$_n$, (GSGGS)$_n$ and (GGGS)$_n$, and combinations thereof, wherein n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are particularly preferred.

In a preferred embodiment, the DP-protein comprises two DPs. In this embodiment, the two DPs are used to conformationally constrict the test protein. DPs, when covalently joined at the N- and C-terminus of a protein of interest (ranging from 3 to 50 or more amino acid residues), help the protein of interest to fold into a compact structure (also referred herein to as a constrained structure) which is more proteolytically resistant than the linear protein sequence alone. Particularly preferred in this embodiment and, when screening for interacting molecules, are random test proteins.

In a preferred embodiment, a first DP (DP$_1$) is fused to the N-terminus (N) of a test protein, and a second DP (DP$_2$) is fused to the C-terminus (C) of a test protein (protein), generating, for example, DP$_1$-$_N$protein$_C$-DP$_2$. In this embodiment, the first and second DP can be the same or different. When two DPs are used that can self-aggregate, the two DPs associate and impose a constrained structure upon the test protein enclosed in between the two DPs. When two different DPs (DP$_1$ and DP$_2$) are joined to the N-terminus and to the C-terminus of a test protein, the two different DPs nevertheless can associate and impose a constrained structure upon the test protein, provided, that DP$_1$ and DP$_2$ have an affinity for one another. Different DP sequences that can associate are, for example KFLIVKS and EFLIVES.

Particularly preferred examples of DP-proteins, include, but are not limited to: (i) EFLIVKS-protein-EFLIVKS; (ii) KVLIKS-protein-EFLIVES; (iii) VSIKFEL-protein-VSIKFEL; (iv) LIVKS-protein-LIVKS; (v) EFLIVK-protein-EFLIVK; (vi) FESIKVL-protein-FESIKVL; and (vii) LKSIVEF-protein-LKSIVEF.

More specifically, DP$_1$-protein-DP$_2$ like compounds provided by this invention comprise (i) EFLIKS-VGTIVTMEYRIDRTRSFV-EFLIFKS, wherein the protein sequence is obtained from the barley c2-chymotrypsin inhibitor [VGTIVTMEYRIDRTRSFV; Leatherbarrow and Salacinski, Biochemistry 30:10717–21 (1991)] and DP$_1$ and DP$_2$ are identical; (ii) EFLIKS-VGTIVTMEYRIDRTRSFV-SKVILFE, wherein the sequence of DP$_2$ is the reverse sequence of DP$_1$; (iii) SKVILFE-VGTIVTMEYRIDRTRSFV-EFLIVKS, wherein the sequence of DP$_1$ is the reverse of DP$_2$; (iv) SKVILFE-VGTIVTMEYRIDRTRSFV-SKVILFE, wherein both DP$_1$ and DP$_2$ are identical, however, the reverse of DP$_1$ and DP$_2$ shown in (i); (v) KFLIVKS-VGTIVTMEYRIDRTRSFV-KFLIVKS, wherein DP$_1$ and DP$_2$ are identical; (vi) KFLIVKS-VGTIVTMEYRIDRTRSFV-EFLIVES, wherein DP$_1$ and DP$_2$ are different; (vii) EFLIVES-VGTIVTMEYRIDRTRSFV-EFLIVES, wherein DP₁ and DP₂ are identical; (iix) EKLKVKS-VGTIVTMEYRIDRTRSFV-EKLKVKS, wherein DP₁ and DP₂ are identical; (ix) ESLSVKS-VGTIVTMEYRIDRTRSFV-ESLSVKS, wherein DP₁ and DP₂ are identical; (x) EFLKVKS-VGTIVTMEYRIDRTRSFV-EFLKVKS, wherein DP₁ and DP₂ are identical; (xi) EEFLIVKKS-VGTIVTMEYRIDRTRSFV-EEFLIVKKS, wherein DP₁ and DP₂ are identical; (xii) MG EFLIVKS-VGTIVTMEYRIDRTRSFV-EFLIVKSGPP, wherein DP₁ and DP₂ are identical and DP₁ comprises amino acids MG and DP₂ comprises amino acids GPP for conferring increased stability; (xiii) KKKKKKGGGG EFLIVKS-VGTIVTMEYRIDRTRSFV-EFLIVKS, wherein DP₁ and DP₂ are identical and DP₁ comprises amino acids KKKKKKGGGG for conferring increased solubility; (xiv) KKKGSGSEFLIVKS-VGTIVTMEYRIDRTRSFV-EFLIVKS, wherein DP₁ and DP₂ are identical and DP₁ comprises amino acids KKKGSGS for conferring increased solubility; (xv) EFLIVKS-STKSIPPQS-EFLIVKS, wherein the 9-mer insert represents an analog of a protease inhibitor [Gariani and Leatherbarrow, J. Peptide Res. 49:467–75 (1997)]; (xvi) MGEFLIVKS-GGGGDYKDDDDKGGGG-EFLIVKSGPP, wherein DP₁ and DP₂ are identical and DP₁ comprises amino acids MG and DP₂ comprises amino acids GPP for conferring increased stability and the protein comprises the flag epitope (DYKDDDDK) with glycine spacers; (xvii) MGEFLIVKS-GGGGYPYDVPDYASLGGGG-EFLIVKSGPP, wherein DP₁ and DP₂ are identical and DP₁ comprises amino acids MG and DP₂ comprises amino acids GPP for conferring increased stability and the protein comprises the influenza hemagglutinin epitope tag (YPYDVPDYASL) with glycine spacers. The dimerization sequence is underlined in all the above examples.

In a preferred embodiment, a first DP (DP₁) is joined to the N-terminus of the test protein and a second DP (DP₂) is joined to an internal position of the test protein. A structure such as DP₁-$_N$protein$_I$-DP₂-$_I$protein$_C$ is generated. In an embodiment, wherein DP₁ and DP₂ are of identical sequence or have an affinity for one another, they associate and the part of the test protein enclosed by DP₁ and DP₂ (i.e., $_N$protein$_I$) forms a loop.

In a preferred embodiment, a first DP (DP₁) is joined to the C-terminus of the test protein and a second DP (DP₂) is joined to an internal position of the test protein. A structure such as $_N$protein$_I$-DP₂-$_I$protein$_C$-DP₁ is generated. In an embodiment, wherein DP₁ and DP₂ are of identical sequence or have an affinity for one another, they associate and the part of the test protein enclosed by DP₁ and DP₂ (i.e., $_I$protein$_C$) forms a loop.

In a preferred embodiment, both the first DP (DP₁) and the second DP (DP₂) are joined to an internal position of the test protein or preferably to two different internal positions of the test protein, generating a structure such as $_N$protein$_I$-DP₁-$_I$protein$_I$-DP₂-$_I$protein$_C$. In an embodiment, wherein DP₁ and DP₂ are of identical sequence or have an affinity for one another, they associate and the part of the test protein enclosed by DP₁ and DP₂ (i.e., $_I$protein$_I$) forms a loop.

Figure 2A:
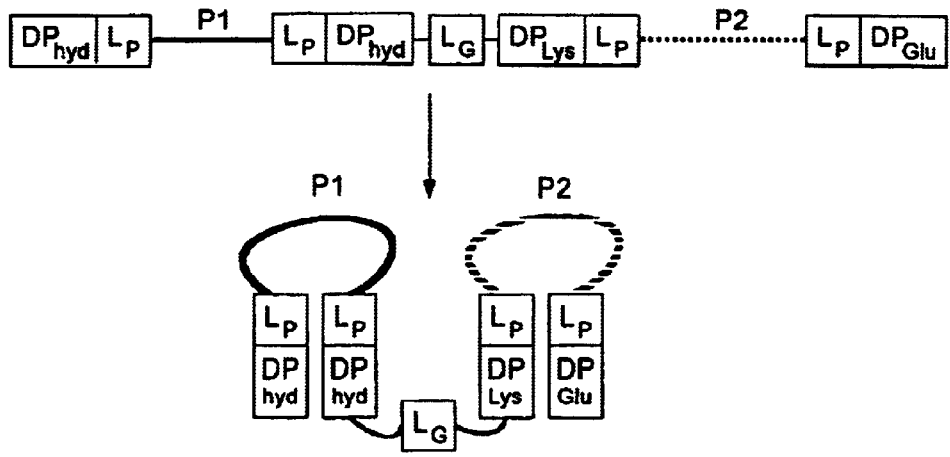
FIGS. 2A, 2B, and 2C depict schematic drawings of complex DP-proteins.

In a preferred embodiment, different dimerization peptides are fused to more than one protein which will be covalently associated with one another. In this embodiment, the individual dimerization peptides may also be separated by linkers inserted in between DP and a protein and/or in between individual DPs. For example, a DP fusion protein such as DP$_{hyd}$-L$_P$-protein$_1$-L$_P$-DP$_{hyd}$-L$_G$-DP$_{Lys}$-L$_P$-protein$_2$-L$_P$-DP$_{Glu}$ (see FIG. 2A), wherein DP$_{hyd}$ is a DP comprising mostly hydrophobic amino acid residues, DP$_{Lys}$ is a DP comprising mostly lysine residues, DP$_{Glu}$ is a DP comprising mostly glutamic acid residues, L$_P$ is a linker comprising proline residues, L$_G$ is a linker comprising glycine residues, and protein₁ and protein₂ are proteins which comprise different protein sequences, can be made. The above illustrated bivalent DP fusion protein will allow two constrained proteins covalently associated with one another within a single fusion protein, forming a 'double-loop' structure. Within such a structure, the first loop (comprising protein₁) is formed by the dimerization of the first DP$_{hyd}$ with the second DP$_{hyd}$ and the second loop (comprising protein₂) is formed by the dimerization of DP$_{Lys}$ and DP$_{Glu}$. The two loop structures may be separated by a flexible linker such as a glycine or serine/glycine linker as outlined above.

Figure 2B:
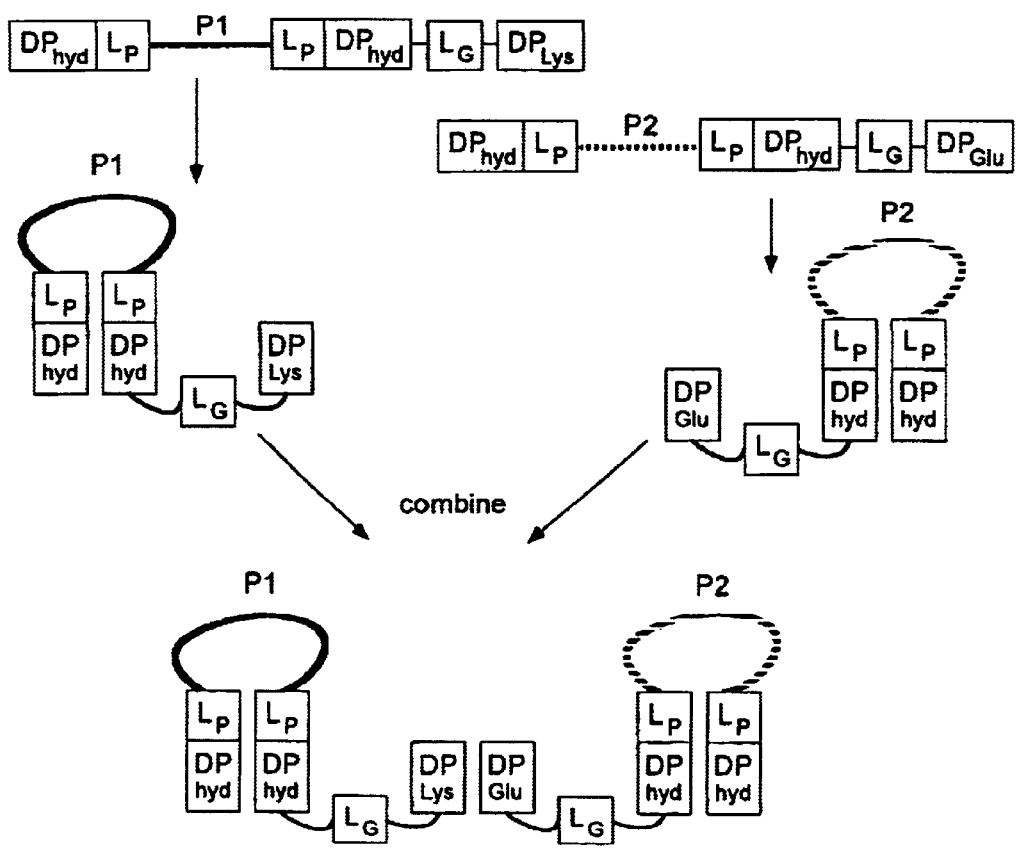

In a preferred embodiment, different dimerization peptides are fused to more than one protein which then non-covalently associate with one another. In this embodiment, the individual dimerization peptides may also be separated by linkers inserted in between DP and a protein and/or in between individual DPs. For example, the following DP fusion proteins can be made: (i) DP$_{hyd}$-L$_P$-protein$_1$-L$_P$-DP$_{hyd}$-L$_G$-DP$_{Lys}$ and (ii) DP$_{hyd}$-L$_P$-protein$_2$-L$_P$-DP$_{hyd}$-L$_G$-DP$_{Glu}$ (see FIG. 2B) wherein DP$_{hyd}$ is a DP comprising mostly hydrophobic amino acid residues, DP$_{Lys}$ is a DP comprising mostly lysine residues, DP$_{Glu}$ is a DP comprising mostly glutamic acid residues, L$_P$ is a linker comprising proline residues, L$_G$ is a linker comprising glycine residues, and protein₁ and protein₂ are proteins which comprise different protein sequences. In the above illustration, two individual proteins (protein₁ and protein₂) are each held in a compact structure, due to the association of the respective DPs. Upon mixing the two DP-fusion proteins, they form non-covalently associated dimers, due to the specific association of DP$_{Lys}$ with DP$_{Glu}$, resulting in a dimer structure which comprises two different compact proteins (protein₁ and protein₂). In another embodiment the protein sequences inserted in between the two DP$_{hyd}$s are identical: (i) DP$_{hyd}$-L$_P$-protein$_1$-L$_P$-DP$_{hyd}$-L$_G$-DP$_{Lys}$ and (ii) DP$_{hyd}$-L$_P$-protein$_1$-L$_P$-DP$_{hyd}$-L$_G$-DP$_{Glu}$, resulting in a non-covalent double loop structure comprising two juxtaposed compact structures of the same protein. It will be obvious to those in the art that a plurality of DP fusion proteins other than those illustrated herein, can be made.

Figure 2C:
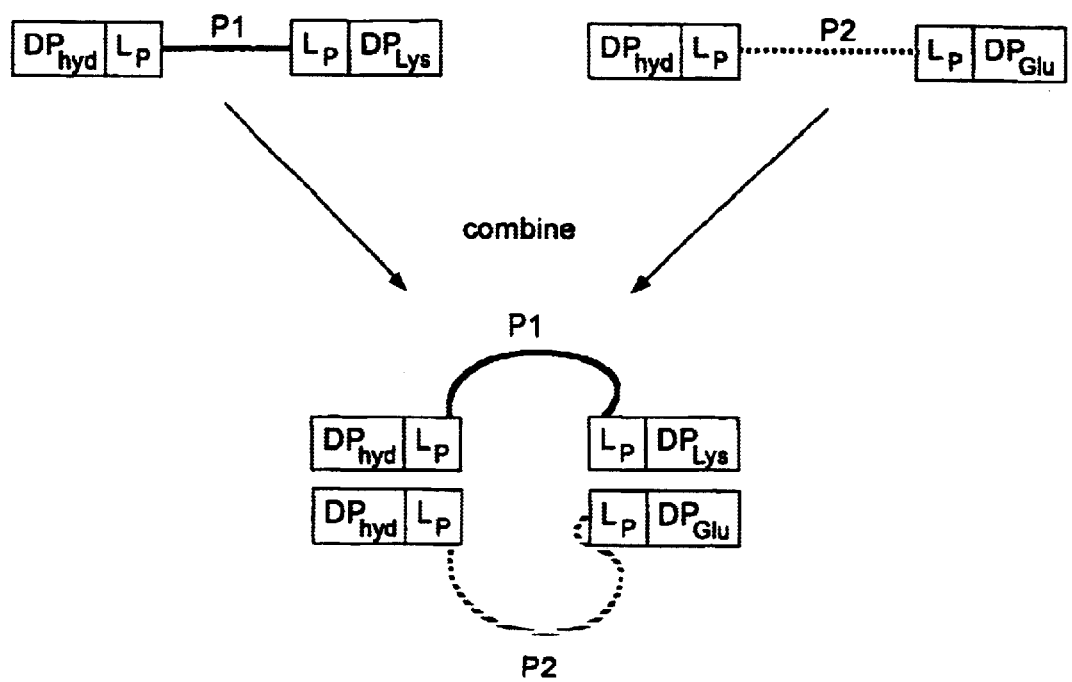

In a preferred embodiment, different dimerization peptides are fused to more than one protein which non-covalently associate with one another. In this embodiment, DP-proteins are generated, wherein the DPs are used to non-covalently associate two or more unconstrained proteins to form constrained structures (see FIG. 2C). In this embodiment, the individual dimerization peptides may also be separated conveniently by linkers inserted in between DP and a protein. For example, the following DP fusion proteins can be made: (i) DP$_{hyd}$-L$_P$-protein$_1$-L$_P$-DP$_{Lys}$ and (ii) DP$_{hyd}$-L$_P$-protein$_2$-L$_P$-DP$_{Glu}$, wherein DP$_{hyd}$ is a DP comprising mostly hydrophobic amino acid residues, DP$_{Lys}$ is a DP comprising mostly lysine residues, DP$_{Glu}$ is a DP comprising mostly glutamic acid residues, L$_P$ is a linker comprising proline residues, L$_G$ is a linker comprising glycine residues, and protein₁ and protein₂ are proteins which comprise different protein sequences. In the above illustration, two individual proteins (protein₁ and protein₂) are each held in a compact structure, due to the association of the respective DPs. Upon mixing the two DP-fusion proteins, they form non-covalently associated dimers, due to the specific association of DP$_{Lys}$ with DP$_{Glu}$, resulting in a dimer structure which comprises two different compact proteins (protein₁ and protein$_2$). In another embodiment the protein sequences inserted in between the two DP$_{hyd}$s are identical: (i) DP$_{hyd}$-L$_P$-protein$_1$-L$_P$-DP$_{hyd}$-L$_G$-DP$_{Lys}$ and (ii) DP$_{hyd}$-L$_P$-protein$_1$-L$_P$-DP$_{hyd}$-L$_G$-DP$_{Glu}$, resulting in a non-covalent double loop structure comprising two juxtaposed compact structures of the same protein. It will be obvious to those in the art that a plurality of DP fusion proteins other than those illustrated herein, can be made.

Other dimerizing protein sequences are known in the art or may be isolated using known screening systems, such as the yeast two-hybrid system.

In one embodiment, each of the two protein sequences (protein$_1$ and protein$_2$), for example, within the above DP$_{hyd}$-L$_P$-protein$_1$-L$_P$-DP$_{hyd}$-L$_G$-DP$_{Lys}$-L$_P$-protein$_2$-L$_P$-DP$_{Glu}$, has a specific bioactivity, which when combined in a structure as outlined above, results in a bivalent DP-fusion protein which has a greater bioactivity than each alone. For example, both compact structures may bind to the same target protein, however with low affinity. Combining both compact structures into a single bivalent DP-fusion protein as outlined above, may result in much higher affinity for the target protein, and thus the single DP-fusion protein may be a more potent agonist or antagonist than each isolated DP-protein.

In another preferred embodiment, DP-fusion protein structures as outlined above, such as DP$_{hyd}$-L$_P$-protein$_1$-L$_P$-DP$_{hyd}$-L$_G$-DP$_{Lys}$-L$_P$-protein$_2$-L$_P$-DP$_{Glu}$ which have a bivalent binding specificity are also useful for associating two proteins for which they have affinity. In this embodiment, the compact structure comprising protein$_1$ has affinity to a protein X; and the compact structure comprising protein$_2$ has affinity to protein Y. Introducing this DP-fusion protein into a cell which expresses both protein X and protein Y, results in binding of the bivalent DP-fusion protein to both protein X and protein Y, which thereby are brought into close proximity.

Similarly, DP-fusion protein structures as outlined above, such as DP$_{hyd}$-L$_P$-protein$_1$-L$_P$-DP$_{hyd}$-L$_G$-DP$_{Lys}$-L$_P$-protein$_2$-L$_P$-DP$_{Glu}$ which have a bivalent binding specificity are also useful for associating two cells. The cells may be identical or different. In this embodiment, the compact structure comprising protein, has affinity to a cell surface component X displayed on a first cell. The compact structure comprising protein$_2$ has affinity to a cell surface component Y displayed on a second cell. Co-culturing the first and second cells and providing this bivalent DP-fusion protein, results in binding of the DP-fusion protein to both cell surface component X and cell surface component Y, which will force first cell and second cell into close proximity.

Among the most challenging aspects in gene therapy is the delivery of the gene of interest into a specific target cell, wherein a genetic defect is sought to be corrected. Several gene delivery systems are known to those in the art, including, but not limited to naked DNA, liposome-embedded DNA, and viral systems, comprising retroviruses, adenoviruses, herpesviruses, HIV, etc. However, whatever system is employed, cell-type specific delivery remains the most critical aspect of gene therapy. In a preferred embodiment, DP-fusion protein structures as outlined above, such as DP$_{hyd}$-L$_P$-protein$_1$-L$_P$-DP$_{hyd}$-L$_G$-DP$_{Lys}$-L$_P$-protein$_2$-L$_P$-DP$_{Glu}$ which have a bivalent binding specificity are also useful as tools for associating virus particles (e.g., a virus that delivers a gene of interest) with the desired target cells. In this embodiment, the compact structure, comprising protein$_1$ has affinity to a cell surface component X displayed on a the virus and the compact structure comprising protein$_2$ has affinity to a cell surface component Y displayed on a target cell. Co-culturing the virus and the target cells and providing this bivalent DP-fusion protein, results in binding of the bivalent DP-fusion protein to both viral surface component X and target cell surface component Y, which will force the virus into close proximity with its target cell. The viral particle thus may dock to the desired target cell and fuse with the membrane ensuring gene delivery. Suitable controls are performed such that the virus does not dock with its target cell without addition of the bivalent DP-fusion protein.

In another embodiment the protein sequences inserted in between the two DP$_{hyd}$s and in between DP$_{Lys}$ and DP$_{Glu}$ are identical, resulting in a double loop structure comprising two juxtaposed compact structures of the same protein. This embodiment allows the dimerization of the same protein, which may be a cellular protein or an extracellular protein component. It will be obvious to those in the art that a plurality of DP fusion proteins other than those illustrated herein, can be made.

The DPs or DP-proteins of the present invention may also be modified, as more fully outlined below, to form fusion proteins comprising a DP or a DP-protein and another, heterologous protein or amino acid sequence, usually referred to as a fusion partner.

The term "fusion protein" or "chimeric protein" refers to a protein composed of at least two proteins that, while typically unjoined in their native state, typically are joined by their respective amino and carboxyl termini through a peptide linkage to form a single continuous protein. It will be appreciated that the protein components can be directly joined or joined through a peptide linker/spacer.

By "fusion partner" herein is meant a sequence that is associated with DP or DP-protein and confers upon DP or DP-protein an additional function or ability. Suitable fusion partners include, but are not limited to: a) tag sequences (also referred to as rescue sequences), as defined below, which allow the purification or isolation of either the DP or DP-protein or the nucleic acids encoding them; b) targeting sequences, defined below, which allow the localization of DP or DP-protein to a subcellular or extracellular compartment; c) stability sequences, which confer stability or protection from degradation to DP or DP-protein, for example resistance to proteolytic degradation; or d) any combination of a), b), and c), as well as linker sequences as needed. It is well known to those in the art that fusion proteins preferably are generated by in vitro mutagenesis and genetic engineering, whereby the nucleic acid encoding the respective fusion protein is modified accordingly. Suitable methods can be found, for example, in Sambrook et al., *Molecular Cloning: A Laboratory Manual* (New York: Cold Spring Harbor Laboratory Press, 1989) and Ausubel et al., *Short Protocols in Molecular Biology* (John Wiley & Sons, Inc., 1995).

In a preferred embodiment, the fusion partner comprises a tag polypeptide which provides an epitope to which an anti-tag antibody can selectively bind or an epitope comprising a purification sequence. The epitope tag is generally, but not required to be, placed at the amino- or carboxyl-terminus of DP or DP-protein. The presence of such epitope-tagged forms of DP or DP-protein can be detected using an antibody against the tag polypeptide. Also, the use of the tag enables the protein to be readily purified by affinity purification using an anti-tag antibody or another type of affinity matrix that binds to the epitope tag. In an alternative embodiment, the chimeric molecule may comprise a fusion of DP or DP-protein with an immunoglobulin or a particular region of an immunoglobulin. For a bivalent form of the chimeric molecule, such a fusion could be to the Fc region of an IgG molecule or to GST (glutathione S transferase).

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Mol. Cell. Biol., 5:3610–3616 (1985)]; and the Herpes Simplex virus glycoprotein D (gD) tag and its antibody [Paborsky et al., Protein Eng., 3(6):547–553 (1990)]. Other tag polypeptides include the Flag-peptide [Hopp et al., Mol. Immunol., 33:601–8 (1996); Brizzard et al., Biotechniques 16(4):730–735 (1994); Knappik and Pluckthun, Biotechniques 17(4):754–61 (1994), the KT3 epitope peptide [Martin et al., Science, 255:192–194 (1992)], the tubulin epitope peptide [Skinner et al., J. Biol. Chem., 266:14163–14166 (1991)], and the T7 gene 10 protein peptide tag [Lutz-Freyermuth et al., Proc. Natl. Acad. Sci. USA, 87:6393–6397 (1990)]. Alternatively, for example, fusion proteins encompassing poly-his tags are efficiently purified on metal (Ni) affinity resins.

In a preferred embodiment, a tag sequence (also referred to as a rescue sequence) is used to isolate the nucleic acid encoding the DP-protein (see also below). In this embodiment the rescue sequence may be a unique oligonucleotide sequence which serves as a probe target site to allow quick and easy isolation of the nucleic acid construct (see below), via PCR, hybridization, or related techniques.

In a preferred embodiment, the fusion partner is a targeting sequence. As will be appreciated by those in the art, the localization of proteins within a cell is a simple method for increasing effective concentration and determining function. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization, for example, shuttling the proteins into the nucleus confines them to a smaller space thereby increasing concentration.

Thus, suitable targeting sequences include, but are not limited to, (i) sequences capable of causing binding of the respective protein to a predetermined molecule or class of molecules while retaining bioactivity of the expression product, (for example by using enzyme inhibitor or substrate sequences to target a class of relevant enzymes); (ii) sequences signaling selective degradation, of itself or co-bound proteins; and (iii) signal sequences capable of constitutively localizing the candidate expression products to a predetermined cellular locale, including (a) subcellular locations such as the Golgi apparatus, endoplasmic reticulum, nucleus, nucleoli, nuclear membrane, mitochondria, chloroplast, secretory vesicles, lysosome, and cellular membrane; and (b) extracellular locations via a secretory signal [see, von Heijne, EXS 73:67–76 (1995); von Heijne, Subcell. Biochem. 22:1–19 (1994) and von Heijne, Curr. Opin. Cell. Biol. 2(4):604–8 (1990)]. Particularly preferred is localization to either subcellular locations or to the outside of the cell via secretion.

In a preferred embodiment, the fusion partner is a nuclear localization signal (NLS). NLSs are generally short, positively charged (basic) domains that serve to direct the entire protein in which they occur to the cell's nucleus. Numerous NLS amino acid sequences have been reported including: (i) single basic NLS's such as that of the SV40 (monkey virus) large T Antigen [Pro Lys Lys Lys Arg Lys Val; Kalderon et al., Cell 39:499–509 (1984)]; the human retinoic acid receptor-β nuclear localization signal (ARRRRP; Hamy et al., Bioconjug. Chem. 2(5):375–8 (1991); NFκB p50 [EEVQRKRQKL; Ghosh et al., Cell 62:1019–1029 (1990)]; NFκB p65 [EEKRKRTYE; Nolan et al., Cell 64:961–969 (1991)]; and others [see for example Boulikas, J. Cell. Biochem. 55(1):32–58 (1994)], hereby incorporated by reference and (ii) double basic NLS's exemplified by that of the Xenopus laevis (African clawed toad) protein, nucleoplasmin [Ala Val Lys Arg Pro Ala Ala Thr Lys Lys Ala Gly Gin Ala Lys Lys Lys Lys Leu Asp; Dingwall et al., Cell 30:449458 (1982) and Dingwall et al., J. Cell. Biol. 107:841–849 (1988)]. Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall and Laskey, Annu. Rev. Cell. Biol., 2:367–390 (1986); Bonnerot et al., Proc. Natl. Acad. Sci. USA, 84:6795–6799 (1987) and Galileo et al., Proc. Natl. Acad. Sci. USA, 87:458462 (1990).

In a preferred embodiment, the fusion partner is a membrane anchoring signal sequence. This is particularly useful since many parasites and pathogens bind to the membrane, in addition to the fact that many intracellular events originate at the plasma membrane. Thus, membrane-bound DP-proteins are useful for both the identification of important elements in these processes as well as for the discovery of effective inhibitors or activators. The invention provides methods for presenting the DP protein extracellularly or in the cytoplasmic space. For extracellular presentation, a membrane anchoring region is provided at the carboxyl terminus of the DP-protein. The DP-protein is exposed on the cell surface and presented to the extracellular space, such that it can bind to other surface molecules (affecting their function) or molecules present in the extracellular medium. The binding of such molecules could confer function on the cells expressing a DP-protein that binds the molecule. The cytoplasmic region could be neutral or could contain a domain that, when the extracellular DP-protein is bound by a target protein or test protein, confers a function on the cells (activation of a kinase, phosphatase, binding of other cellular components to effect function). Similarly, the DP-protein-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a secretory signal sequence and require a hydrophobic transmembrane domain. Of course, if a transmembrane domain is placed amino-terminal to the DP-protein region, it will serve to anchor the DP-protein as an intracellular domain, which may be desirable in some embodiments. Secretory signal sequences and transmembrane domains are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchored protein sequences, including both SS and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: (i) class I integral membrane proteins such as IL-2 receptor beta-chain [residues 1–26 are the signal sequence, residues 241–265 are the transmembrane residues; see Hatakeyama et al., Science 244:551–556 (1989) and von Heijne and Gavel, Eur. J. Biochem.174:671–678 (1988)] and insulin receptor beta chain [residues 1–27 are the signal sequence, residues 957–959 are the transmembrane domain and residues 960–1382 are the cytoplasmic domain; see Hatakeyama, supra, and Ebina et al., Cell 40:747–758 (1985)]; (ii) class II integral membrane proteins such as neutral endopeptidase (residues 29–51 are the transmembrane domain, residues 2–28 are the cytoplasmic domain; see Malfroy et al., Biochem. Biophys. Res. Commun. 144:59–66 (1987)]; (iii) type III proteins such as human cytochrome P450 NF25 (Hatakeyama, supra); and (iv) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These sequences encode the amino acids 1–32 in the case of CD8 [MASPLTRFLSLNLLLLGESILGSGEAKPQAP; Nakauchi et al., Proc. Natl. Acad. Sci. USA 82:5126–30 (1985)] and 1–21 in the case of ICAM-2 [MSSFGYRTLTVALFTLICCPG; Staunton et al., Nature 339:61–64 (1989)]. These leader sequences deliver the construct to the membrane while the hydrophobic transmembrane domains, placed carboxy-terminal to the DP-protein region, serve to anchor the construct in the membrane. These transmembrane domains are encompassed by amino acids 145–195 from CD8 (PQRPEDCRPRGSVKGTGLDFACDIYIWAPLAGICV ALLLSLIITLICYHSR; Nakauchi, supra) and 224–256 from ICAM-2 (MVIIVTVVSVLLSLFVTSVLLCFIFGQHLRQQR; Staunton, supra).

Alternatively, membrane anchoring sequences include the GPI anchor, which results in a covalent bond between the molecule and the lipid bilayer via a glycosylphosphatidylinositol bond for example in DAF [PNKGSGTTSGTTRLLSGHTCFTLTGLLGTLVTMGLLT, with the bolded serine being the site of the anchor; see Homans et al., Nature 333(6170):269–72 (1988), and Moran et al., J. Biol. Chem. 266:1250–1257 (1991)]. In order to do this, the GPI sequence from Thy-1 can be inserted 3' of the variable region in place of a transmembrane sequence.

It is within the scope of this invention to display the DP-protein on membranes of viral, archaebacterial, prokaryotic and eukaryotic origin. In this embodiment, the DP-protein is fused to a membrane protein such that after insertion into the membrane, the DP-protein region will be located on the outside of the virus, archaebacteria, prokaryote or eukaryotic cell and thus be accessible for binding target molecules, e.g., when screening for binding target molecules. Prokaryotic surface display systems, include, for example, functional fusions to surface proteins such as flagellin [Lu et al., Biotechnology 13(4):366–72 (1995) and ice-nucleation protein [Jung et al., Nat. Biotechnol. 16(6):576–80 (1998)]. Other prokaryoti protein display systems are reviewed by Stahl and Uhlen, Trends Biotechnol. 15(5):185–92 (1997) and Georgiou et al., Nat. Biotechnol. 15(1):29–34 (1997). Viral display system include, but are not limited to, (i) filamentous bacteriophages such as M13 and derivatives [for review see Felici et al., Biotechnol. Annu. Rev. 1:149–83 (1995)]; (ii) bacteriophage T4 [Jiang et al., Infect. Immun. 65(11):4770–7 (1997)]; (iii) bacteriophage lambda [Stolz et al., FEBS Lett. 440(1–2):213–7 (1998)]; (iv) tomato bushy stunt virus [Joelson et al., J. Gen. Virol. 78(Pt 6):1213–7 (1997)]; and (v) retrovirus [Buchholz et al., Nat. Biotechnol. 16(10):9514 (1998)]. Yeast display systems, for example, employ C-terminal fusions to the Aga2p mating adhesion receptor of *Saccharomyces cerevisiae* [Boder and Wittrup, Nat. Biotechnol. 15(6):553–7 (1997)]. Display of proteins using any of the above listed systems or mammalian transmembrane proteins (some of which are described herein) is generally achieved by inserting the nucleic acid encoding the DP-protein (or any other protein of interest) in frame with an amino-terminal secretion signal and a C-terminal transmembrane anchoring domain (as further described below).

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (see Cross et al., Mol. Cell. Biol. 4(9):1834–1842 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed amino-terminal to the variable region in order to localize the fusion protein to the plasma membrane. Other modifications such as palmitoylation can be used to anchor fusion proteins in the plasma membrane; for example, palmitoylation sequences from the G protein-coupled receptor kinase GRK6 sequence [LLQRLFSRQDCCGNCSDSEEELPTRL, with the bold cysteines being palmitolyated; Stoffel et al., J. Biol. Chem. 269:277914 (1994)]; from rhodopin [KQFRNCMLTSLCCGKNPLGD; Barnstable and Morabito, J. Mol. Neurosci. 5(3):207–9 (1994)]; and the p21 H-ras 1 protein [LNPPDESGPGCMSCKCVLS; Capon et al., Nature 302:33 (1983); Cadwallader et al., Mol. Cell. Biol. 14(7):4722–30 (1994)].

In a preferred embodiment, the fusion partner is a lysosomal targeting sequence, including, for example, a lysosomal degradation sequence such as Lamp-2 [KFERQ; Dice, Ann. N.Y. Acad. Sci. 674:58–64 (1992)]; or lysosomal membrane sequences from Lamp-1 [MLIPIAGFFALAGLVLIVLIAYLIGRKRSHAGYQTI, Uthayakumar et al., Cell. Mol. Biol. Res. 41:405–20 (1995)] or Lamp-2 [LVPIAVGAALAGVLILVLLAYFIG LKHHHAGYEQF, Konecki et al., Biochem. Biophys. Res. Comm. 205:1–5 (1994)], both of which show the transmembrane domains in bold and the cytoplasmic targeting signal underlined.

Alternatively, the fusion partner may be a mitochondrial localization sequence, including mitochondrial matrix sequences [e.g., yeast alcohol dehydrogenase III; MLRTSSLFTRRVQPSLFSRNILRLQST; Schatz, Eur. J. Biochem. 165:1–6 (1987)]; mitochondrial inner membrane sequences (yeast cytochrome c oxidase subunit IV; MLSLRQSIRFFKPATRTLCSSRYLL; Schatz, supra); mitochondrial inter-membrane space sequences (yeast cytochrome c1; MFSMLSKRWAQRTLSKSFYSTATGMSKSGKLTQKLVTAGVA AAGITASTLLYADSLTAEAMTA; Schatz, supra) or mitochondrial outer membrane sequences (yeast 70 kD outer membrane protein; MKSFITRNKTAILATVAATG-TAIGAYYYYNQLQQQQ QRGKK, Schatz, supra).

The fusion partner may also be derived from endoplasmic reticulum sequences, including a sequence derived from calreticulin [KDEL; Pelham, Proc. R. Soc. Lond. B. Biol. Sci., 250:1–10 (1992)] or from adenovirus E3/19K protein [LYLSRRSFIDEKKMP; Jackson et al., EMBO J. 9:3153–62 (1990)].

Furthermore, targeting sequences also include peroxisome sequences [for example, the peroxisome matrix sequence from luciferase; SKL; Keller et al., Proc. Natl. Acad. Sci. USA 84:3264–8 (1987)]; farnesylation sequences [for example, $P_{21}$ H-ras 1; LNPPDESGPGCMSCKCVLS, with the bold cysteine farnesylated; Capon, supra; Zhang et al., Biochemistry, 35(25):8166–71 (1996)]; geranylgeranylation sequences [for example, protein rab-5A; LTEPTQPTRNQCCSN, with the bold cysteines geranylgeranylated; Farnsworth, Proc. Natl. Acad. Sci. USA 91:11963–7 (1994)]; or destruction 21 sequences [cyclin B1; RTALGDIGN; Klotzbucher et al., EMBO J. 15(12):3053–64 (1996)].

In a preferred embodiment, the targeting sequence is a secretory signal sequence capable of effecting the secretion of the DP-protein. There is a large number of known secretory signal sequences which, for example, when placed amino-terminal to the DP-protein region are cleaved from the respective fusion protein during the secretion process.

Suitable secretory signal sequences, include those from IL-2 [MYRMQLLSCIALSLALVTNS; Villinger et al., J. Immunol. 155:3946–54 (1995)], growth hormone [MATGSRTSLLLAFGLLCLPWLQEGSAFPT; Roskam and Rougeon, Nucleic Acids Res. 7:305–20 (1979)); preproinsulin [MALWMRLLPLLALLALWGPDPAAAFVN; Bell et al., Nature 284:26–32 (1980); and influenza HA protein [MKAKLLVLLYAFVAGDQI; Sekiwawa and Lai, Proc. Natl. Acad. Sci. USA 80:3563–71 (1983)], with cleavage between the non-underlined-underlined junction. A particularly preferred secretory signal sequence is the secretory signal sequence from the secreted cytokine IL4, which comprises the first 24 amino acids of IL-4 as follows: MGLTSQLLPPLFFLLACAGNFVHG. Other secretory signal peptides are discussed in von Heinje, supra.

In a preferred embodiment, the fusion partner is a stability sequence which confers stability to DP or DP-protein or the nucleic acid encoding them. Thus, for example, proteins may be stabilized by the incorporation of glycines after the initiation methionine (MG or MGG), for protection of the protein to ubiquitination as per Varshavsky's N-End Rule (Bachmair et al., Science, 234:179–86 (1986); Gonda et al., J. Biol. Chem. 264:16700–12 (1989); Varshafsky, Genes Cells, 2(1):13–28 (1997)], thus conferring long half-life in the cytoplasm. Similarly, one or two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: $MG(X)_n GGPP$, $MG(X)_n GPP$, $MGG(X)_n GGPP$, and $MGG(X)_n GPP$ or wherein X is any amino acid and n is an integer of at least four.

In a preferred embodiment, to increase the solubility of the DP-protein, lysines are added to the N-terminus, which may or may not comprise a glycine spacer. For example, the DP-protein $K_6G_4$-EFLIVKS-protein-EFLIVKS can be made, which has different characteristics than the DP-protein without the $K_6G_4$ sequence added (see Examples). In this embodiment, the number of lysine residues and linker sequence can be determined experimentally to ensure the resulting DP-protein has the desired characteristics.

In a preferred embodiment, combinations of fusion partners are used. Thus, for example, any number of combinations of fusion partners, targeting sequences, rescue sequences, and stability sequences may be used, with or without linker sequences. As is more fully described below, using a base vector that contains at least one cloning site for receiving random and/or biased libraries, one can cassette in nucleic acids encoding various fusion partners 5' and 3' of the nucleic acid encoding the DP-protein.

In a preferred embodiment, the DPs, DP-proteins, DPs fused to a fusion partner or DP-proteins fused to a fusion partner of the invention can be further modified.

A compound wherein at least one dimerization peptide (DP) is fused to a protein of interest (P), for example, yielding DP-P, P-DP, DP-P-DP or similar compounds, as more fully described above, wherein DP is the dimerization peptide and P is a protein of interest, is collectively referred to as "DP-protein". Covalent modifications of DP and DP-proteins are included within the scope of this invention.

One type of covalent modification includes reacting targeted amino acid residues with an organic derivatizing agent that is capable of reacting with selected side chains or the N- or C-terminal residues of DP or DP-protein. Derivatization with bifunctional agents is useful, for instance, for crosslinking DP or DP-protein to a water-insoluble support matrix or surface for use in the method for purifying anti-DP or anti-DP-protein antibodies or screening assays, as is more fully described below. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, in *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of DP or DP-protein included within the scope of this invention comprises altering the native glycosylation pattern of the polypeptide. "Altering the native glycosylation pattern" is intended for purposes herein to mean deleting one or more carbohydrate moieties found in either DP or DP-protein, and/or adding one or more glycosylation sites that are not present in either DP or DP-protein.

Addition of glycosylation sites to DP or DP-protein may be accomplished by altering the amino acid sequence thereof. The alteration may be made, for example, by the addition of, or substitution by, one or more serine or threonine residues to the native sequence of DP or DP-protein (for O-linked glycosylation sites). The DP or DP-protein amino acid sequence may optionally be altered through changes at the DNA level, particularly by mutating the DNA encoding DP or DP-protein at preselected bases such that codons are generated that will translate into the desired amino acids. Methods for introducing mutations into DNA by in vitro mutagenesis are well known to those in the art and can be found, for example, in Sambrook et al., *Molecular Cloning:*

A *Laboratory Manual* (New York: Cold Spring Harbor Laboratory Press, 1989) and Ausubel et al., *Short Protocols in Molecular Biology* (John Wiley & Sons, Inc., 1995).

Another means of increasing the number of carbohydrate moieties on DP or DP-protein is by chemical or enzymatic coupling of glycosides to the polypeptide. Such methods are described in the art, for example, in WO 87/05330 published Sep. 11, 1987, and in Aplin and Wriston, CRC Crit. Rev. Biochem., 10(4):259–306 (1981).

Removal of carbohydrate moieties present on DP or DP-protein may be accomplished chemically or enzymatically or by mutational substitution of codons encoding amino acid residues that serve as targets for glycosylation. Chemical deglycosylation techniques are known in the art and described, for instance, by Sojar and Bahl, Arch. Biochem. Biophys., 259:52–57 (1987) and by Edge et al., Anal. Biochem., 118:131–137(1981). Enzymatic cleavage of carbohydrate moieties on polypeptides can be achieved by the use of a variety of endo- and exo-glycosidases as described by Thotakura and Bahl, Meth. Enzymol., 138:350–359 (1987).

Another type of covalent modification comprises linking a DP or a DP-protein to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

As will be appreciated by those in the art, the DPs, DP-proteins, and fusion proteins of the invention can be made in a variety of ways.

In a preferred embodiment, the DPs, DP-proteins, and fusion proteins are made synthetically, as is well known in the art.

In a preferred embodiment, the DPs, DP-proteins, and fusion proteins are encoded by nucleic acids, as is well known in the art.

In a preferred embodiment, the DP-proteins, including candidate DP-proteins, are translation products of nucleic acids. The candidate DP-protein comprises a randomized test protein. That is, every candidate DP-protein has a randomized portion, as defined above, that is the basis of the screening methods outlined below. In addition, to the randomized portion, the candidate DP-protein may also include a fusion partner. In this embodiment, the nucleic acids are introduced into cells, and the cells express the nucleic acids to generate DP-proteins (or candidate DP-proteins).

As outlined above, the DP-proteins are encoded by nucleic acids. A "nucleic acid", or "oligonucleotide", or a grammatical equivalent thereof herein means at least two nucleotide residues covalently linked together. A nucleic acid of the present invention will generally contain phosphodiester bonds. Modifications of the ribose-phosphate backbone may be done to facilitate the addition of additional moieties such as labels, or to increase the stability and half-life of such molecules in physiological environments. The nucleic acids may be single stranded or double stranded, or contain portions of both double stranded or single stranded sequence. The nucleic acid may be RNA, comprising RNA, mRNA, and defined or random ribo-oligonucleotides. The nucleic acid may be DNA, comprising genomic DNA, cDNA and defined or random deoxyribo-oligonucleotides. The nucleic acid may also be a hybrid, where the nucleic acid contains any combination of deoxyribo- and ribo-nucleotides, and any combination of nucleotide bases.

The nucleic acids encode the DP-proteins and the fusion partners, if present. In addition, the nucleic acids will also generally contain extra sequences to effect translation or transcription, as necessary. Usually, the nucleic acid encoding the DP proteins is incorporated into a suitable vector such as plasmid vectors or retroviral vectors. In a preferred embodiment, when plasmid vectors are used to express the DP-proteins, the nucleic acid is generally DNA. In another preferred embodiment, when retroviral vectors are used to express the DP-proteins, the nucleic acid is generally RNA.

In a preferred embodiment, vectors are used to express candidate DP-proteins. By "vector" herein is meant a replicon which comprises nucleic acid and can be used for the transformation of host cells. The vectors may be either self-replicating extrachromosomal vectors, referred to as "plasmids" or "plasmid vectors", or vectors which integrate into a host genome. A preferred embodiment utilizes retroviral vectors, as is more fully described below.

For non-retroviral embodiments, suitable vectors are derived from any number of known vectors, including, but not limited to, pcDNA3.1 (Invitrogen), pSI (Promega Corporation), and pBI (Clontech Laboratories, Inc.). Basically, any mammalian expression vectors with strong promoters such as CMV can be used to construct vectors expressing DP-proteins.

Generally, these expression vectors include transcriptional and translational regulatory nucleic acid operably linked to nucleic acids which are to be expressed. "Operably linked", in this context means that the transcriptional and translational regulatory nucleic acid is positioned relative to a coding sequence (e.g. encoding DP-protein) in such a manner that transcription is initiated and translation of the protein is assured. Generally, this will mean that the promoter and transcriptional initiation or start sequences are positioned 5' to the coding region. The transcriptional and translational regulatory nucleic acid will generally be appropriate to the host cell used, as will be appreciated by those in the art. Numerous types of appropriate expression vectors, and suitable regulatory sequences, are known in the art for a variety of host cells.

In general, the transcriptional and translational regulatory sequences may include, but are not limited to, promoter sequences (including CAAT box and TATA box), ribosomal binding sites (including internal ribosome entry sites (IRES)), transcriptional start and stop sequences (including mRNA polyadenylation sequence 5'-AATAAA-3'), RNA splicing sequences, translational start and stop sequences (including 5' and 3' untranslated regions, initiator codon (ATG), Kozak consensus sequence (5'-A/GNNATGG-3') and nonsense codons (UAA, UAG, UGA), either constitutive or inducible enhancer, activator or repressor sequences (located either upstream, downstream or overlapping relative to promoter and being either cell-line dependent, tissue-specific or temporally dependent), and protein targeting signals (including signals for endoplasmatic reticulum retention and extracellular secretion, signals for localization to plasma membranes, peroxisomes, nucleus, mitochondria, lysosomes, golgi complex and focal adhesions).

In a preferred embodiment, the regulatory sequences include a promoter and transcriptional start and stop sequences. Promoter sequences include constitutive and inducible promoter sequences [for example, see Walther and Stein, J. Mol. Med. 74(7):379–92 (1996)]. In a preferred embodiment, the promoters are constitutive and drive the expression of e.g., the DP-protein encoding nucleic acid at a high level. The promoters may be either naturally occurring promoters, hybrid or synthetic promoters. Hybrid promoters, which combine elements of more than one promoter, are also known in the art, and are useful in the present invention.

Particularly preferred promoters for expression in mammalian cells are CMV promoters. Preferred retroviral promoters are discussed below.

In a preferred embodiment, the promoter is associated with at least one copy of a nucleic acid encoding the DP-protein. Individual components encoding parts of the fusion protein, such as the dimerization protein, the protein of interest and one or more fusion partners can be inserted in a parental vector which comprises at least on suitable cloning site, preferable 3' to the promoter sequence. In a preferred embodiment, the fusion protein encoding nucleic acid is composed of individual components to generate a fusion protein such as DP-L-protein-L-DP or N-DP-L-protein-L-DP, wherein 'N' is a nuclear localization signal, 'DP' is a dimerization peptide, 'L' is a linker sequence and 'protein' is a protein of interest. As discussed in detail above, many possible combinations of nucleic acid components encoding individual components of the fusion protein to be constructed.

Generation of such vectors is performed using methods known to those in the art which are, for example, described in Sambrook et al., *Molecular Cloning: A Laboratory Manual* (New York: Cold Spring Harbor Laboratory Press, 1989) and Ausubel et al., *Short Protocols in Molecular Biology* (John Wiley & Sons, Inc., 1995). Pre-configured vectors are suitable to be included in kits. The end user of such vectors will have to insert the nucleic acid encoding a protein of interest or a library of proteins of interest into convenient cloning sites.

In another preferred embodiment, a rescue sequence is used to isolate the nucleic acid encoding the DP-protein. In this embodiment the rescue sequence may be a unique oligonucleotide sequence which serves as a probe target site to allow quick and easy isolation of the nucleic acid construct, via PCR, hybridization, or related techniques.

In addition, the vector may comprise additional elements such as a origin of replication, selection genes, etc., as is more fully described in Kriegler, in *Gene Transfer and Expression: A Laboratory Manual*, Freeman and Company, New York, (1990) and Murray, *Methods in Molecular Biology, Vol 7: Gene Transfer and Expression Protocols*, Humana Press (1991).

The nucleic acid encoding the protein of interest may be obtained from genomic DNA, cDNA, from defined oligonucleotides or from random nucleotides.

Usually the DP-proteins and DP-fusion proteins will be encoded by nucleic acids and are generated after transcription thereof and translation of the corresponding mRNA. In one preferred embodiment, concatemers of a nucleic acid encoding, for example, a DP fusion-peptide such as illustrated above ($DP_{hyd}$-$L_P$-protein$_1$-$L_P$-$DP_{hyd}$-$L_G$-$DP_{Lys}$-$L_P$-protein$_2$-$L_P$-$DP_{Glu}$) can be inserted into suitable cloning vectors (as detailed below) resulting in the generation of concatemerized DP-fusion proteins such as ($DP_{hyd}$-$L_P$-protein$_1$-$L_P$-$DP_{hyd}$-$L_G$-$DP_{Lys}$-$L_P$-protein$_2$-$L_P$-$DP_{Glu}$)$_n$, wherein n is an integer of at least 2. As will be obvious to those in the art a plurality of DP fusion protein encoding nucleic acids other than those illustrated herein, including bivalent and monovalent derivatives thereof, can be combined in suitable vectors and the corresponding DP-proteins can be made.

In one embodiment, retroviral vectors are used to express the candidate DP-proteins and the nucleic acid encoding the candidate DP-protein is generally RNA.

A particularly well suited retroviral transfection system is described in Mann et al., Cell 33:153–159 (1983); Pear et al., Proc. Natl. Acad. Sci. USA 90(18):8392–6 (1993); Kitamura et al., Proc. Natl. Acad. Sci. USA 92:9146–9150 (1995); Kinsella et al., Hum. Gene Ther. 7:1405–1413 (1996); Hofmann et al., Proc. Natl. Acad. Sci. USA 93:5185–5190 (1996); Choate et al., Hum. Gene Ther. 7:2247–53 (1996); and WO 94/19478 and PCT/US97/01019; and references cited therein, all of which are expressly incorporated by reference.

Any number of suitable retroviral vectors may be used. Preferred retroviral expression vectors include vectors based on the murine stem cell virus [MSCV; see Hawley et al., Gene Ther. 1:136–8 (1994)] and a modified MFG virus [Riviere et al., Proc. Natl. Acad. Sci. USA 92:6733–7 (1995)], and pBABE (see PCT US97/01019, incorporated by reference). Other suitable retroviral expression vectors are derived from Moloney murine leukemia virus and include vectors such as pLNCX, pLXSN, pLAPSN; a self-inactivating expression vector, such as PSIR; a bicistronic expression vector, such as pLXIN; inducible expression vectors, such as pRevTet-On, pRevTet-Off [Clontech Laboratories; see also Coffin and Varmus, in Retroviruses (Cold Spring Harbor Laboratory Press, New York, 1996)].

As described above for other vectors, retroviral vectors may include inducible and constitutive promoters. Constitutive promoters are preferred and include, but are not limited to, CMV, SV40, Srα, RSV, EF-1a, UbC and TK.

Generally, the retroviral expression vectors may include one or more selection genes (also referred to as selectable marker genes) under the control of internal ribosome entry sites (IRES), which allows for bicistronic operons and thus greatly facilitates the selection of cells expressing fusion constructs at uniformly high levels; and promoters driving expression of a second gene, placed in sense or anti-sense relative to the 5' LTR.

Selection genes allow the selection of transformed host cells containing the vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that either confers resistance to a selection agent or that encodes a marker allowing selecting the cell expressing this marker. Suitable selection agents include, but are not limited to, neomycin (or its analog G418), blasticidin S, histinidol D, bleomycin, puromycin, hygromycin B, and other drugs. Suitable marker genes, which can be inserted into a bicistronic transcriptional unit (see above) and subsequently allow the identification of host cells expressing a gene of interest include, but are not limited to, self-fluorescent markers such as green fluorescent protein, enzymatic markers such as lacZ, and surface proteins such as CD8, etc.

As described for the other vectors, the retroviral vectors may comprise a variety of transcriptional and translational regulatory sequences and at least one cloning site for the subcloning of at least one recombinant DNA fragment.

The compositions of the invention are introduced into host cells to screen for bioactive agents capable of altering the phenotype of a cell which expresses a gene of interest or protein of interest. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include CaPO$_4$ precipitation, liposome fusion, lipofectin®, electroporation, viral infection,. etc. [see Kriegler, *Gene Transfer and Expression: A Laboratory Manual* (New York: Oxford University Press, 1991); Roth, *Protein Expression in Animal Cells, Methods in Cell Biology* Vol. 43 (San Diego: Academic Press, 1994); and Murray, *Gene Transfer and Expression Protocols, Methods in Molecular Biology*, Vol. 7 (Clifton: Humana Press, 1991)].

The compositions of the invention may stably integrate into the genome of the host cell (for example, when using retroviral particles), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

As will be appreciated by those in the art, the type of cells used in the present invention can vary widely. Basically, any cell may be used, with mammalian cells being preferred, with mouse, rat, primate and human cells being particularly preferred. As is more fully described below, a screen will be set up such that the cells exhibit a selectable phenotype in the presence of a candidate DP-protein. As is more fully described below, cell types implicated in a wide variety of disease conditions are particularly useful, so long as a suitable screen may be designed to allow the selection of cells that exhibit an altered phenotype as a consequence of the presence of a candidate DP-protein within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH 3T3 cells, CHO, Cos, etc. See the ATCC cell line catalog, hereby expressly incorporated by reference.

In one embodiment, the cells may be genetically engineered, that is, contain exogenous nucleic acid (for example, encoding a target molecule) in addition to the compositions of the invention.

Once made, the compositions of the invention find use in a number of applications. The present invention provides compositions which are useful to identify, both in vivo and in vitro proteins capable of interacting with, binding to or modulating the activity of a second protein.

In a preferred embodiment the present invention provides methods and compositions to create, effectively introduce into cells and screen compounds that affect a signaling pathway. Little or no knowledge of the pathway is required, other than a presumed signaling event and an observable physiologic change in the target cell. The disclosed methods comprise an in vivo stratagem for accessing intracellular signaling mechanisms. The invention also provides for the isolation of the constituents of the pathway, the tools to characterize the pathway, and lead compounds for pharmaceutical development.

The present invention provides methods for the screening of compounds, referred to herein as DP-proteins, which are capable of altering the phenotype of cells comprising them. By "candidate DP-protein" herein is meant a DP-protein for which a function, an intrinsic property, or an interaction with a second protein is sought. While the "DP" component of candidate DP-proteins is generally not changed within a molecular library, the "protein" component of candidate DP-proteins is variable.

In one embodiment, a plurality of candidate DP-proteins is provided in form of a molecular library. The term "molecular library" herein is meant to include a plurality of different DP-proteins, a plurality of isolated different nucleic acids encoding a plurality of different DP-proteins, and a plurality of different nucleic acids which encode a plurality of different DP-proteins and which are comprised by vectors. The methods of the present invention provide for the rapid in vivo screening of molecular libraries comprising large numbers of candidate DP-proteins, wherein the 'protein' components of DP-proteins are encoded by a candidate nucleic acid, comprising either random oligonucleotides, cDNA fragments and genomic DNA. Thus, by delivering the random oligonucleotides, cDNA fragments and genomic DNA to cells, the cellular machinery generates the candidate DP-proteins. By screening the same cells, without the need to collect or synthesize in vitro the candidate DP-protein, highly efficient screening is accomplished. Thus, the present invention provides methods for screening a plurality of candidate DP-proteins, for effectors capable of altering the phenotype of a cell.

Signaling pathways in cells often involve an effector stimulus (e.g., chemokine, growth factor, hormone, etc.) that leads to a phenotypically describable change in cellular physiology. Despite the key role intracellular signaling pathways play in disease pathogenesis, in most cases, little is known about a signaling pathway other than the initial stimulus and the ultimate cellular response. When peptides are intracellularly expressed, they may modulate intracellular signaling pathways (Souroujon and Mochly-Rosen, Nat. Biotechnol. 16(10):919–24 (1998) and thus may participate in protein-protein interactions. Molecular libraries of chemical compounds or peptides were screened for effector molecules that modulate (e.g., up-regulate or down-regulate) signaling pathways. Thus constrained peptides contained in minimized proteins may also be useful in the design of agents modulating intracellular protein-protein interactions [Cunningham and Wells, Curr. Opin. Struct. Biol. 7:457462 (1997)], which may offer a novel method of regulating intracellular signaling pathways. If the peptides are expressed in live mammalian cells, for example by using retroviral vectors, they may be screened for defined changes in cellular phenotype, and the resulting active peptides may provide a route for the affinity isolation of their binding targets.

Some form of conformationally constrained peptides may be useful and even necessary in displaying peptides for intracellular combinatorial chemistry in live mammalian cells. Unlike peptides in phage display libraries, intracellular peptides may be subject to catabolism and thus preferably these peptides should be relatively inert to cellular proteases. Although intracellular peptide catabolism has not been well characterized, the ubiquitin-proteasome system is known to be involved in the degradation of proteins [Goldberg et al, Biol. Chem. 378:131–140 (1997); Hilt and Wolf, Trends Biochem. Sci. 21:96–102 (1996)], and can act as a carboxyoctapeptidase. Further proteolysis, perhaps involving aminopeptidases, can result in the degradation of peptides to amino acids [Lee and Goldberg, Trends Cell Biol. 8:397–403 (1998)]. In antigen presenting cells, short linear peptides resulting from cytoplasmic proteolysis can be removed to the endoplasmic reticulum by the peptide transporters TAP1 and TAP2 [Belich and Trowsdale, Mol. Biol. Rep. 21:53–56 (1995)].

Developing a scaffold for the intracellular display of expressed peptides which (i) is relatively inert to proteolysis resulting in enhanced intracellular stability and a higher steady state concentration of the expressed protein and (ii) which is also small enough to allow access to binding sites on proteins such as active site crevices may be very useful. The compact nature of this scaffold should decrease the flexibility of the expressed protein and decrease the conformational entropy, effectively increasing the concentration of individual conformers. This and the increased stability to proteolysis should in turn make these scaffolds (e.g., when used as peptide libraries) more likely to contain active proteins, since the higher concentrations should allow saturation of weaker binding interactions. This benefits screening protocols to detect bioactive peptides, by allowing phenotypic selection of lower affinity peptides, and thus allowing more bioactive peptides to be detected. Such features of enhanced proteolytic stability and diminished conformational entropy may also make the more compact structure more attractive as a potential therapeutic. Addition of specific short sequences to the N- and C-terminus of the peptide may be useful for enhancing the above properties. A loop structure [Leszczynski and Rose, Science 234:849–855 (1986)] may be of particular interest, since loops are globular and compact, are common on protein surfaces, and may be frequently involved in protein function and protein-protein interactions.

In a preferred embodiment, the compositions of the invention are used to screen for candidate bioactive agents; that is the test protein within the DP-protein (see above) is a candidate bioactive agent. The candidate DP-proteins, as part of a molecular library, are introduced into suitable host cells to screen for DP-proteins, capable of altering the phenotype of the host cell, harboring or expressing such a candidate DP-protein. If necessary, the cells are treated to conditions suitable for the expression of genes encoding the candidate DP-proteins (for example, when inducible promoters are used), to produce the candidate expression products.

In a preferred embodiment, a first plurality of cells is screened. That is, the cells into which a molecular library is introduced, which provides candidate DP-proteins, are screened for an altered phenotype. Thus, in this embodiment, the effect of the candidate DP-protein is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within this cellular library contains a member of the molecular library, i.e. a different candidate DP-protein or a different DP-protein encoding nucleic acid, although as will be appreciated by those in the art, some cells within the cellular library may not contain a member of the molecular library, and some may contain more than one. When methods other than retroviral infection are used to introduce the candidate DP-protein into a plurality of cells, the distribution of candidate nucleic acids within the individual cell members of the cellular library may vary widely, as it is generally difficult to control the number of nucleic acids which enter a cell during electroporation, etc.

In a preferred embodiment, the molecular library is introduced into a first plurality of cells, and the effect of the expressed candidate DP-protein is screened in a second or third plurality of cells, different from the first plurality of cells, i.e. generally a different cell type. That is, the effect of the candidate DP-protein is due to an extracellular effect on a second cell; i.e. an endocrine or paracrine effect. This is done using standard techniques. The first plurality of cells may be grown in or on one media, and the media (referred to as "conditioned media") is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

Thus, the methods of the present invention comprise introducing a molecular library of randomized candidate nucleic acids into a plurality of cells, generating a cellular library. Each of the nucleic acids comprises a different, generally randomized, nucleotide sequence, encoding a different DP-protein. The plurality of cells is then screened, as is more fully outlined below, for a cell exhibiting an altered phenotype. The altered phenotype is due to the presence of a DP-protein.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, mRNAs, proteins, lipids, hormones, cytokines, or other molecules; changes in the equilibrium state (i.e. half-life) of one or more RNAs, mRNAs, proteins, lipids, hormones, cytokines, or other molecules; changes in the localization of one or more RNAs, mRNAs, proteins, lipids, hormones, cytokines, or other molecules; changes in the bioactivity or specific activity of one or more RNAs, mRNAs, proteins, lipids, hormones, cytokines, receptors, or other molecules; changes in the secretion of ions, cytokines, hormones, growth factors, proteins, or other molecules; alterations in cellular membrane potentials, polarization, integrity or transport; changes in infectivity, susceptibility, latency, adhesion, and uptake of viruses and bacterial pathogens; etc.

By "capable of altering the phenotype" or grammatical equivalents, herein is meant that a candidate DP-protein can change the phenotype of the cell in some detectable and/or measurable way.

The altered phenotype may be detected in a wide variety of ways, as is described more fully below and in PCT/US97/01019, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; monitoring changes in gene expression within a target cell, etc. In some cases, as is more fully described herein, the altered phenotype is detected in the cell in which the molecular library comprising the randomized nucleic acid or randomized proteins was introduced; in other embodiments, the altered phenotype is detected in a second cell which is responding to some molecular signal from the first cell.

In a preferred embodiment, upon its translocation into the nucleus, the DP-protein modulates gene expression causing an increase or a decrease of expression of a target gene. In one embodiment, a transcriptional activation protein binds to the DP-protein and thus either may be inactivated or prevented from activating its target gene. In this embodiment, the DP-protein comprises a protein which has an affinity to the target transcriptional activator, for example the HIV tat protein. In another embodiment, DP-protein may lead to an increase expression of a target gene, by virtue of comprising a protein component which has an affinity to a transcriptional repressor. Upon binding of the transcriptional repressor to the DP-protein, it either may be inactivated or prevented from binding to its target gene and thus leading to a higher expression of the gene of interest.

In a preferred embodiment, once a cell with an altered phenotype is detected, the cell is isolated from the plurality of cells which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the candidate nucleic acid encoding the candidate DP-protein and/or the candidate DP-protein is isolated from the cell with an altered phenotype. This may be done in a number of ways. In a preferred embodiment, primers complementary to DNA regions common to the vector, or to specific components of the molecular library such as a rescue sequence, defined above, are used to "rescue" the unique random nucleic acid encoding the candidate DP-protein. Alternatively, the candidate DP-protein is isolated using a rescue sequence which is operably linked to the candidate DP-protein (as described above). Thus, for example, rescue sequences comprising epitope tags or purification sequences may be used to pull out the bioactive agent, using immunoprecipitation or affinity columns. In some instances, as is outlined below, this may also pull out the primary target molecule, if there is a sufficiently strong binding interaction between the bioactive agent and the target molecule. Alternatively, the peptide may be detected using mass spectroscopy.

Once rescued, the sequence of the candidate nucleic acid encoding the candidate DP protein and/or the sequence of the candidate DP-protein is determined. This information can then be used in a number of ways.

Often, when genomic libraries or cDNA libraries or DNA fragments obtained thereof are employed in the screening method outlined herein (i.e., when they are used to encode candidate DP-proteins) the nucleic acid sequence encoding the test protein is not full-length, i.e., the nucleic acid sequence does not encode the complete test protein. By "full-length" cDNA, gene, mRNA, RNA or grammatical equivalents herein is meant any nucleic acid which encodes a complete protein as it is encoded by its corresponding cellular genetic locus. In addition to the complete protein encoding sequence, a full-length cDNA, gene, mRNA or RNA may optionally contain 5' and 3' untranslated nucleic acid sequences. The complete protein may include amino acids incorporated by translation of the corresponding mRNA, that may subsequently be eliminated from the native protein, e.g. secretory signal peptide sequences or sequences involved in protein splicing and protein processing. By "full-length protein" or grammatical equivalents herein is meant a protein encoded by a full-length cDNA, gene, RNA or mRNA. As appreciated by those in the art, full-length proteins may include posttranslationally modifications, including, but not limited to, signal peptide cleavage, protein splicing, protein precursor processing, glycosylation, and the like. Accordingly, a "partial cDNA", "partial gene", "partial mRNA", "partial RNA" or a "partial protein" or grammatical equivalents are meant to indicate a cDNA, gene, mRNA, RNA or a protein which represents a fragment of a full-length cDNA, gene, mRNA, RNA or a protein. Accordingly, in a preferred embodiment, the determined nucleic acid sequence information of the rescued partial protein will be used to isolate the full-length coding sequence of the DP-protein. The isolation and characterization of a full-length coding sequence using a partial sequence information is well known in the art.

In a preferred embodiment, the nucleic acid encoding the candidate DP-protein, or a nucleic acid encoding a full-length version thereof or any fragment of the full-length version, or a derivative of the candidate DP-protein (see below), is reintroduced into the host cells, to verify the originally observed altered phenotype of the cell. These cells may be the same as in the original screening experiment or different. This may be done using retroviruses, or alternatively using fusions to the HIV-1 Tat protein and analogs and related proteins, which allows very high uptake into target cells. See for example, Fawell et al., Proc. Natl. Acad. Sci. USA 91:664–8 (1994); Frankel and Pabo, Cell 55:1189–93 (1988); Savion et al., J. Biol. Chem. 256:1149–54 (1981); Derossi et al., J. Biol. Chem. 269:10444–50 (1994); and Baldin et al., EMBO J. 9:1511–7 (1990), all of which are incorporated by reference.

In a preferred embodiment, a recombinant DP-protein is generated (as outlined further below) and used to confirm the alteration of the phenotype of a target cell. This is a preferred embodiment, when the alteration of a phenotype was observed in a second or third plurality of cells as described above. That is, the effect of the candidate DP-protein may be due to its secretion from a first cell, wherein it was generated, followed by its binding to a cellular receptor on the second cell (i.e., different cell) or internalization by a different means and subsequently exerting its effect in or on this second cell. In this embodiment, the recombinant DP-protein or a derivative thereof is provided to the second cell and an alteration of phenotype is monitored.

In a preferred embodiment, the nucleic acids encoding the DP-protein or a derivative thereof (referred to herein also as protein of interest) are used to express the respective recombinant protein. A variety of expression vectors, including viral and non-viral expression vectors can be made which are useful for recombinant protein expression in a variety of systems, including, but not limited to, yeast, bacteria, archaebacteria, fungi, insect cells and animal cells, including mammalian cells.

The protein of interest may also be expressed as a fusion protein, including fusions to fusion partners, as outlined before, or fusions to other protein sequences. Recombinant proteins of interest are produced by culturing host cells into which nucleic acids encoding the protein of interest (generally as an expression vector) is introduced, under the appropriate conditions that induce or cause expression of the recombinant protein.

In a preferred embodiment, the recombinant protein is purified following expression. Numerous suitable methods for recombinant protein expression, including generation of expression vectors, generation of fusion proteins, introducing expression vectors into host cells, protein expression in host cells, and purification methods are known to those in the art and are described, for example, in the following textbooks: Ausubel et al., *Short Protocols in Molecular Biology* (John Wiley & Sons, Inc., 1995); O'Reilly et al., *Baculovirus Expression Vectors: A Laboratory Manual* (New York: Oxford University Press, 1994); Kriegler, *Gene Transfer and Expression: A Laboratory Manual* (New York: Oxford University Press, 1991); and Deutscher, *Guide to Protein Purification, Methods in Enzymology Vol.* 182 (San Diego: Academic Press, Inc., 1990).

In a preferred embodiment, either the DP-protein or the nucleic acid encoding it is used to identify target molecules, i.e. the molecules with which the DP-protein interacts. As will be appreciated by those in the art, there may be primary target molecules, to which the DP-protein binds or acts upon directly, and there may be secondary target molecules, which are part of the signaling pathway affected by the DP-protein.

In a preferred embodiment, the DP-protein is used to pull out target molecules. For example, as outlined herein, if the target molecules are proteins, the use of epitope tags or purification sequences operably linked to the DP-protein can allow the purification of primary target molecules via biochemical means [co-immunoprecipitation, affinity columns, etc., for example, see Deutscher, *Guide to Protein Purification, Methods in Enzymology Vol.* 182 (San Diego: Academic Press, Inc., 1990); Harris and Angal, *Protein Purification Methods: A Practical Approach* (Oxford: IRL Press at Oxford University Press, 1994); Harris and Angal, *Protein Purification Applications: A Practical Approach* (Oxford: IRL Press at Oxford University Press, 1990)]. Alternatively, the recombinant DP-protein, when expressed in bacteria and purified, can be used as a probe against a cDNA expression library made from mRNA of the target cell type. Or, DP-proteins can be used as a "bait" protein (e.g., when a DP-protein of defined sequence is employed in a screening to identify unknown binding proteins) or as a "test" protein (e.g., when a known protein is employed as a bait and screened against a molecular library comprising candidate DP-proteins) in either yeast or mammalian two or three hybrid systems (e.g., see Fields and Song, Nature 340:245–6 (1989); Vasavada et al., Proc. Natl. Acad. Sci. USA 88:10686–90 (1991); Fearon et al., Proc. Natl. Acad. Sci. USA 89:7958–62 (1992); Dang et al., Mol. Cell. Biol. 11:954–62 (1991); Chien et al., Proc. Natl. Acad. Sci. USA 88:9578–82 (1991); Luo et al., Bio/Techniques 22(2):350–352 (1997) and U.S. Pat. Nos. 5,283,173, 5,667,973, 5,468,614, 5,525,490, and 5,637,463). Such interaction cloning approaches have been very useful to isolate DNA-binding proteins and other interacting protein components. The DP-protein(s) can be combined with other pharmacologic activators to study the epistatic relationships of signal transduction pathways in question. It is also possible to synthetically prepare labeled DP-protein or a derivative thereof and use it to screen a cDNA library expressed in bacteriophage, bacteria or eukaryotic cells for those cDNAs which bind the DP-protein or its derivative. Furthermore, it is also possible to use cDNA cloning via retroviral libraries to "complement" the effect induced by the DP-protein. In such a strategy, the DP-protein would be required to be stoichiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified and validated, secondary target molecules may be identified in the same manner, using the primary target as the "bait". In this manner, signaling pathways may be elucidated. Similarly, bioactive agents specific for secondary target molecules may also be discovered, to allow a number of bioactive agents to act on a single pathway, for example for combination therapies.

In a preferred embodiment, a molecular library of recombinant DP-proteins is used in in vitro binding assays to identify member that are capable of binding to a selected target protein, e.g., a receptor, a ligand, an enzyme, etc.

Generally, in a preferred embodiment of the methods herein, a target protein (which can be a recombinant protein or a naturally occurring protein) is non-diffusably bound to an insoluble support having isolated sample receiving areas (e.g. a microtiter plate, an array, etc.). The insoluble supports may be made of any composition to which the target protein can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the target protein is not crucial so long as it is compatible with the reagents and overall methods of the invention, maintains the characteristics of the target protein and is nondiffusable. The target protein may be either bound directly to the insoluble support (e.g. via cross-linking) or indirectly (e.g., via antibody, other protein or nucleic acid, etc.). Preferred methods of binding include the use of antibodies (which do not sterically block the protein-protein interaction surface for the test protein and preferably are directed against a tag polypeptide which may be incorporated into the recombinant bait protein), direct binding to "sticky" or ionic supports, chemical crosslinking, etc. Following binding of the target protein, excess unbound material is removed by washing. The sample receiving areas may then be blocked through incubation with bovine serum albumin (BSA), casein or other innocuous protein.

A molecular library comprising a plurality of recombinant DP-proteins is added to the binding assay. The binding assay is performed at any temperature which facilitates optimal binding, typically between 4° C. and 40° C. Incubation periods are selected for optimal binding, but are also optimized to facilitate high throughput screening. Typically between 0.1 and 1 hour is sufficient. Determination of the binding of DP-proteins to the target protein may be done using a wide variety of assays, including labeled in vitro protein-protein binding assays, electrophoretic mobility shift assays (EMSA), immunoassays for protein binding, functional assays (phosphorylation assays, etc.) and the like. (e.g., see Harlow and Lane, *Antibodies: A Laboratory Manual* (New York, Cold Spring Harbor Laboratory Press, 1988) and Ausubel et al., *Short Protocols in Molecular Biology* (John Wiley & Sons, Inc., 1995).

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive agent is found, the undesirable effect may be reduced or eliminated. Alternatively, normally desirable consequences may be reduced or eliminated, with an eye towards elucidating the cellular mechanisms associated with the disease state or signaling pathway. These screening methods are outlined in PCT/US97/01019, hereby incorporated by reference.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

Novel Peptides Which Form Observable Dimers Under Harsh Conditions.

Figure 3A:
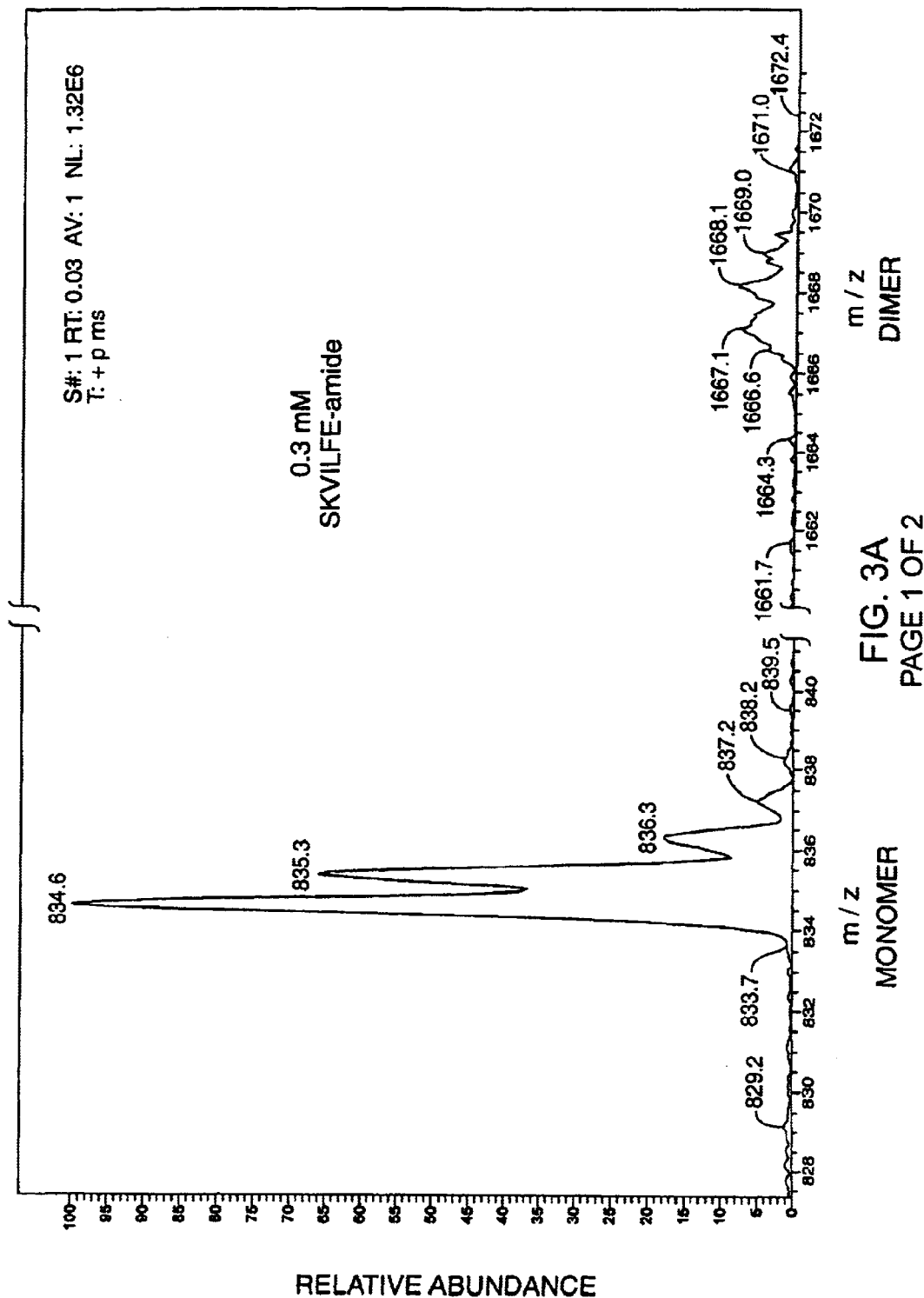
FIGS. 3A and 3B show that novel peptides form observable dimers.
Figure 3A:
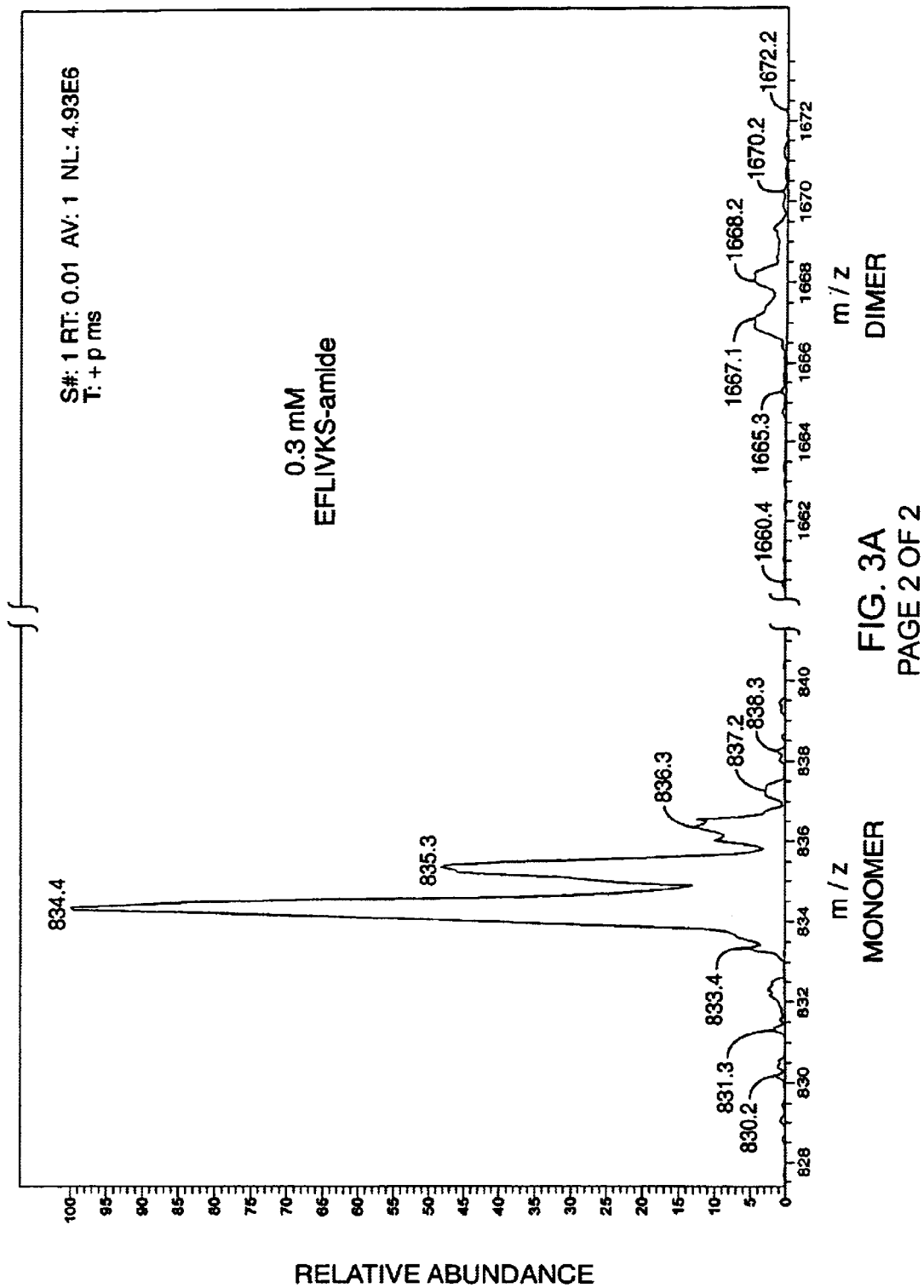
Figure 3B:
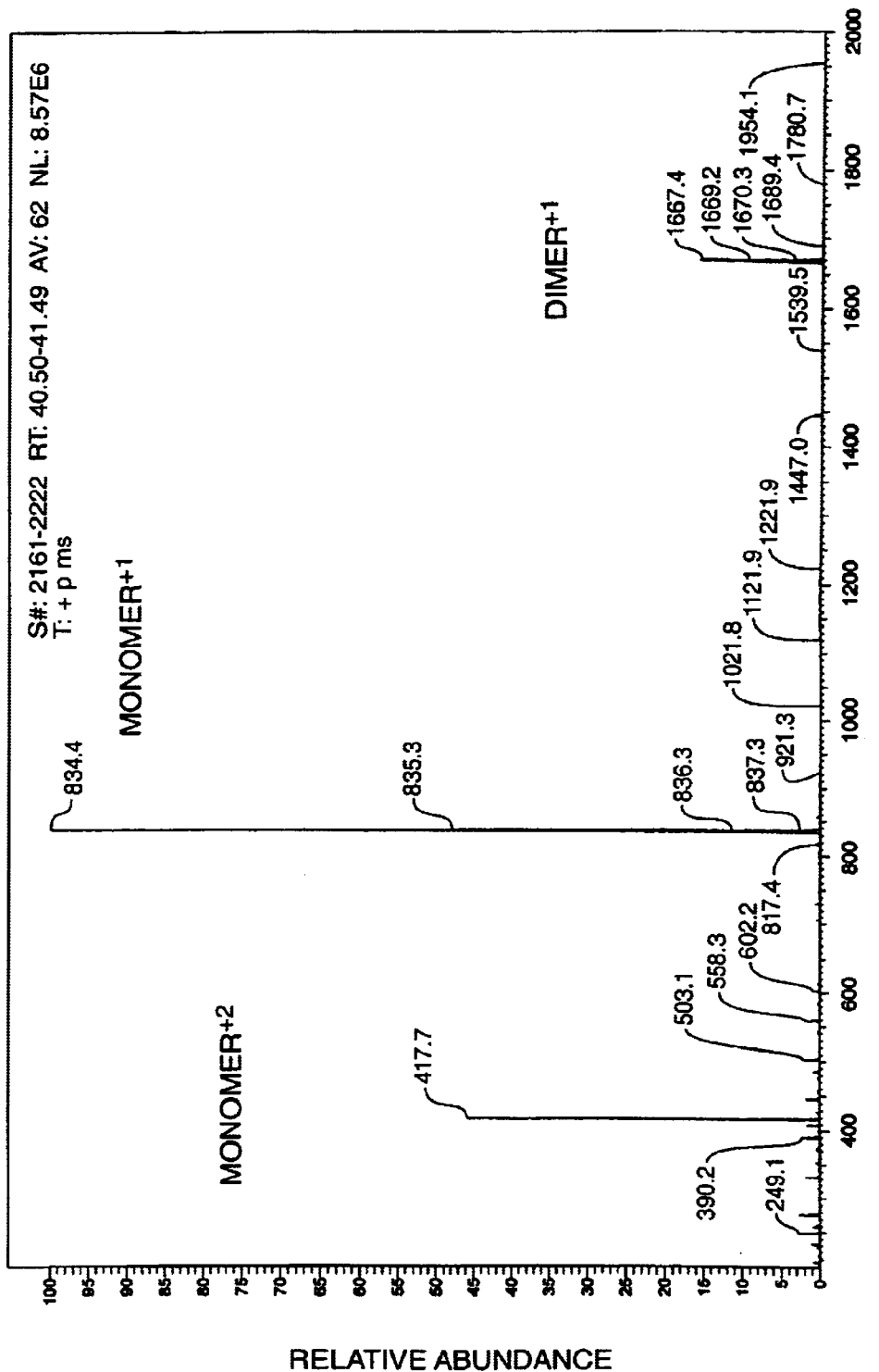

Upon infusion into the electrospray source of a Finnigan LCQ ion trap mass spectrometer of a $3\times10^{-4}$ M pH 6.4 solution of EFLIVKS-amide, this peptide appears to self-associate to form dimers (FIG. 3A), detected at exactly two times the monomer molecular weight in the gas phase, after surviving an inlet capillary temperature of 210° C. and harsh electrospray conditions, and thus would be expected to dimerize at significantly lower concentrations in aqueous solution. The peptide also forms dimers (also detected by mass spectrometry) when eluted off a C18 reversed phase column at pH ~2.5 in ca. 25% acetonitrile (FIG. 3B). Comparison of its dimerization in FIG. 3A with that of the test peptide SKVILFE (which forms dimers in the range of $10^{-13}$ M in aqueous solution (Bodenmuller et al.; supra), when both are continuously infused by an electrospray interface into an ion trap mass spectrometer, suggests that both peptides dimerize to a similar extent (within a factor of 10 or so). This suggests that EFLIVKS may dimerize in aqueous solution at very low concentrations. The dimerization of EFLIVKS cannot be predicted from dimerization of SKVILFE since reversed sequences are often used as inactive controls for bioactive peptides.

Figure 4:
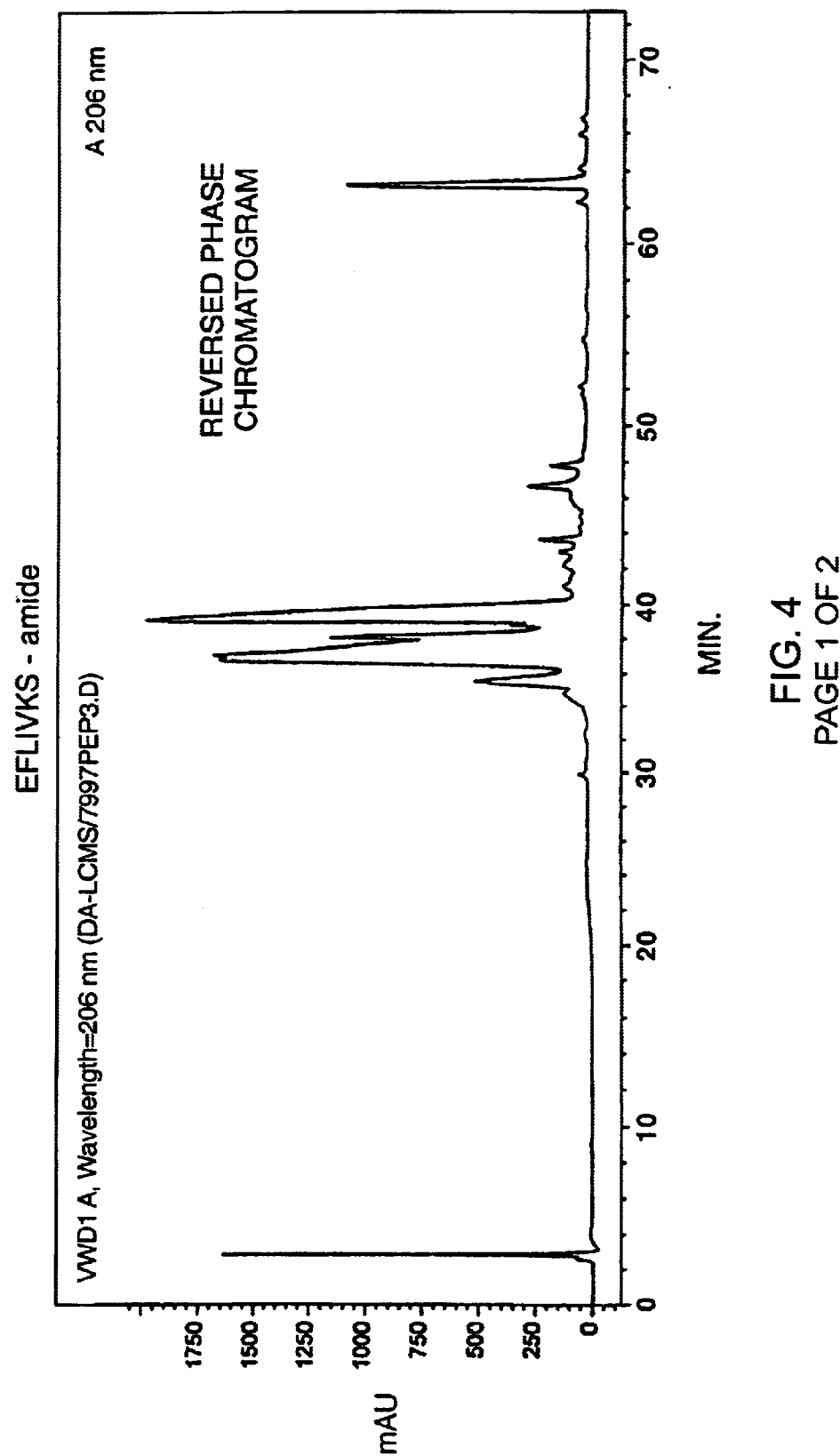
FIG. 4 shows LC/MS examination of the crude synthesis products from an all-single coupled fmoc synthesis of EFLIVKS-amide, for shorter sequences which can dimerize after electrospray ionization.
Figure 4:
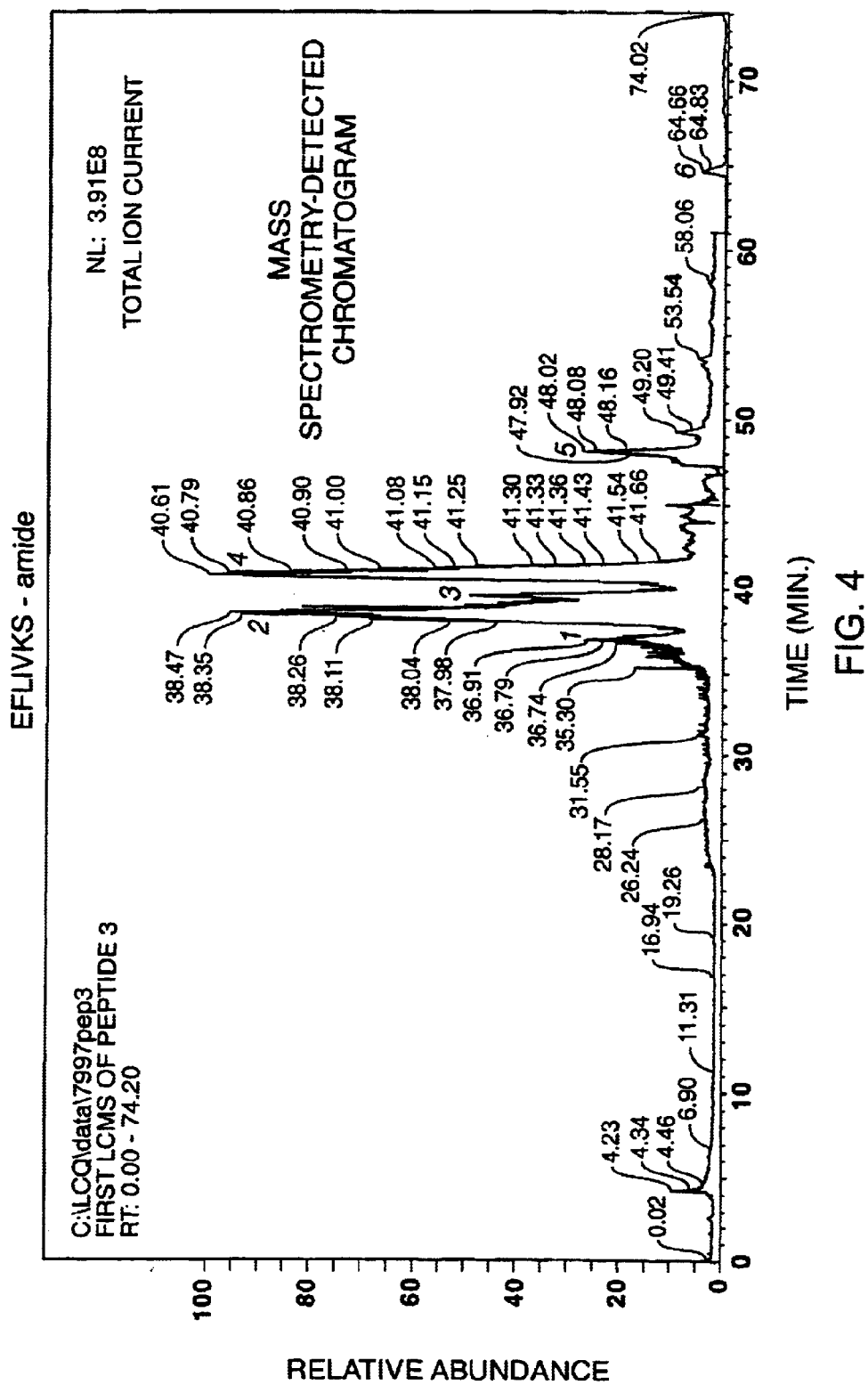

LC/MS examination of the crude synthesis products from an all-single coupled fmoc synthesis of EFLIVKS-amide, for shorter sequences which can dimerize after electrospray ionization is shown in FIG. 4. HPLC elution was with a gradient of 99.9% water-0.1% TFA to 99.9% acetonitrile-0.1% TFA. Dimers of the following truncated sequences were detected by mass spectrometry with the percent acetonitrile in parentheses, all at ~pH 2.5: peak 1, LIVKS-amide (23.5%), monomer m/z=705.3, dimer m/z=1409.3; peak 4: EFLIVKS-amide (25%), monomer m/z=834.4, dimer m/z=1667.3; and peak 5, EFLIVK-amide (32%), monomer m/z=747.4, dimer m/z=1493.1. These results suggest that the N-terminal EF and C-terminal S can be deleted without abolishing dimerization.

Examination of a peptide designed to form a short beta sheet, VSIKFEL, shows that upon elution from a C18 reversed phase column with mass spectrometry detection, the dimeric form of the peptide (m/z=1667.5) is detected in addition to the monomeric form (m/z=834.5) after electrospraying into the ion trap. This suggests that this peptide, which contains alternating hydrophilic and hydrophobic residues and thus may form a beta sheet, can also form stable dimers.

EXAMPLE 2

EFLIVKS can Form Compact Proteolytically Resistant Structures When Added to the N- and C-Terminus of a Test 18mer Polypeptide.

Figure 5A:
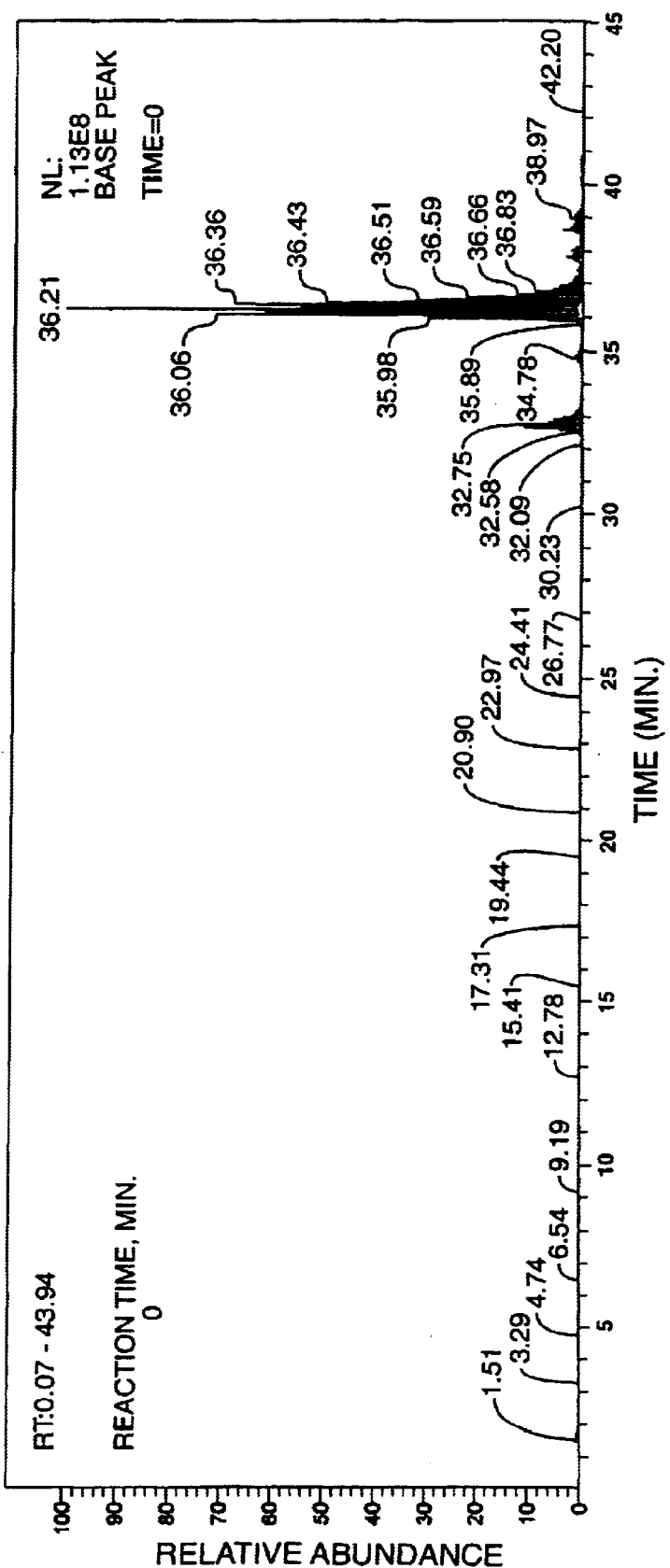
FIGS. 5A, 5B, and 5C show proteolytically resistant structures.
Figure 5A:
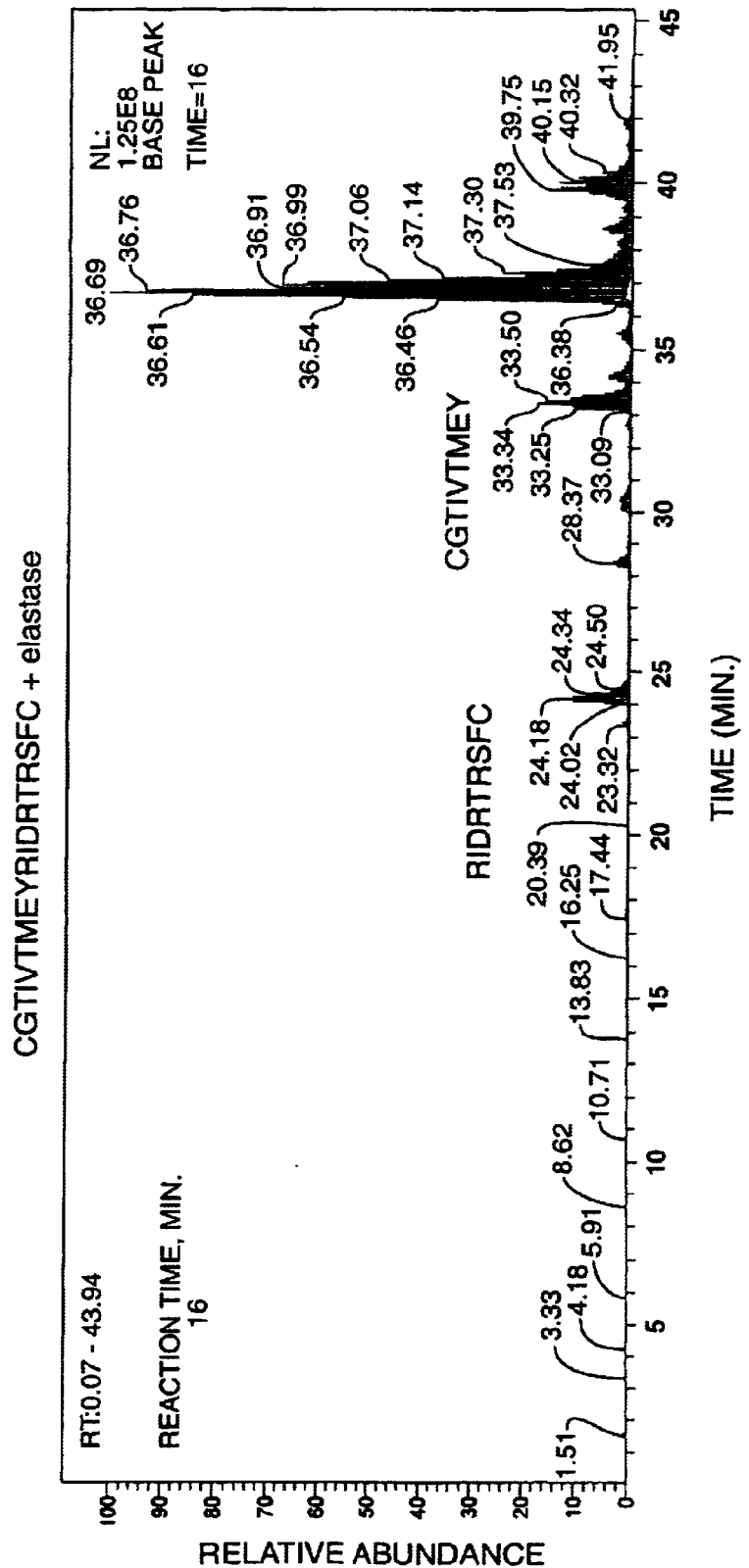
Figure 5A:
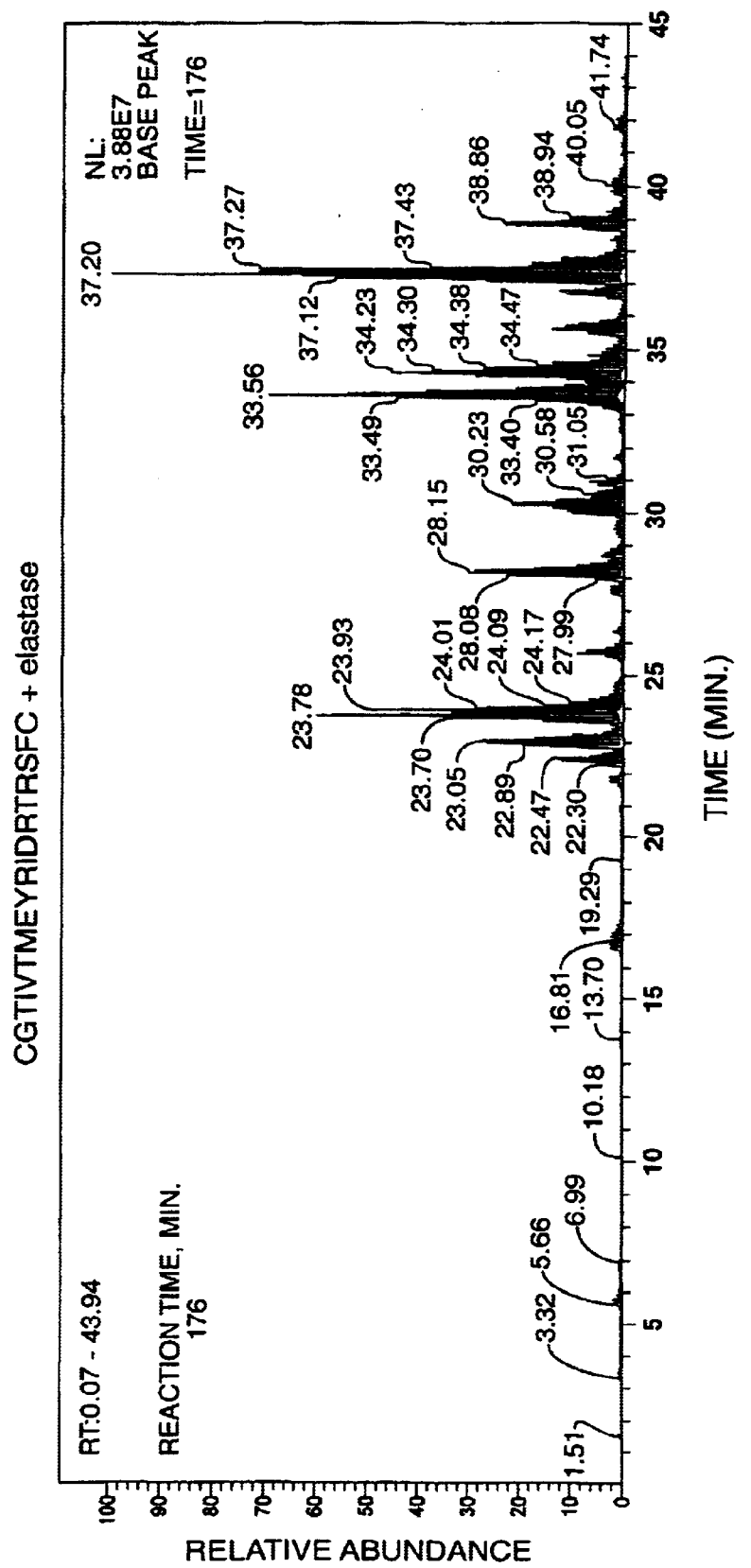
Figure 5B:
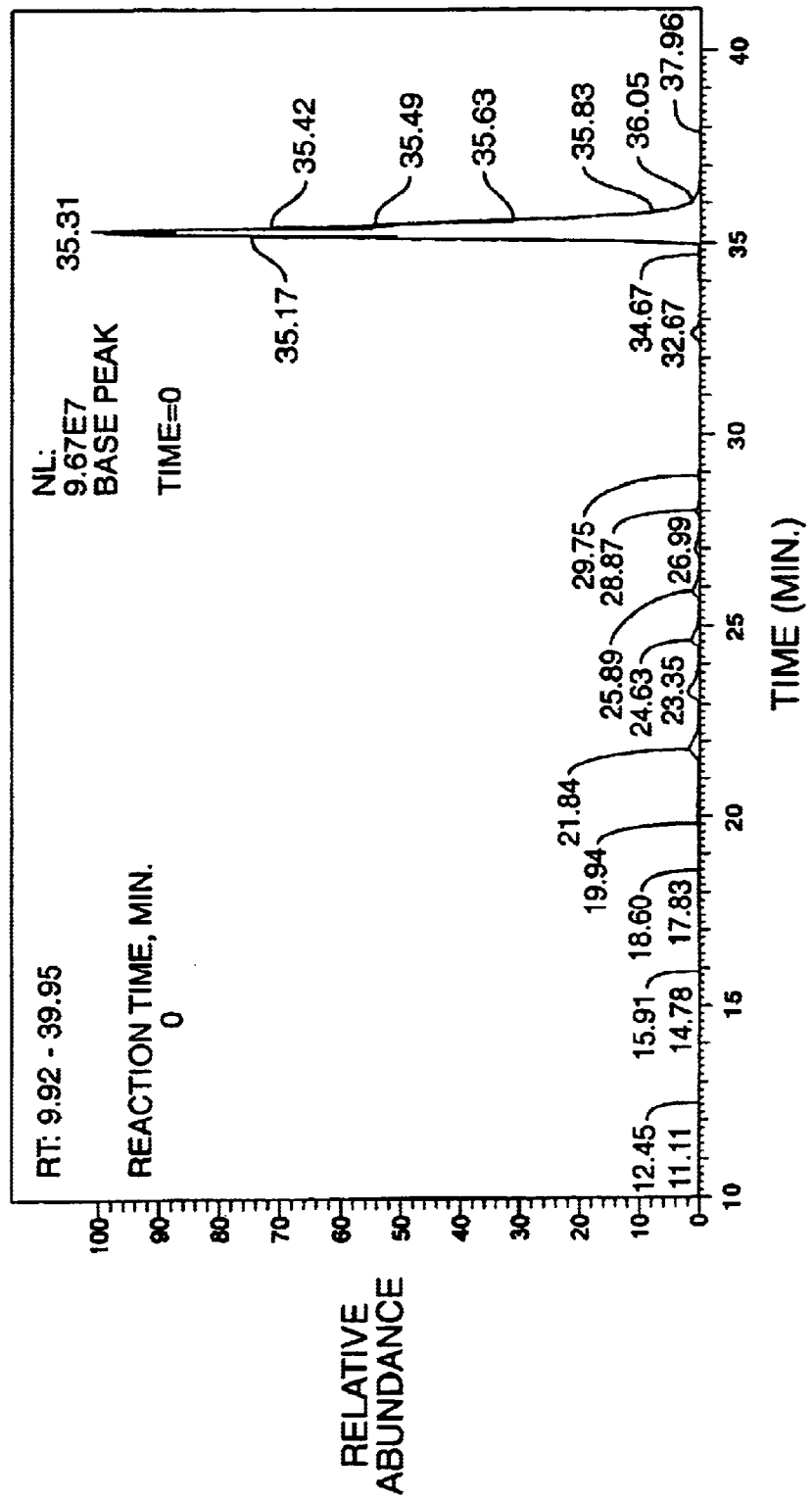
Figure 5B:
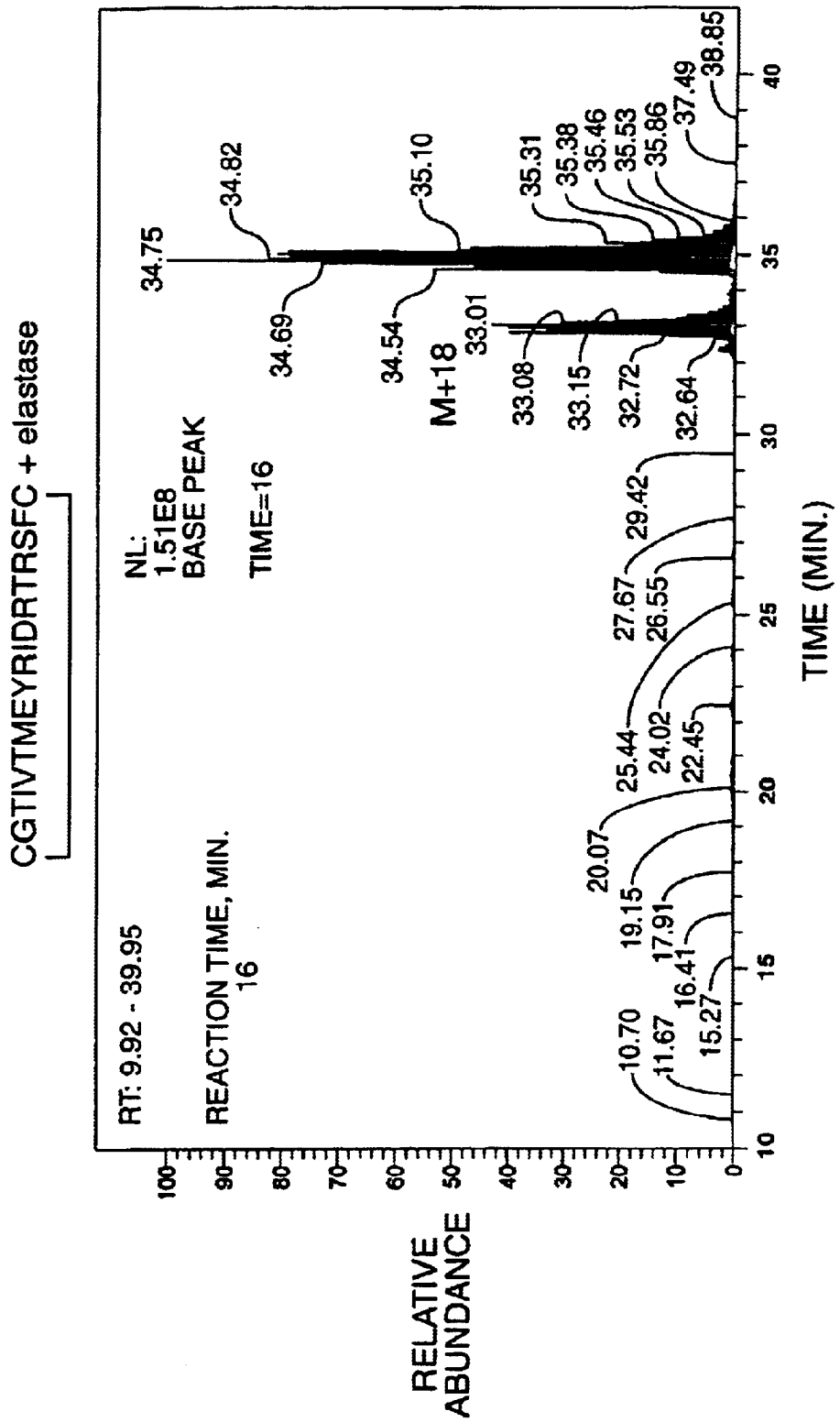
Figure 5B:
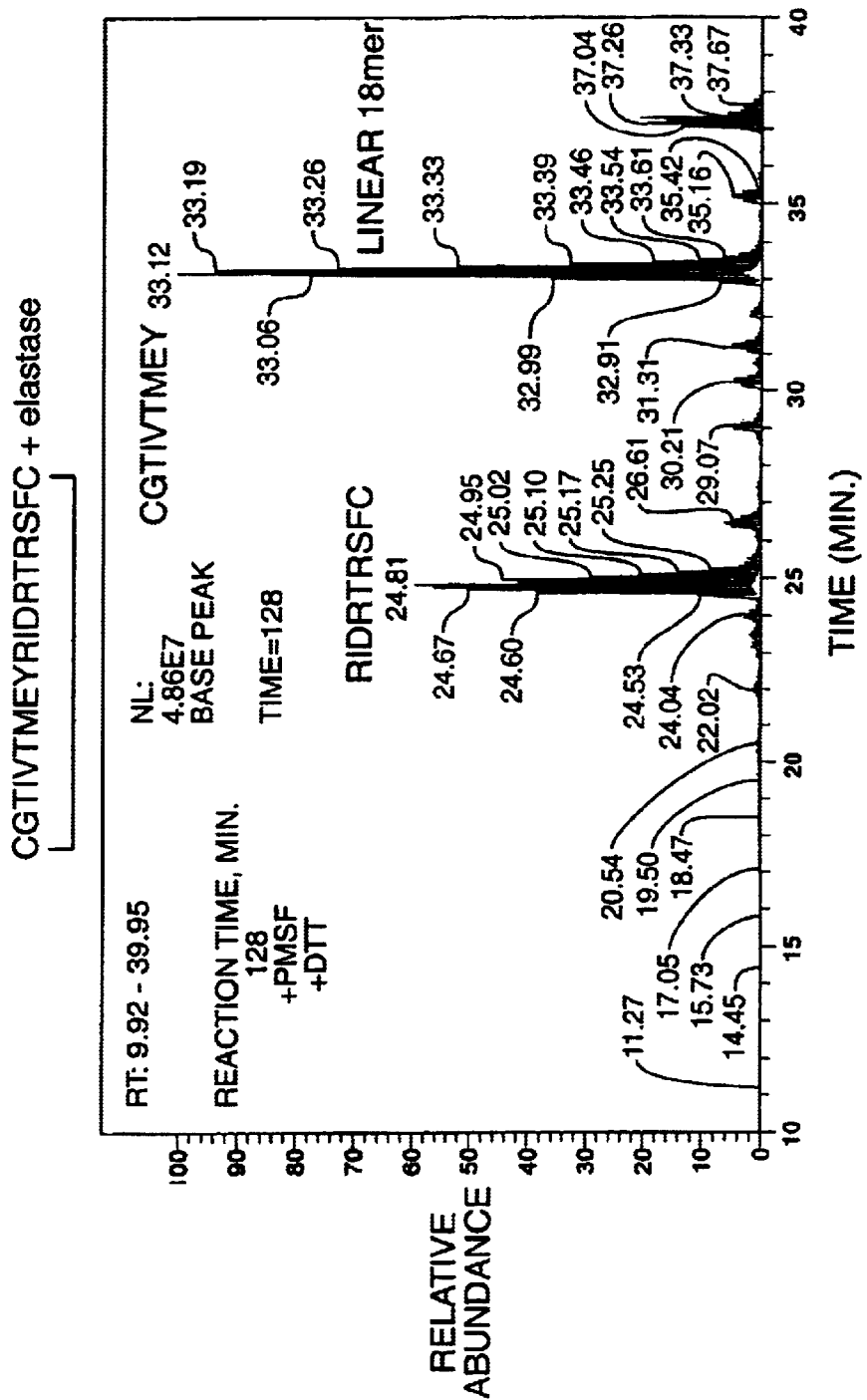
Figure 5C:
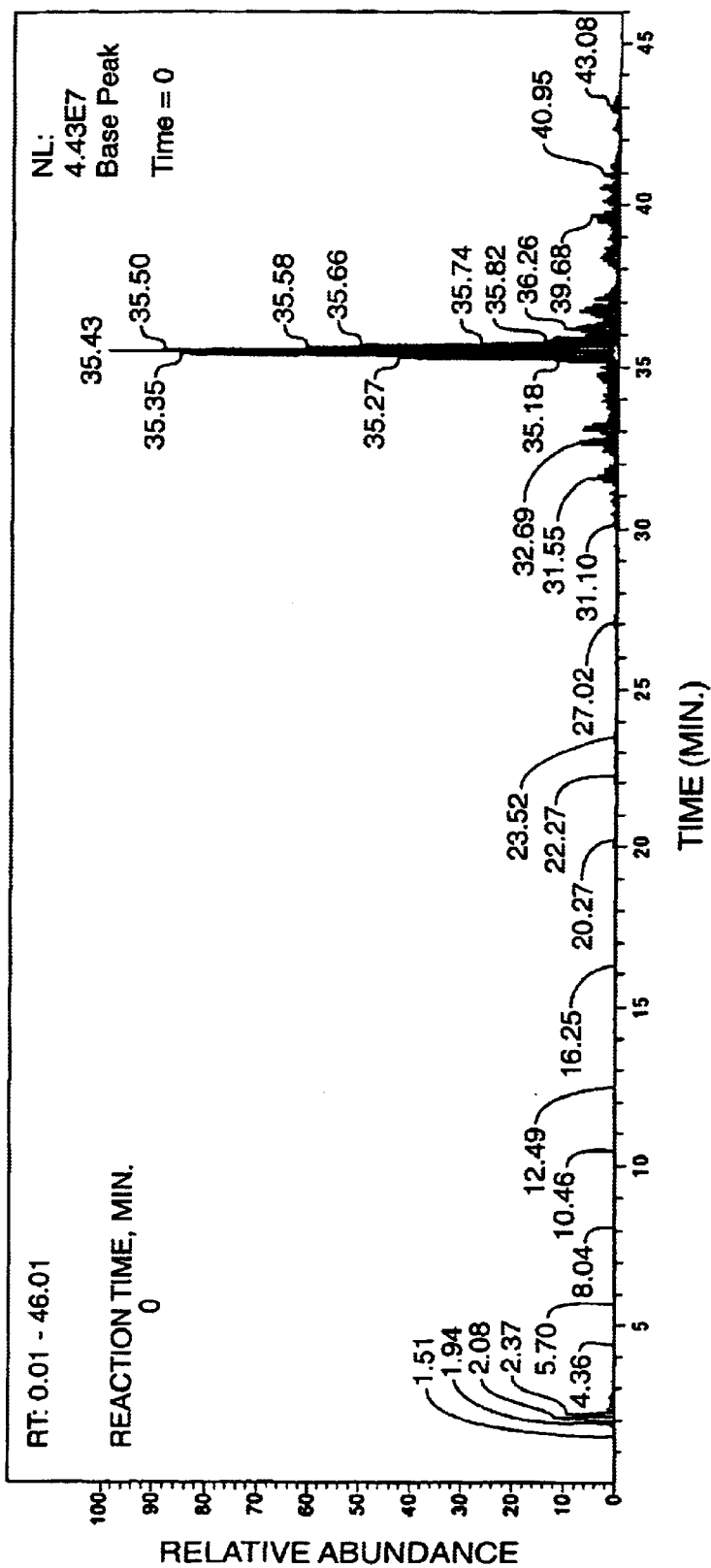
Figure 5C:
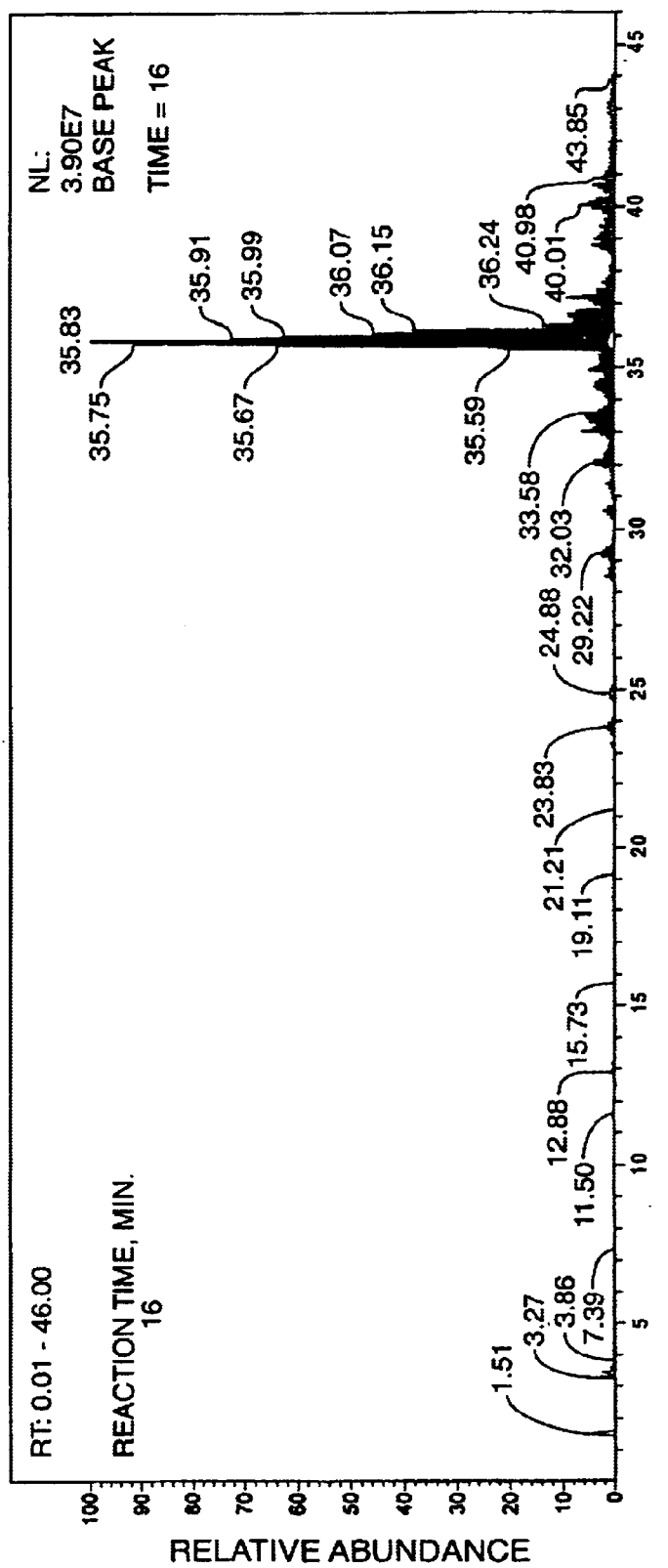
Figure 5C:
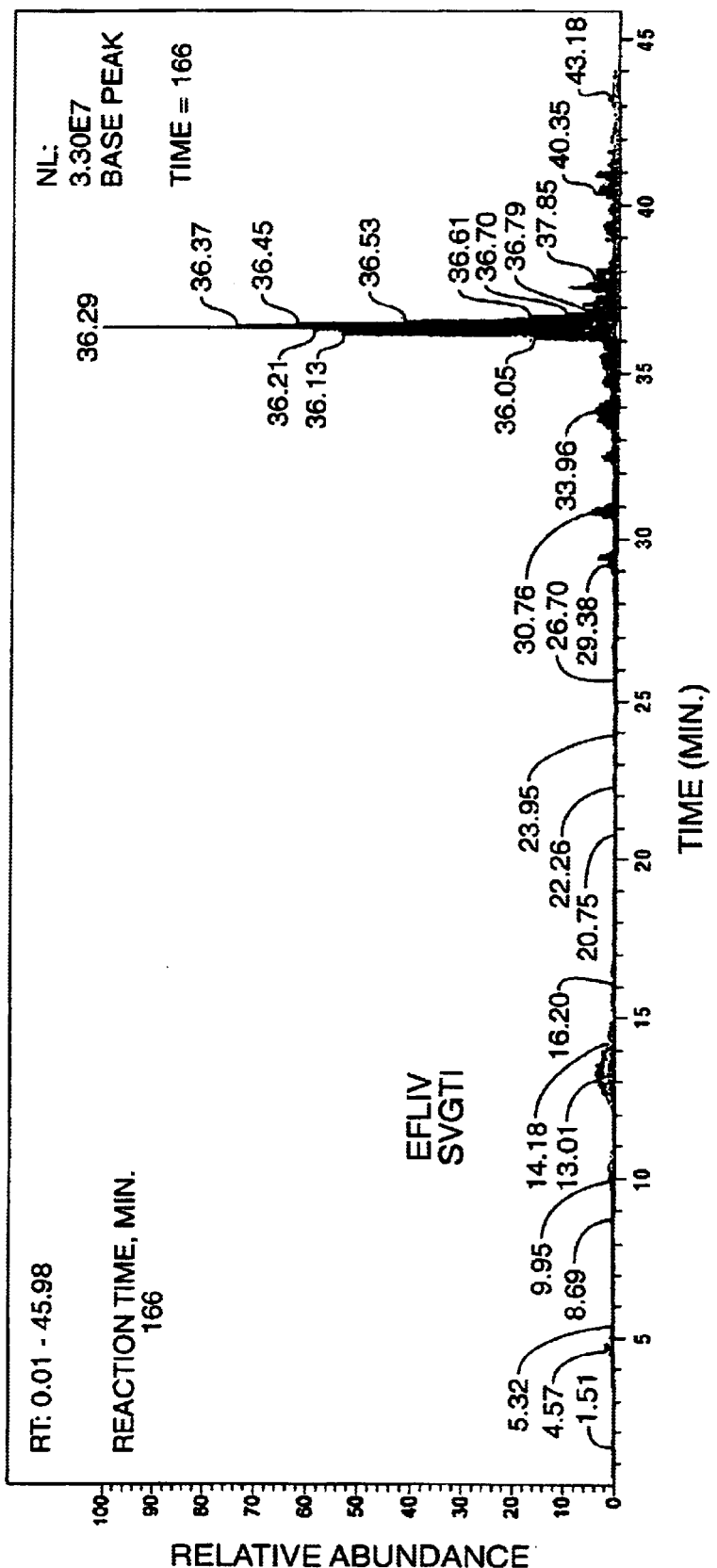

The peptide EFLIVKS, when fused to both the N- and C-terminus of a test 18mer polypeptide, can form a compact structure of this polypeptide (referred to herein also as peptide 1). The 18mer polypeptide sequence is VGTIVTMEYRIDRTRSFV, derived from the barley c2-chymotrypsin inhibitor [Leatherbarrow and Salacinski, Biochemistry 30:10717–21 (1991)]. The analog of this peptide containing an N-and C-terminal cysteine, in both cases substituted for valine, is thought to fold into a similar compact structure to the loop present in barley chymotrypsin inhibitor-2. Such a compact structure should be a poor substrate for proteases such as elastase, and in fact has been proposed as an inhibitor of elastase, chymotrypsin, and two variants of subtilisin. This disulfide-cyclized analog has been synthesized and tested by us, and is in fact a poor protease substrate, but a substrate nonetheless, and not an inhibitor. The linear peptide CGTIVTMEYRIDRTRSFC is a good substrate for elastase, with ca. 15 peptides produced after a 3 hour incubation (FIG. 5A), with the proteolysis being monitored by reversed phase hplc coupled to mass spectrometry detection and identification of the proteolytic fragments. The same peptide with a disulfide bond between the two cysteines is also a substrate for elastase, but with fewer peptide products, and the major initial cleavage occurring after the tyrosine (FIG. 5B). Fusion of the dimerizer EFLIVKS onto both the N- and C-terminus (EFLIVKS-VGTIVTMEYRIDRTRSFV-EFLIVKS-amide) creates a more proteolytically resistant construct (FIG. 5C), with little proteolysis evident after almost 3 hours, and very minor amounts of a number of different cleavage products.

EXAMPLE 3

Examination of the Low Energy Conformers of Peptide 1.

To examine the structural nature of the compact construct of peptide 1, low energy conformers were obtained by a high temperature molecular dynamics-simulated annealing protocol similar to that published by Nilges et al. Protein Engineering 2:27–38 (1988), as implemented in Discover 95. Structures were saved every 2 psec (from different trajectories lasting from 400 psec to 1400 psec at 900 K), cooled to 300 K over 5 ps, and minimized using a distance-dependent dielectric constant (varying linearly between $\epsilon=80$ at 80 Å to $\epsilon=1$ at 1 Å separation) with 200 steps of the steepest descent algorithm, then with as many steps as necessary using the conjugate gradient algorithm to give a maximum derivative of less than 0.001 kcal/A. The resulting low energy structures were collected and compared from trajectories starting from a) peptide 1, with the 18mer polypeptide started from its conformation present in barley chymotrypsin inhibitor 1, [McPhalen and James, Biochemistry 26:261–269 (1987)], and subsequently minimized using Discover 2.9.5, attached to the two dimerizers minimized from an extended conformation;

b) structures derived from a continuation of the trajectory in a) starting from the last structure, but with the trajectory modified by the use of a different dseed (different initial velocities);

c) a continuation of the trajectory in b) with a third dseed;

d) a trajectory starting as in a) except with the dimerizers forced into a starting beta sheet structure;

e) a trajectory starting as in a) except with the dimerizers forced into a starting right handed alpha helical conformation f) a trajectory starting from a fully extended peptide 1.

All structures within 20 kcal/mole of the lowest energy structure from trajectories a–f were collected and compared. FIG. 6 shows an overlay of the 45 lowest energy structures (only the peptide backbone is shown) from all of the trajectories, after a least-squares alignment of the peptide backbones. All structures when examined individually appear compact. Examination of the backbone conformations suggests that the 18mer polypeptide folds onto the surface of the dimerizers in different ways. Space filling models suggest that the resulting low energy structures are well-packed. This suggests that for polypeptide lengths on the order of 18 residues, a library of these constructs may be a library of very small proteins or compact structures. The relatively small size of these mini-proteins should allow facile nmr structure determination and thus the establishment of structure-activity relationships. These compact low energy conformers are also consistent with the observed inertness of this construct to elastase.

EXAMPLE 4

Estimation of the Affinity of the Folding Peptides Attached to the N- and C-Terminus of a Polypeptide Necessary to Help Form a Compact Structure.

Unlike the strict requirements for very high affinity for efficacy of peptides which bind to a second peptide sequence which is not covalently linked, the affinity requirements here for making a compact structure are less demanding. High affinity peptides may well work, but are not required. The tethering of a second copy of a homodimeric peptide at a fixed distance from the first dimerizer (separated by the polypeptide) will result in a very high local concentration of the second dimerizer. An estimate of this local concentration is derived for an 8mer polypeptide tethering the two together as follows: a linear 8mer is ca. 3 Å Iresidue×8 residues or 24 Å long when fully extended. A rough estimate of the distance from a second copy of the dimerizer would thus be in the range of 20 Å or less, since the peptide will not be fully extended in all (or even many) conformations. A solution with a second attached copy of a dimerizer every 20 Å away will have an effective concentration of ca. 0.2 mM. Thus peptides which form homo- or heterodimers at 1/100 of this concentration, or 2 uM and below, will be 99% cyclized by such a dimerizer. Thus any homo- or heterodimerizer with a binding constant (for itself or its dimeric partner) of 2 uM or below will be sufficient for the formation of 99%—cyclized peptides.

Based on minimized structures of peptide 1, the second copy of the dimerizer may be significantly closer to the first copy than 20 Å, depending on the folded state of the polypeptide inserted between the folding peptides. If on average it is 10 Å away, its local concentration will be roughly 1.6 mM, and 99% cyclized peptides will be attained from dimerizers with self-binding constants of 16 uM or less.

EXAMPLE 5

Synthesis of Peptide Constructs

The following materials were obtained from the indicated sources: Protected N-$\alpha$Fmoc amino acid derivatives were purchased from Advanced ChemTech (Louisville, Ky.) and all the peptide synthesis reagents such as diisopropylcarbodiimide (DIC), N-hydroxybenzotriazole (HOBt), 2-(1-H-Benzotriazole-1-yl)1,1,3,3-tetramethyluroniumhexafluorophosphate (HBTU), trifluoroacetic acid (TFA), N,N-diisopropylethylamine (DIPEA), piperidine, thioanisole, ethanedithiol and anisole were obtained from Sigma (St. Louis, Mo.). Pre-loaded Fmoc-Xaa-Wang-resins and H-Pro-2-Cl-Trt-resin (to synthesize C-terminal Pro peptides) were purchased from Novabiochem (La Jolla, Calif.). Organic solvents such as dimethylformamide (DMF) and dichloromethane (DCM) were from Fisher Scientific (Santa Clara, Calif.) and were of analytical grade.

The dimerizer scaffold peptides were synthesized on an automated Symphony/Multiplex multiple peptide synthesizer of Protein Technologies Inc., (Tucson, Ariz.) following classical Fmoc-chemistry. The duration for coupling (1.5 h/coupling) and deprotection (3×20 min) steps were slightly modified to the existing default program to achieve desired peptide in good yields. The pulsing rate of nitrogen gas to stir the resin mixture was carefully manipulated to ensure complete mixing of resin beads with the added reagents. Standard Fmoc-compatible side-chain-protection groups such as tertiary-butyl (tBu) for Ser, Thr, Glu, Asp, Tyr; trityl (Trt) group for Gin, His, Asn; tertiary-butyloxycarbonyl (Boc) group for Lys, Trp were used for the respective amino acid derivatives. Similarly, 2,2,4,6,7-pentamethyldihydrobenzofuran-5-sulfonyl (Pbf) group served as side-chain protection for Arg [Fields and Fields, Tetrahedron Lett. 34:6661 (1993)]. The coupling reactions were carried out twice with a five fold excess of Fmoc-protected α-amino acids in a mixture (50%, v/v) of DMF and DCM using DIC/HOBt mediated coupling procedure [Fields and Noble, Int. J. Pept. Protein Res. 35:161–214 (1990); Hudson, J. Org. Chem. 53:617–624 (1988)]. In some cases (coupling of Arg, His and Lys), triple coupling of amino acids were to be carried out in order to ensure completion of the reaction and also HBTU/HOBt coupling method was adopted in difficult situations [Knorr et al., Tetrahedron Lett. 30:1927–1930 (1989)]. Unreacted amino groups were capped with 50% acetic anhydride in DMF. After coupling five amino acids in an automated mode per sequence, synthesis was paused and completion of the coupling reaction was checked by Kaiser's test [Kaiser et al., Anal. Biochem. 34:595–598 (1970)] and proceeded further. At the end of the synthesis, the Fmoc group on the N-terminus was deprotected in 30 min with 25% piperidine in DMF and the resin was washed extensively with DCM followed by absolute ethanol. After an extensive wash with absolute ethanol, peptides were cleaved from the resin in manual mode by treatment with King's cleavage cocktail (Reagent K) composed of TFA (82.5%)/phenol (5%) thioanisole (5%)/ethanedithiol (2.5%)/water (5%) for 3 h at ambient temperature, during which, all the side-chain protections were also removed simultaneously [King et al., Int.

J. Pept. Protein Res. 36:255–266 (1990)]. After the cleavage, crude peptides were precipitated using cold diethylether after which the precipitate was solubilized in water/acetonitrile solution and lyophilized as described previously (Gururaja and Levine, Peptide Res. 9:283–289 (1996)].

The lyophilized crude peptide extracts were purified to homogeneity by reversed-phase high performance liquid chromatography (RP-HPLC) (Hewlett-Packard model 1100 series HPLC system having UV variable wavelength DAD detector; San Francisco, Calif., USA) using a semi-preparative Rainin (Woburn, Mass.) Dynamax 60 Å reversed-phase cyano column (10×250 mm) coupled to a guard column (10×50 mm). Mobile buffer consists of A: 0.1% TFA in water and B: 0.1% TFA in acetonitrile. A linear gradient of 040% buffer B in 40 min was employed to elute the peptide at a flow rate of 2.0 ml $min^{-1}$ using dual wavelength detection mode at 230 and 280 nm as described previously (Gururaja and Levine, supra). Fractions containing pure peptide were pooled and lyophilized. The integrity and identity of all the purified synthetic peptides were confirmed by on-line electrospray ionization-mass spectroscopy (ESI-MS) technique wherein the HPLC column outlet was connected directly to a Finnigan LCQ mass spectrometer (San Jose, Calif., USA) equipped with the standard ESI source. Mass spectrometric data were in good agreement with the expected values. The peptide EFLIVKS-STKSIPPQS-EFLIVKS, used for nmr studies, was over 99% pure as judged by LC/MS.

EXAMPLE 6

Peptide Dimerization Observed by Mass Spectrometry

Peptides were dissolved from a lyophilized white powder into water at pH 5.0, and the pH of the most concentrated stock was checked. After initial observation of peptide dimers when purifying the crude peptide, the Finnigan (San Jose, Calif.) LCQ mass spectrometer was tuned to optimize the signal intensity of the dimer at pH 5.0. The optimal parameters were: heated inlet capillary, 130–150° C., source voltage 4.0 kV, capillary voltage 38 v, tube lens offset 24 v, sheath gas 40–80 l/min., and auxiliary gas 20 l/min. All binding measurements were made using a continuous infusion rate of 5–15 10 μl/min. The relative ion current of the dimeric peptides was calculated as S (intensity of all dimer ions)/[S (all dimer ions)+S (all monomer ions)]; sodium adduct ions were included when observed.

To construct a scaffold with a self-associating peptide at each end, we examined variants of part of the sequence of a proposed self-associating peptide hormone, the neuropeptide head activator (Bodenmuller et al., supra). After some preliminary tests, an analog which contains a reversed sequence of part of the peptide was used for further studies. To establish the stoichiometry of binding of this analog, EFLIVKS, the self association was examined by electrospray mass spectrometry. For binding studies the mass spectrometer was tuned on the dimeric version of the peptide (see FIG. 3 and data not shown). No evidence for a trimeric or tetrameric peptide association was found. When the relative ion current of the dimer was plotted against the concentration of peptide infused into the source, a curve which is well fit by a rectangular hyperbola was seen (data not shown). This saturable dimer formation yields an apparent binding constant for EFLIVKS of 7.8 μM. This experiment was repeated with different analogs of this sequence (Table 1). Replacing the N-terminal glu with lys did not significantly change the binding, suggesting that these peptides do not dimerize simply by forming reciprocal lys-glu interactions. Addition of glu and lys to make EEFLIVKKS results in an apparent 4-fold increase in self-binding affinity. Each residue was individually replaced with alanine, and dimerization monitored. Replacement of the N-terminal glu and C-terminal ser had little effect on the apparent dimerization constant, while ala replacement of F2, L3, I4, V5 and K6 weakened binding 5.4-fold, 9.7-fold, 5.4-fold, 10-fold a 6-fold, respectively.

TABLE 1

Self-dimerization constants measured by mass spectrometry.

| peptide sequence | $K_d$(app)μM | peptide sequence | $K_d$(app)μM |
|---|---|---|---|
| EFLIVKS | 7.8 | AFLIVKS | 12 |
| KFLIVKS | 6.8 | EALIVKS | 42 |
| VSIKFEL | 13 | EFAIVKS | 76 |
| SKVILFE | 12 | EFLAVKS | 42 |
| EEFLIVKKS-acid | 2.1 | EFLIAKS | 82 |
| | | EFLIVAS | >50 |
| | | EFLIVKA | 9.9 |

EXAMPLE 7

Inhibition of Elastase by Peptide Constructs

The activity of 100 nM porcine pancreatic elastase (Sigma Chemical Co., St. Louis, Mo.) in 0.1 M Tris buffer, pH 7.88, at 25° C. was followed by cleavage of 100 μM succinyl-ala-ala-ala-p-nitroanilide at 412 nm for 1–2 min. The assay kinetics were linear over this time. Inhibition by different peptide constructs was followed by preincubation of 10 μM peptide with elastase for 1–1.5 min. followed by addition of the substrate. Percent inhibition was calculated as [1−{assay slope(peptide+elastase)/assay slope(elastase alone)}]× 100%. These assay conditions are identical to those used by Leatherbarrow and Salacinski, supra.

As a test sequence for insertion between the N- and C-terminal peptide sequence EFLIVKS used to constrain the test sequence, we chose a variant of the sequence of the 18mer Ci2b protease-inhibitory loop. This sequence has been reported (Leatherbarrow and Salacinski, supra) to be a very potent inhibitor of subtilisin, chymotrypsin and elastase. To test this, we assayed the inhibition of elastase under identical conditions to those reported with both the disulfide-cyclized form as well as the EFLIVKS-constrained analog. The results are shown in Table 2. At a concentration of 500 nM, the disulfide-cyclized peptide cyclic [CGTIVTMEYRIDRTRSFC] causes only a slight inhibition of porcine pancreatic elastase, 6.2% (n=3). Based on its reported apparent inhibition constant of 390 pM (Leatherbarrow and Salacinski, supra), and the concentration and Km of the substrate used in the assay, an inhibition of 99.9% would be estimated assuming this putative inhibitory peptide is competitive with substrate. The same 18mer sequence, with the N- and C-terminal val of the native sequence substituted for the cysteines, was also tested with different combinations of dimerizer peptides fused to its N- and C-termini. None gave significant inhibition of elastase (Table 2).

TABLE 2

Peptide Inhibition of porcine pancreatic elastase*.

| assay | inhibition | expected | n |
|---|---|---|---|
| 50 nM enzyme alone | 0% | 0% | 5 |
| +500 nM cyclic [CGTIVTMEYRIDRTRSFC] | 6.2 ± 1.2 | 99.9** | 3 |
| +10 μM EFLIVKSVGTIVTMEYRIDRTR-SFVEFLIVKS | −4.3 ± 0.3 | ? | 3 |
| +10 μM EFLIVKS-18 mer insert-SKVILFE | 7.0 ± 1.0 | ? | 3 |
| +10 μM SKVILFE-18 mer insert-EFLIVKS | 2.4 ± 0.29 | ? | 3 |
| +10 μM SKVILFE-18 mer insert-SKVILFE | −1.4 ± 0.14 | ? | 3 |
| +2 mM PMSF | 100 | 100 | 3 |

*assay at pH 7.88, 25 C, using 100 μM succ-ala-ala-ala-p-nitroanilide as a substrate, observed at 412 nm. Each value is derived from 3–5 replicates
**estimated as % = 100[inhibitor]/[inhibitor] + $K_i$(1 + [substrate]/$K_m$)
assuming the peptide is a competitive inhibitor with a $K_i$ of 390 pM

EXAMPLE 8

Elastolysis of Peptide Constructs

To examine the effects of elastase on different peptides, purified synthetic peptides (10 μM) were dissolved in 0.1 M Tris pH 7.88, at 25° C. Elastase was added to 100 nM. At time 0, 15 min., 1, 2, 3 and 24 hours, an aliquot of the reaction mixture was injected onto a 0.1×25 cm C18 reversed phase hplc column (Vydac Inc., Hesperia Calif.). The reaction mixture was eluted using a gradient of 100% A (99.9% H2O, 0.1% v/v trifluoroacetic acid) for 10 min., followed by a 1%/min. increasing gradient of B (99.9% acetonitrile, 0.1% trifluoroacetic acid) to 60% B, followed by a 5%/min. gradient of B to 100%. Peptides were examined by direct elution from the column into the source of a Finnigan LCQ ion trap mass spectrometer. Peptides were scanned from 300–2000 amu, and identified by searching their mass with that of different fragments of the full length peptide, or comparing their mass with different masses of expected elastolytic fragments in the case of the cyclic peptide, using MacBioSpec (obtained courtesy of PE-Sciex, Foster City, Calif.). Proteolysis of the reduced peptide CGTIVTMEYRIDRTRSFC was done in the presence of 2 mM dithiothreitol (Sigma). Cleavage products of the oxidized peptide were either directly chromatographed without reduction, or chromatographed after an aliquot was treated first with 1 mM PMSF for 1 hour and then with 30 mM DTT for 10 min.

To further examine the reason for the lack of expected elastase-inhibitory activity of cyclic [CGTIVTMEYRIDRTRSFC], and to examine the elastolytic stability of some of the peptide constructs in table 1, we incubated each peptide at a concentration of 10 uM with 100 nM elastase for 3 hours at pH 7.8, 25° C. Each reaction mixture was then chromatographed over a microbore C18 reversed phase column, and the peptide fragments were identified using mass spectrometry. The cyclic peptide reaction was examined either with or without subsequent reduction (data not shown). The linear peptide CGTIVTMEY-RIDRTRSFC was highly susceptible to elastolysis, giving ca. 11 different identifiable peptides (Table 3). The main cleavage was after Y9 and additional cleavages were after 14, V5, T6, M7, T14 and F17. Cyclic [CGTIVTMEYRIDRTRSFC] appeared to be cleaved more slowly than its linear analog, and after 3 hours was cleaved at fewer sites, mainly after Y9, and also after M7, T14 AND F17.

The Ci2b loop 18mer with EFLIVKS attached to each end was not attacked to a significant degree by elastase after 3 hours, with only cleavage after Y16 initially being observed. Most low level peaks observed in the chromatogram are mainly synthetic impurities also present in the absence of added elastase. After 24 hours, enough proteolysis occurred to assign additional elastolytic sites in this construct as after V5, M14, T21, F27 and I29. Thus cleavage occurred at many of the same residues as in the linear and cyclic peptides, but at a much reduced rate.

TABLE 3

Identification of elastolytic peptides of the Ci2b loop peptide and analogs.

| peptide substrate* | peptide substrate | peptide substrate |
|---|---|---|
| linear CGTIVTMEYRIDRTRSFC | cyclic [CGTIVTMEYRIDRTRSFC] | EFLIVKS-Ci2b insert-EFLIVKS |
| parent peptide 2150.2/2151.0 | parent peptide 2149.8/2150.5 | parent peptide 3775.2/3775.1 |
| CGTIVTMEY 1016.3/1016.44 | c[CGTIVTMEYRIDRTRSFC]H$_2$O 2168.3/2168.5-single cleavage in ring | EFLIVKSVGTIVTMEY 1828.6/1828.98 |
| RIDRTRSF 1050.6/1050.58 | CGTIVTMEY 1016.3/1016.44 | RIDRTRSFVEFLIVKS 1965.1/1965.14 |
| RIDRTRSFC 1152.6/1153.54 | RIDRTRSFC 1153.3/1152.6 | EFLIV or VEFLI 620.2/620.37 |
| CGTIVTMEYRIDRTRSF 2048.2/2048.0 | RIDRTRSF 1050.6/1050.58 | VEFLI or EFLIV 620.1/620.37 (second peak; both may be present) |
| CGTIVTMEYRIDRT 1658.0/1658.0 | EYRIDRT 952.4/952.49 | RSFVEF 784.4/784.4 |
| CGTIVTM 724.2/724.34 EYRIDRTRSFC 1444.9/1445.7 EYRIDRT 952.4/952.49 VTMEYRIDRTRSF 1673.8/1673.84 | | KSVGTIVTM 935.4/935.52 |

TABLE 3-continued

Identification of elastolytic peptides of the Ci2b loop peptide and analogs.

| peptide substrate* | peptide substrate | peptide substrate |
|---|---|---|
| MEYRIDRTRSFC 1576.9/1576.74 | | |
| MEYRIDRT 1083.6/1083.53 | | |
| TIMEYRIDRT 1184.6/1184.57 | | |

*presented as peptide fragment/observed monoisotopic mass/expected monoisotopic mass

EXAMPLE 9

Deuterium Exchange Experiments Using Constrained Loop Peptides

Deuterium exchange experiments were carried out by dissolving the peptide of interest in water at pH 5, and diluting the peptide 10-fold into $D_2O$ at t=0. For the initial constructs tested, the peptide concentrations after dilution in $D_2O$ were in the range of 10 μM. For other time points, an aliquot of the peptide solution was quenched by addition of a 2.5-fold volume excess of 1:1 $H_2O$:MeCN with 1% formic acid at 0° C. or 25° C. and immediately infused into the mass spectrometer. This acidic pH jump slows the rate of amide bond hydrogen exchange with solvent. For selected time points the mass derived from the first 2 min. of the infusion was compared to that of later 2 min. blocks to assess the significance of back-exchange, which was usually 1 proton or less. The total number of exchangeable protons was derived by 1) initially dissolving the peptide in DMSO, and diluting it directly into $D_2O$ before quenching and measurement of the new mass of the peptide several minutes later; 2) diluting a peptide dissolved in 5% DMSO 10-fold into $D_2O$; or 3) heating the solution of peptide diluted into $D_2O$ at 100° C. for 15 min. DMSO was included since in preliminary experiments low levels added to aqueous peptides appeared to greatly accelerate proton exchange. When all three methods were used with EFLIVKS-VGTIVTMEYRIDRTRSFV-EFLIVKS, they gave the same results. Calculation of the total protons exchanged included correction for the 10% by volume of $H_2O$ present after dilution in $D_2O$. For peptides which were soluble in the 1 mM range, samples from the 10-fold $D_2O$ solution at pH 5 were directly infused into the mass spectrometer without quenching. Rate constants and amplitudes for deuterium exchange were derived by fitting the time course of the gain in mass above the fully protonated form to a single exponential function.

Relative to surface-exposed residues, the amide backbone protons of peptides and proteins will exchange more slowly with deuterated water when they are buried in the interior of a protein (and inaccessible to water) or are involved in stable hydrogen bonding (Englander et al., Protein Science 6:1101–1109 (1997)]. Mass spectrometry has been used to examine the hydrogen exchange properties of a variety of different proteins (see Chung et al., Protein Science 6:1316–24 (1997) and Smith et al., J. Mass Spectrometry 32:135:146 (1997) for recent examples), and the existence of slowly exchanging protons has been used to infer the existence of tertiary structure [McKnight et al., J. Mol. Biol. 12:126–34 (1996)]. Deuterium exchange studies here were done at pH 5 since below pH 4.5 the constrained loops do not appear to retain structure as measured by circular dichroism (vide infra). To examine the compactness of the peptide dimerizer-constrained Ci2b loop peptide, the rate and stoichiometry of deuterium incorporation upon dilution into $D_2O$ was examined. The results for a variety of different constructs are summarized in Table 4.

TABLE 4

Deuterium exchange rates and amplitudes for constrained Ci2b peptide insert and other peptide inserts[1].

| dimerizer[1] | insert | total exchangeable protons | proton exchange amplitudes[3] | exchange rate constants |
|---|---|---|---|---|
| EFLIVKS | 18 mer[2] | 66.5 ± 1.4 | 29.3 ± 1.5 fast<br>16 intermediate<br>21 slow | k intermed = 0.054 hr - 1 |
| EEFLIVKKS | 18 mer | 70.3 | 39.4 fast<br>7.9 intermediate<br>23 slow | k intermed = 0.15 hr - 1 |
| MGEFLIVKS-insert-EFLIVKSGPP | 18 mer | | | |
| $K_6G_4$-EFLIVKS-insert-EFLIVKS $K_3$GSGS-EFLIVKS-insert-EFLIVKS-GSGSK$_3$ | 18 mer | 87.7 | 82.8 fast | |
| EFLKVKS | 18 mer | 71.6 | 70.1 fast | |
| SKVILFE | 18 mer | 66 | 31 fast<br>17 intermediate<br>18 slow | k intermed = 0.041 hr - 1 |

TABLE 4-continued

Deuterium exchange rates and amplitudes for constrained Ci2b peptide insert and other peptide inserts[1].

| dimerizer[1] | insert | total exchangeable protons | proton exchange amplitudes[3] | exchange rate constants |
|---|---|---|---|---|
| KFLIVKS | 18 mer | | | |
| EFLIVKS | -STKSIPPQS- | 36.1±1.9 | 32.6 ± 3.8 | fast |
| MGEFLIVKS-insert-EFLIVKSGPP | -G$_4$DYKDDDDKG$_4$- | 35.9 | 34.8 | |
| MGEFLIVKS-insert-EFLIVKSGPP | -G$_4$YPYDVPDYASLG$_3$- | 40.3 | 40.3 | |

[1]data is presented for peptides of the form dimerizer-insert-dimerizer; the dimerizer sequence is the same at the N- and the C-terminus except as noted
[2]the 18 mer standard insert is the Ci2b sequence - VGTIVTMEYRIDRTRSFV-
[3]the fast phase amplitude is calculated for the fastest exchange data, lasting at most ca. 1 hour The kinetics of deuterium exchange for protons for the construct EFLIVKS-VGTIVTMEYRIDRTRSFV-EFLIVKS-amide were determined (data not shown). A total of 66.5 Da was added to the time zero mass of the peptide upon complete proton exchange. In the fast phase of proton exchange, 29 protons exchanged; roughly 33 side chain, N- and C-terminal protons would be expected to be rapidly exchangeable at this pH if exposed to water. A further 16 protons exchanged at an intermediate rate with a rate constant of 0.054 hr–1. This left 21 protons which are presumed to exchange even more slowly than observable on this time scale. Both classes of protons exchange at a rate slower than measured for surface-exposed protons, taken from nearest neighbors identical to those found in EFLIVKS [Bai et al., Proteins: Structure, Function and Genetics 67:75–86 (1993)]. These control protons exchanged with deuterium with rate constants in the range of 6–60 hr$^{-1}$ at pH 5. Similar results were obtained with the reversed dimerizer sequence attached to the same end of the 18mer insert. With this 18mer insert, similar results were also obtained with an apparently more potent dimerizer (table 3) attached to each end of the insert, EEFLIVKKS. In this case, 39 of the 70 exchangeable protons exchanged with deuterium within an hour, 8 protons exchanged with a rate constant of 0.15 hr–1, and the remaining 23 protons exchanged more slowly than this. The total of 31 slowly exchanging protons in this analog was somewhat less than the 37 protons in the parent peptide, suggesting some subtle changes in structure between the two constructs. For the peptide analog with lys$_6$-gly$_4$-fused to the N-terminus of the parent peptide, designed to enhance the solubility of the peptide, all but ca. 5 protons exchanged within an hour. This N-terminal fusion may thus destabilize the structure or at least makes it more mobile.

The side chain of the isoleucine normally at the 4th position in this peptide appeared in the low energy conformers obtained from high temperature molecular dynamics trajectories (vide infra) to be buried in the folded peptide. Thus we created a single point mutation at the 4th position in each dimerizer (creating EFL<u>K</u>VKS), and examined the effect of this mutation on the 18mer insert structure by deuterium exchange. If this mutation disrupted the structure in a significant way, the number of slowly exchanging protons might be diminished. When the deuterium exchange kinetics were examined, all but one proton exchanged within an hour.

We also examined the effect of insert sequences different from Ci2b on the exchange kinetics of the overall peptide when EFLIVKS or its analogs were fused to both termini of these inserts. One insert, STKSIPPQS, represented an analog of the protease inhibitor cyclic[CTKSIPPQC] [Gariani and Leatherbarrow, J. Peptide Res. 49:467–75 (1997)]. This short construct had 36 exchangeable protons when heated, 33 of which exchanged in an hour. Thus if this peptide has a folded structure, it contains only a few slowly exchanging protons. A second insert included the flag epitope tag, DYKDDDDK, flanked by four glycines on each end to increase its flexibility so as to allow binding of the epitope to anti-flag antibodies. This was fused to MGEFLIVKS- at the N-terminus and -EFLIVKSGPP at the C-terminus. This peptide had 36 exchangeable protons, 35 of which exchanged within an hour. A similar construct, also expected to be somewhat flexible due to the presence of 7 glycines, was synthesized with the influenza hemagglutinin epitope tag replacing the flag tag. All protons were exchanged for deuterium within ca. 1 hour. Thus a shorter inserted sequence, or inserts with multiple glycines at each end to allow flexibility of the insert, did not have slowly exchanging protons.

EXAMPLE 10

Models of Peptide Constructs

None of the so far-examined peptide dimerizer constructs with slowly exchanging protons have been soluble in the millimolar range, thus structure determination by nmr is not readily accomplished. To derive a working model of selected structures, which can be roughly compared to secondary structure content derived from circular dichroism, we used high temperature molecular dynamics to generate conformers [Brooks, Chem. Scripta 29A:165–169 (1989); Bruccoleri and Karplus, Biopolymers 29:1847–62 (1990); Auffinger and Wipff, J. Comput. Chem. 11:190 (1990)] and subsequent thorough minimization to energy-rank different conformers. The lowest 5–7 kcal/mole energy band width conformers are then compared. This method of "quenched molecular dynamics" has been applied to a tumor surface octapeptide and peptide fragments of different proteins (Brooks, supra), tuftsin and its cyclic analogs [O° C.onnor et al., J. Med. Chem. 35:2870–81 (1992)], and to linear and cyclic melanotropins [Al-Obeidi et al., J. Peptide Res. 51:420–31 (1998)]. While this approach has also been applied to larger systems such as the 70 residues in hypervariable loops of antibodies [Bruccoleri and Karplus, Biopolymers 29:1847–62 (1990)] not enough conformers are generated for such large systems to provide complete conformational coverage [Dill, Biochemistry 24:1501–9 (1985)]. Thus this approach when applied to a 32mer will only allow examination of a few of the expected low energy conformers, giving only a rough idea of the overall fold. It may however allow a more significant coverage of conformation space for a cyclic 18mer or two linear 7mer peptides.

We applied this methodology first to the disulfide bond-constrained cyclic 18mer peptide, cyclic [CGTIVTMEYRIDRTRSFC], which is thought to be a sub-nM inhibitor of elastase and other proteases (Leatherbarrow and Salacinski, supra). For the cyclic peptide to be an inhibitor with similar potency to Ci2b, it presumably should have low energy conformers of similar structure and rigidity to the inhibitor loop of Ci2b. In its free form and in its complex with subtilisin Novo [McPhalen and James, Biochemistry 26:261–9 (1987)], the overall backbone of the inhibitor loop is roughly planar, with the R65, R67 and F69 side chains filling the interior of the loop. The edge which docks into the subtilisin binding site is an irregular beta sheet, with the side chains of I56, T58, M59, and Y61 extending into solution or into subtilisin in the bound complex, and the side chain of M59 noticeably bent from the solution structure when docked with subtilisin. The structure of the native loop and the energy distribution of the minimized conformers (two trajectories, 5.4 ns, 2700 structures) of this cyclic peptide was determined (data not shown). It is roughly Gaussian, as shown previously for cyclic melanotropin analogs (Al-Obeidi et al, supra). The low energy conformers found for the cyclic peptide mimicking the loop appear to be significantly more compact and globular than the native inhibitor loop (data not shown) and they have backbone atom root mean square deviations from the 18mer inhibitor loop of 6.22, 6.12, 5.46, 6.31, 5.72, 5.69 and 5.64 Å respectively. Residues 3–10, which form much of the subtilisin-contact region and which surround the reactive site of the inhibitor loop (met 7-glu 8), have heavy atom root mean square deviations from the same residues in the native loop of 5.65, 6.40, 3.95, 5.54, 5.20, 5.07 and 4.59 Å, respectively. In addition, the side chains of R65, R67 and F69 are not buried inside the loop region in any of these low energy conformers. These results are consistent with significantly different structures for the low energy conformers when compared to Ci2b's inhibitory loop. These significant structural differences are consistent with the failure to observe inhibition of elastase with this cyclic 18mer.

We next applied quenched molecular dynamics to look at low energy conformers of EFLIVKS when dimerized. These gas phase calculations may be particularly relevant to the low energy forms of peptide dimers observed by mass spectrometry. Peptide dimers were constructed by either tethering the two peptides together at approximately their centers of mass, or binding different parallel and antiparallel starting configurations (see the methods section) together in the gas phase before starting the conformation search. A total of 7 trajectories were run, covering 5250 minimized structures and 10.5 ns (data not shown) and a backbone overlay of the 14 lowest energy dimers, covering the lowest 7 kcal/mole energy bandwidth, from all of the trajectories was performed (data not shown). This was created by a least-squares superposition of all backbone atoms of one of the peptide dimerizers. Both peptides appear to adopt a turn conformation, but are not symmetric across the inter-dimer axis.

In addition a cluster graph of the 14 lowest energy conformers, in which the backbone atoms of each conformer are compared to those of every other conformer, and the RMSD deviation (Å) was created (data not shown). Two conformers are most similar if their RMSD difference is in the 0–1 Å range. There appears to be one main family of low energy conformers, and several other unique conformations (data not shown). For all of the peptides, both the N- and C-terminus of the first peptide, which are charged in these simulations, appear to be close to the N- and C-terminus of the second peptide of the dimer. Since each peptide has two acidic and two basic groups, there are a number of different intra-dimer ion pairs which are possible. Examination of the distances for all possible inter-dimer ion pairs in all 14 low energy conformers suggests that the most stable ion pairs are a) peptide 1: N terminus to peptide 2: glu 1: side chain carboxylate; b) peptide 1: lys 6 ϵ-amine to peptide 2: glu 1: side chain carboxylate; and c) peptide 2: C-terminus to peptide 1: lys 6:ϵ-amine. Both peptides form somewhat stable intramolecular ion pairs between their own N- and C-termini as well.

Quenched molecular dynamics was also used to examine low energy structures of the Ci2b 18mer test insert fused to EFLIVKS at each end (data not shown). This peptide is relatively inert to elastase, has 37 slowly exchanging protons, and shows no evidence for higher order aggregates (data not shown) when observed by mass spectrometry. A total of 6900 different structures were collected from 12.3 ns of dynamics trajectories. These structures were distributed in a Gaussian distribution (data not shown). Two conformers were at least 7 kcal/mole lower in energy than all others (data not shown). Both conformers appear compact and globular, consistent with other experimental results above. As with the EFLIVKS dimer modeled above, each termimal EFLIVKS attached to the 18mer insert appears to form a turn, and their N- and C-termini are within 3.8–4.3 Å. However, unlike the structure of the EFLIVKS dimer, their second termini, which are now fused to the 18mer insert, do not loop back to the center of the molecule, but are instead 11.5–15 Å apart in the two conformers. This distance is significantly greater than the comparable distance in the native Ci2b structure (4.1 Å) and in the cyclic peptide low energy conformers (6.88 Å on average) suggesting that the dimerizer peptides, at least with this insert, form a "loop" with a fairly wide base. The 18mer insert also appears to contain a significant proportion of turn structure, consistent with circular dichroism measurements.

EXAMPLE 11

Circular Dichroism Studies, NMR Measurements and Peptide Conformation Searches on Peptide Constructs Circular Dichroism Measurement CD spectra were recorded on an AVIV 62A DS CD spectropolarimeter (Lakewood, N.J., USA) equipped with a Peltier temperature control unit. The temperature of the instrument was maintained constantly below 20° C. using Neslab CFT-33 refrigerated recirculator water bath. The device was periodically calibrated with the ammonium salt of (+)-10-camphorsulfonic acid according to manufacturer's recommendations. Spectra were recorded between 250 and 195 nm at 0.2 nm intervals with a time constant of 1 s at 25° C. Data were collected from five separate scans and averaged using an IBM PS/2 computer. A cylindrical quartz cell of path length 0.1 cm was used for the spectral range with the sample concentration of 0.02–0.05 mM as determined by amino acid analysis. Peptide stock solutions (1 mM) were made in 10 mM $KPO_4$ buffer containing 100 mM KF at pH 7.5 except as noted. For pH titration experiments, pH of the buffer was carefully adjusted to desired value using either 0.1 M HCl or 0.1 M NaOH before adding the above peptide stock solution. Mean residual ellepticity (MRE) in deg.cm$^2$.dmol$^{-1}$ was obtained through the equation $$MRE(\lambda) = \Theta(\lambda)/10\ l\ c\ n$$

where $\Theta(\lambda)$ is the ellipticity in degrees at wavelength $\lambda$, l is the path length in cm, c is the concentration in M, and n is the number of residues in peptide/protein [Schmidt, in *Protein Structure: A Practical Approach*, IRL Press, New York, pp 251–285 (1989)]. Raw data collected from individual experiments were converted to an ASCII format and the plots were created using Microsoft Excel software package as described previously [Gururaja and Levine, Peptide Res. 9:283–289 (1996)]. Thermal denaturation data were taken on samples containing 20 μM peptide in 10 mM KPO$_4$ buffer containing 100 mM KF at pH 7.5. The thermal denaturation was measured at 220 nm over a range of 4–98° C. with a temperature step of 2° C. and a 2 min equilibration time and a 60 s signal averaging time. Apparent T$_m$ was calculated as the maximum of the first derivative of the CD signal at 220 nm with respect to T$^{-1}$. CD spectra were deconvoluted with the program? C.D spectra were deconvoluted using the program Dichroprot v. 2.4, which uses the variable selection method of Johnson.

NMR Measurements

All deuterated solvents such as D$_2$O (99.96% D) and DCI (99.5% D) for NMR experiments were purchased from Cambridge Isotope Laboratories (Andover, Mass.). Samples (~1 mM) were prepared by dissolving the synthetic peptide in 0.7 ml of H$_2$O:D$_2$O 90:10 (v/v) or 100% D$_2$O. Sample in water was prepared by the dissolution of HPLC purified peptide, adjusting the pH to 4.0 with HCl or DCI. All pH values were measured at room temperature; the values reported herein are apparent pH values and were not corrected for the deuterium isotope effect. TSP [3(trimethylsilyl)propionic-2,2,3,3-d$_4$ acid, sodium salt] was used as an internal chemical shift standard.

$^1$H NMR experiments were performed on a Varian Unity INOVA-500 spectrometer at 25° C. equipped with a Sun-sparcstation 5 as described previously [Naganagowda et al., J. Biomol. Struct. Dynam. 16:91–107 (1998)]. Two dimensional Double Quantum Filtered Correlated Spectroscopy (DQF-COSY) [Rance et al., Biochem. Biophys. Res. Commun. 117:479–485 (1983)], Total Correlation Spectroscopy (TOCSY) [Bax and Davis, J. Magn. Reson. 65:355–360 (1985)], Rotating frame Overhauser enhancement spectroscopy (ROESY) [Bothner-By et al., J. Am. Chem. Soc. 106:811–813 (1984)] and Nuclear Overhauser Enhancement Spectroscopy (NOESY) [Macura and Ernst, Mol. Phys. 41:95–117 (1980)] experiments were acquired in pure phase absorption mode with quadrature detection in t$_1$ dimension using the hypercomplex method [States et al., J. Magn. Reson., 48:286–292 (1982)]. The carrier was placed on the water resonance to enable irradiation of the water during the relaxation delay (1.5 to 2.5 s) and during mixing time in NOESY experiments. For TOCSY spectra, MLEV-17 sequence was used with a spin lock time of 50 to 85 ms. For ROESY experiments spin lock times of 200 and 250 ms were used while for NOESY, mixing times of 200 and 300 ms were used. $^1$H NMR spectrum in H$_2$O had a spectral width in both the dimensions of 5400 Hz. In D$_2$O solvent, after complete exchange of the amide protons, the spectrum was recorded by reducing the spectral width to 3000 Hz in both the dimensions. 256 or 512 t$_1$ increments were acquired with a size of 1024 or 2048 data points. Slowly exchanging amide protons were identified by dissolving the samples in D$_2$O and recording 1D and TOCSY spectra, immediately. For temperature coefficient measurements of the amide protons, 1D and TOCSY experiments were performed between 25 and 50° C. in steps of 5° C. Typically 16 or 32 scans were collected for DQF-COSY and TOCSY spectra, and 64 scans for ROESY and NOESY spectra. Prior to Fourier transformation, the free induction decays (FIDs) were zero filled once in both dimensions. For processing of DQF-COSY spectra, a squared sine-bell window function shifted by 90° was used in both the dimensions, whereas for the TOCSY, ROESY and NOESY spectra, the data were processed separately, using 90° and 45° shifted squared sine-bell window functions.

The $^1$H-$^1$H distances for structure determination were deduced from NOE cross peak intensities in the 2D-NOESY spectrum obtained with 200 ms mixing time in water. Ranges of interproton distances were calculated by comparing the volume of the cross peaks and were categorized into three classifications, 1.8–2.5 Å (strong), 2.5–3.5 Å (medium), and 3.5–5.0 Å (weak), for the distance geometry calculations. The vicinal coupling constants $^3J_{NH-C\alpha H}$ of each residue were taken from the NMR studies and used to estimate possible torsional angles via the Karplus relationship [Karplus, J. Chem. Phys. 30:11–15 (1959)]: $^3J_{NH-C\alpha H} = A\cos^2\theta - B\cos\theta + C$ where $\theta = |\phi_- -60°|$. The A, B and C constants proposed by Pardi et al., J. Mol. Biol. 180:741–751 (1984) have values of 6.4, 1.4 and 1.9, respectively. The techniques used to obtain conformational data will only be briefly summarized as these have been discussed in great detail elsewhere. Delineation of conformation from NMR technique is purely based on the measurement of torsional angles along the polypeptide chain using two-dimensional NMR data acquired at high magnetic field strength. Specifically, to assign protons that are coupled through bond, TOCSY experiments are performed. Sequential assignments, for example Hα(i)-NH(i+1), are based on NOESY and ROESY experiment, in which a correlation is observed between protons in close spatial proximity which is then an indicator of conformations.

Peptide Conformation Searches

Low energy conformers of different peptide constructs were generated as follows. Explicit atom models of the peptide constructs were built using Insight II 95.0 (Molecular Simulations Inc., San Diego, Calif.) and the cff91 forcefield [Maple et al., J. Comp. Chem. 15:162–182 (1994)]. Peptides were modeled as zwitter ions, with lys, arg, asp and glu fully ionized in addition to the N-terminal amine and C-terminal carboxylate. The effects of an aqueous solvent environment and counterion screening were simulated by the use of a linear distance-dependent dielectric constant. The Verlet algorithm [Verlet, Phys. Rev. 159:98–103 (1967)] with a time step of 1 fs was used to integrate the equations of motion; this was implemented as the default leapfrog algorithm of Discover 2.9.7. A 15 A cutoff was used for nonbonded interactions. Peptide bonds were restrained to the trans conformation at high temperatures using a torsional restraint of 5 kcal/mol/rad$^2$. In the dynamics protocol, based on modifications of a program written by Mackay et al. [Mackey et al., in *Prediction of Protein Structure and the Principles of Protein Conformation*, (Fasman, ed.; New York, Plenum Press) pp 317–358 (1989)], the starting peptide structures were first minimized using 300 steps of steepest descent and 1000 steps or as many steps of conjugate gradient minimization as necessary so that the maximum energy derivative was less than 0.1 kcal/A, to remove high energy structures created during construction of the molecule. The peptide atoms were assigned random initial velocities using the dseed variable, and the peptide was heated to 900 K over 2 ps. Individual trajectories were continued for times varying from 400 ps to 3 ns with individual structures collected every 1–2 ps for subsequent minimization. Each saved structure was equilibrated at 900 K for 50 fs, cooled to 300 K over 5 ps, and minimized with 300 steps of the steepest descents algorithm followed by Fletcher-Reeves conjugate gradient minimization using as many steps as necessary to give a maximum energy derivative of less than 0.001 kcal/mole/A. The minimized total energy vs. number of conformers in individual 5 kcal/mole windows was plotted for each peptide. The conformers in the lowest 5 kcal/mole window above the minimum energy [O° C.onnor et al., J. Med. Chem. 35:2870–81 (1992)] were selected for further analysis.

Starting structures for the different peptides were obtained as follows. For dimerized EFLIVKS, extended structures were aligned in a parallel or anti-parallel fashion, with the Cyl of ile 4 ca. 7 A apart, giving 4 different starting structures. Two extended structures (parallel and antiparallel) were tethered together with an energy penalty of 100 kcal/mole when the distance between the Cyl of ile 4 of both peptides was outside of the range of 1.5–12 A. For the putative protease inhibitor cyclic [CGTIVTMEYRIDRTRSFC] the initial structure was a mixture of right handed alpha helix and beta sheet allowing formation of a disulfide bond between the two terminal cysteines. A second run started with a partially minimized version of the first structure.

For the peptide dimer-constrained construct EFLIVKS-VGTIVTMEYRIDRTRSFV-EFLIVKS, several different starting structures were used. One started from the Ci2b-based structure (PDB file 2Cl2) of the 18mer insert, which was derived by removing all residues from the crystal structure except for the inhibitor loop, and mutating individual residues to give the 18mer sequence reported in Leatherbarrow and Salacinski (supra). EFLIVKS in an extended conformation was fused to each end of the peptide and the resulting construct was minimized as above. A second structure started from EFLIVKS fused as a beta sheet to each end of the 18mer Ci2b insert. A third started from EFLIVKS fused as a right handed alpha helix to each end of the 18mer Ci2b insert. A fourth started from an extended conformation for the entire construct, and a fifth started from a different partially extended conformation. A sixth run started with the entire construct as a beta sheet.

Since the peptides studied here are soluble at neutral or near-neutral pH at levels well below the millimolar range needed for an nmr structure determination, we examined their solution structure using circular dichroism (CD). Circular dichroism measurements are sensitive to the secondary structure of both peptides and proteins, and have been extensively used to examine the conformation of both [Bloemendal and Johnson, Pharm. Biotechnol. 7:65–100 (1995); Woody, Methods Enzymol. 246:34–71 (1995); Greenfield, Anal. Biochem. 235:1–10 (1996)]. Here these measurements are used to examine the pH-dependence of secondary structure formation and stability, to compare the effects on insert structure of different dimerizers, to examine the effects of mutations in the dimerizers, and to look at the effects of different insert sequences on the overall structure of dimerizer-constrained loops. When these measurements are combined with measurements of proteolytic susceptibility, deuterium exchange, and the results of conformational searches, they give information on the overall structure and folding of the mini-loops examined here.
EFLIVKS-dimerized 9mer Insert The first insert examined was EFLIVKS-STKSIPPQS-EFLIVKS. The 9mer insert represents an analog of the protease inhibitor cyclic[CTKSIPPQC] (Gariani and Leatherbarrow, supra). The CD spectrum was recorded between pH 3.5–8.5 (data not shown). A pH-dependent transition in secondary structure was observed. At pH 3.5, a secondary structure with a strong minimum at 201 nm was seen. While this is near the expected minimum for a random coil [Greenfield and Fasman, Biochemistry 8:4108–4116 (1969)] of 195–197 nm, the shape of the spectrum is also similar to that of a type 1 beta turn observed in a short peptide [Perczel et al., Int. J. Peptide Protein Res. 41:223–236 (1993)].

$^1$H-NMR Examination of Low pH Structure

As this CD spectrum was seen with a number of other inserts under defined conditions, and since this peptide was quite soluble at low pH, we examined this structure using nmr. The resonance assignments of the $^1$H-NMR spectrum of 9mer insert in water were made by standard sequential assignment procedures [Wuthrich, in NMR of Proteins and Nucleic Acids, New York, Wiley-lnterscience, pp 166ff (1986)]. The assignments of $^1$H resonances were accomplished by the combined analyses of 2D-TOCSY and 2D-NOE spectra. The 2D-TOCSY spectrum was also recorded at various temperatures (25 to 50° C.) to resolve overlapping connectivities for unambiguous assignments, and was also used to determine the temperature coefficients of the NH chemical shifts. The resonances buried under the water signal (in 90% H$_2$O) were assigned by recording the spectra in 100% D$_2$O. The chemical shifts of all the assigned protons are listed in Table 5. The temperature coefficients of NH chemical shifts, $^1$H/$^2$H exchange rate of amide groups, $J_{NH-C\alpha H}$ values, and a set of characteristic strong, medium, and weak NOE connectivities have been used as criteria to examine whether the peptide has any preferred backbone conformation in aqueous solution.

The temperature coefficients of all amide resonances are found to be =0.004 ppm K$^{-1}$ (data not shown), suggesting that the backbone NH groups are exposed to the solvent and not involved in any intramolecular hydrogen bonding interactions. The fast $^1$H/$^2$H exchange rate observed for all backbone amide resonances provides further evidence that the amide groups are not involved in any intramolecular hydrogen bonding. The prevalence of strong $d_{\alpha N(i,\ i+1)}$ and weak $d_{\alpha N(i,\ i)}$ NOEs and a continuous stretch of weak and medium $d_{\beta N(i,\ i)}$ and $d_{\alpha\beta N(i,\ i)}$ NOEs in the absence of any observable $d_{NN}$ NOE interactions indicate that the backbone dihedral angles are predominantly in the unfolded extended region of $\phi$, $\phi\_$space [Rance et al., Biochem. Biophys. Res. Commun. 117:479485 (1983); Pardi et al., J. Mol. Biol. 180:741–751 (1984)]. The $J_{NH-C\alpha H}$ values provided in Table 5 are in the range of 6.5 to 8.4 Hz for all residues except Ser-7. For a regular β-strand, the $J_{NH-C\alpha H}$ is expected to be ~9 Hz, while for α-helix it is ~4.0 Hz [Rance et al., Biochem. Biophys. Res. Commun. 117:479485 (1983); Pardi et al., J. Mol. Biol. 180:741–751 (1984)]. The coupling constants of 6.5–8.4 Hz observed for this peptide suggest the existence of populations of unfolded nonhydrogen bonded conformations of comparable energy with $\phi$ values exceeding the regular helical region. Collectively, the NMR data provide evidence that EFLIVKS-STKSIPPQS-EFLIVKS is unstructured in aqueous solution.

TABLE 5

Compilation of $^1$H Chemical Shift values for EFLIVKS-STKSIPPQS-EFLIVKS at pH 4.0.

| Xaa (No.) | NH | C$^\alpha$H | $^3$J$_{NH-C\alpha H}$ | C$^\beta$H | C$^\gamma$H | C$^\delta$H | C$^\epsilon$H |
|---|---|---|---|---|---|---|---|
| E-1 | — | 3.870 | — | | | | |
| F-2 | 7.941 | 3.954 | 8.13 | 3.005 2.805 | — | — | |
| L-3 | 8.060 | 4.193 | 7.80 | 1.347 1.347 | 1.347 | 0.722 0.670 | |
| I-4 | 7.926 | 3.978 | 7.92 | 1.678 | 1.380 1.025 | 0.713 | |
| V-5 | 8.116 | 3.946 | 8.22 | | | | |
| K-6 | 8.342 | 4.190 | 6.54 | 1.680 1.590 | 1.270 1.270 | 1.525 1.525 | 2.827 2.827 |
| S-7 | 8.237 | 4.300 | 6.17 | 3.710 3.710 | — | — | — |
| S-8 | 8.338 | 4.369 | 6.66 | 3.775 3.715 | — | — | — |
| T-9 | 8.080 | 4.180 | 7.23 | 4.060 | 1.048 | — | — |
| K-10 | 8.182 | 4.208 | 6.68 | 1.690 1.590 | 1.280 1.280 | 1.525 1.525 | 2.839 2.839 |
| S-11 | 8.090 | 4.320 | 7.58 | | | | |
| I-12 | 8.114 | 4.320 | 8.02 | 1.700 | 1344 1.030 | 0.771 | — |
| P-13 | — | 4.196 | — | | | | |
| P-14 | — | 4.266 | — | | | | |
| Q-15 | 8.365 | 4.117 | 6.96 | 1.950 1.860 | 2.240 2.240 | — | — |
| S-16 | 8.146 | 4.212 | 6.73 | | | | |
| E-17 | 8.110 | 4.096 | 6.93 | 2.090 1.876 | 2.148 | — | — |
| F-18 | 7.946 | 4.438 | 8.22 | 3.005 2.805 | — | — | — |
| L-19 | 7.822 | 4.181 | 8.02 | 1.487 1.487 | 1.487 | 0.738 0.694 | — |
| I-20 | 8.045 | 3.948 | 7.97 | 1.642 | 1.350 1.020 | 0.720 | — |
| V-21 | 8.151 | 3.936 | 8.19 | 1.860 | 0.748 0.748 | — | — |
| K-22 | 8.295 | 4.220 | 6.73 | 1.700 1.600 | 1.290 1.290 | 1.530 1.530 | 2.835 2.835 |
| S-23 | 8.173 | 4.290 | 7.79 | | | | |

At pH 4.5, a different secondary structure was observed, which remained stable up to pH 8.5. The CD spectra at pH 4.5–7.5 had a much diminished band at 202 nm, indicating a loss of random coil. They also had a slight positive band at ca. 210–215 nm, and a negative band around 228–230 nm, indicating the presence of beta turns [Brahms and Brahms, J. Mol. Biol. 138:149–178 (1980)]. Since at pH 5.0 this construct has 3 or fewer slowly exchanging protons (table 4), the peptide may be unfolded at this pH (i.e. it has no tertiary structure) but with a secondary structure containing some beta turn and significantly less random coil than at pH 3.5. Alternatively, if it is folding and has some tertiary structure, the backbone is mobile enough so that no amide protons are sequestered from solvent for a long period of time. When observing the CD spectrum at 225 nm, the structure present at pH 7.5 has a $T_m$ of 39.6±1° C. (data not shown).

EFLIVKS-VGTIVTMEYRIDRTRSFV-EFLIVKS

A second construct examined by CD contained the Ci2b 18mer insert, EFLIVKS-VGTIVTMEYRIDRTRSFV-EFLIVKS. The pH-dependence of the CD spectrum of this peptide was determined (data not shown). Unlike the first peptide examined above, the CD spectrum is not as pH-dependent, and does not appear to have a major amount of random coil. The strong maximum around 210 nm and strong minimum at 225–230 nm are consistent with a significant content of beta turn structure at all pH values examined turns [Brahms and Brahms, J. Mol. Biol. 138:149–178 (1980)]. The smaller minimum seen at ca. 200 nm is consistent with a small percent of random coil, or the presence of a type II beta turn [Perczel et al., Int. J. Peptide Protein Res. 41:223–236 (1993)]. Using the signal at 225 nm, the peptide can be melted with temperature, with a $T_m$ of 39.85±1.6° C.

Constructs With an N-terminal MG- and C-terminal -GPP

For peptide expression in live cells, MG- was added to the N-terminus of a number of peptide constructs, and -GPP was added to the C-terminus to block proteolysis by cellular carboxy peptidase [Vanhoof et al., FASEB J. 9:73644 (1995)]. The CD spectra of a variety of these peptides were then compared at pH 7.5 (data not shown). Examination of the pH-dependence of the CD spectrum of MGEFLIVKS-Ci2b insert-EFLIVKSGPP was performed (data not shown) and suggests that the additional five residues cause significant changes in the CD spectrum compared to EFLIVKS-Ci2b insert-EFLIVKS. The positive band at 208 nm is no longer distinct, and the negative band at 200 nm has disappeared. The major minimum around 225 nm (characteristic of some beta turn structure) remains. Thus the addition of these five-residues appears to cause distinct conformational changes, but not unfolding of the structure.

Addition of other insert sequences also resulted in rather different CD spectra. An insert consisting of the flag epitope tag with glycine spacers, -G$_4$DYKDDDDKG$_4$-, designed to allow detection of expressed peptide in cells using Western blots, resulted in a CD spectrum containing a minimum at ca. 202 nm and a small minimum at ca 220 nm (data not shown). Based on the similarity of this spectrum to that of EFLIVKS-STKSIPPQS-EFLIVKS, this peptide appears to be mainly random coil between pH 3.5–8.5. This construct does not have slowly exchanging protons, consistent with its unfolded structure. An insert consisting of the influenza hemagglutinin epitope tag with glycine spacers, -G$_4$YPYDVPDYASLG$_3$-, gives a CD spectrum with a minimum at 205–207 nm and a second smaller minimum at ca. 220 nm (data not shown). This may be due to a somewhat different composition of secondary structures, and could include some alpha helix (due to the minimum at 205–207 nm) as well as random coil or beta turn. Since this construct also did not have slowly exchanging protons (table 4), the CD spectrum may reflect the presence of only secondary structure.

Other Additions to the EFLIVKS Sequence

The effects of mutations in the EFLIVKS sequence on the CD spectrum of the Ci2b peptide insert were determined (data not shown). The peptide EEFLIVKKS-Ci2b insert-EEFLIVKKS is of particular interest, since it has 23 slow-exchanging protons and 8 intermediate-exchanging protons (table 4) and thus may have tertiary structure, and because this dimerizer may have a somewhat higher self-affinity than EFLIVKS. It gives a CD spectrum which is similar to that of the control peptide, except that the minimum at 202 nm is missing, and the maximum at 210 nm (control peptide) is shifted closer to 207 nm. This peptide thus appears to have beta turn structure and less random coil than the control peptide.

To increase the solubility of the structure, lysines were added to the N-terminus with a glycine spacer. 15 For the construct KG$_4$-EFLIVKS-Ci2b insert-EFLIVKS, a very different CD spectrum was obtained than for the control peptide, with a broad minimum at ca. 220 nm (data not shown). This spectrum does not appear to be characteristic of any one dominant secondary structure, but can be deconvoluted to a mixture of beta sheet and beta turn (58%), alpha helix (14%) and the rest random coil. Since this structure has at most 5 slowly exchanging protons (table 4), the additional residues added to the N-terminus appear to have destabilized the tertiary structure of the control peptide, while creating a different secondary structure.

Mutations in the EFLIVKS Sequence

Three charge modifications of the dimerizer sequence were tested at pH 7.0. In one peptide, a single lys and glu were switched between dimerizers, giving KFLIVKS-Ci2b insert-EFLIVES. In a second peptide, the glutamate of each dimerizer was mutated to lysine, giving KFLIVKS-Ci2b insert-KFLIVKS. In a third peptide, the lys of each dimerizer was mutated to glu, giving EFLIVES-Ci2b insert-EFLIVES. Each peptide had a CD spectrum resembling that of the control peptide of EFLIVKS-Ci2b insert-EFLIVKS (data not shown). In a second set of mutations, the hydrophobic character of the dimerizer was changed. First, F2 and I4 in both EFLIVKS sequences were mutated to lysine or to serine, giving a dimerizer sequence on each terminus of the Ci2b insert of EKLKVKS or ESLSVKS. This resulted in a major change in the CD spectrum, with the appearance of a large negative band at 202–265 nm, indicating a significant increase in random coil structure, or denaturation (data not shown).

Second, only I4 was mutated to lysine in each dimerizer. This also changed the CD spectrum in a similar fashion (data not shown). This construct had at most 1–2 slowly exchanging protons, suggesting that this single change in the hydrophobic core of the EFLIVKS sequence was sufficient to disrupt the structure of the entire peptide construct.

We claim:

1. A molecular library comprising a plurality of members, each member comprising a recombinant nucleic acid encoding a fusion protein comprising a first dimerization peptide that is no more than 8 amino acids long and comprises the sequence $FLIVX_5$, wherein $X_5$ is selected from the group consisting of K, R, D and E.

2. A molecular library according to claim 1, wherein said first dimerization peptide comprises the sequence FLIVK (SEQ ID NO:18).

3. A molecular library according to claim 1, wherein said first dimerization peptide comprises the sequence KFLIVKS (SEQ ID NO:22).

4. A cellular library comprising a plurality of cells, each cell comprising a member of the molecular library of claim 1.

5. A molecular library according to claim 1, wherein said first dimerization peptide comprises the sequence EFLIVES (SEQ ID NO:34).

6. A molecular library according to claim 1, wherein said first dimerization peptide comprises the sequence EEFLIVKKS (SEQ ID NO:23).

7. A molecular library according to claim 1, wherein said fusion protein further comprises a second dimerization peptide.

8. A molecular library according to claim 7, wherein at least one of said first and said second dimerization peptides comprises a sequence selected from the group consisting of: EFLIVKS (SEQ ID NO:6), KFLIVKS (SEQ ID NO:22), EFLIVKKS (SEQ ID NO:23), AFLIVKS (SEQ ID NO:25), EFLIVKA (SEQ ID NO:31), and EFLIVES (SEQ ID NO:34).

9. A molecular library according to claim 7, wherein said fusion protein further comprises at least a random peptide positioned between said first and said second dimerization peptides.

10. A molecular library according to claim 1, wherein each member is contained within a retroviral vector.

11. A molecular library according to claim 10, wherein said retroviral vector further comprises a nucleic acid encoding a selection marker.

12. A molecular library according to claim 11, wherein said selection marker is green fluorescent protein.

13. A molecular library according to claim 10, wherein said retroviral vector futher comprises an internal ribosome entry site (IRES).

14. A molecular library comprising a plurality of members, each member comprising a recombinant nucleic acid encoding, in order, a first dimerization peptide, a random peptide, and a second dimerization peptide, wherein one of said first and second dimerization peptides comprises the sequence $FLIVX_5$, wherein $X_5$ is selected from the group consisting of K, R, D and E.

* * * * *